United States Patent
Goodman et al.

(10) Patent No.: US 6,804,992 B2
(45) Date of Patent: Oct. 19, 2004

(54) SYSTEM AND METHOD FOR PROCESSING ULTRASONIC SIGNALS

(75) Inventors: Mark A. Goodman, Cortlandt, NY (US); William Bishop, Pleasantville, NY (US)

(73) Assignee: U-E Systems, Inc., Elmsford, NY (US)

( * ) Notice: Subject to any disclaimer, the term of this patent is extended or adjusted under 35 U.S.C. 154(b) by 0 days.

(21) Appl. No.: 10/385,980

(22) Filed: Mar. 11, 2003

(65) Prior Publication Data

US 2004/0090866 A1 May 13, 2004

Related U.S. Application Data

(63) Continuation-in-part of application No. 10/292,799, filed on Nov. 12, 2002, now Pat. No. 6,707,762.

(51) Int. Cl.[7] .............................................. G01M 3/24
(52) U.S. Cl. ...................................... 73/40.5 A; 702/51
(58) Field of Search ............................ 73/40.5 A, 592, 73/587; 702/51

(56) References Cited

U.S. PATENT DOCUMENTS

| | | |
|---|---|---|
| 3,374,663 A | 3/1968 | Morris |
| 3,978,915 A | 9/1976 | Harris ........................ 165/11 |
| 4,785,659 A | 11/1988 | Rose et al. .............. 73/40.5 A |
| 4,987,769 A | 1/1991 | Peacock et al. .............. 73/49.7 |
| 5,089,997 A | 2/1992 | Pecukonis .................... 367/135 |
| RE33,977 E | 6/1992 | Goodman et al. ........ 73/40.5 A |
| 5,650,943 A | * 7/1997 | Powell et al. .................. 702/51 |

FOREIGN PATENT DOCUMENTS

| | | | | |
|---|---|---|---|---|
| JP | 62-80535 | * | 4/1987 | .............. 73/40.5 A |
| JP | 1-109235 | * | 4/1989 | .............. 73/40.5 A |

\* cited by examiner

*Primary Examiner*—John E. Chapman
(74) *Attorney, Agent, or Firm*—Darby & Darby

(57) ABSTRACT

A system and method for eliminating confusion associated with checking valves, wherein additional test points are added to the measurement of a valve for ensuring the verification of the actual sources of leaks or turbulence. A base line measurement for the valve is established by measuring the level of ultrasonic sound at the two points upstream from the valve. The level of the ultrasound at two downstream points is then measured. The value of the ultrasound at the downstream test points is compared to the values of the ultrasound at the upstream test points. If the values of ultrasound at the downstream test points are higher than the values of the ultrasound at the upstream test points, then the valve is leaking. If the values of the ultrasound at the downstream test points are close to or lower than the values of the ultrasound at the upstream test points, then the valve is not leaking, i.e., the valve is good.

15 Claims, 48 Drawing Sheets

TO POWER SUPPLY

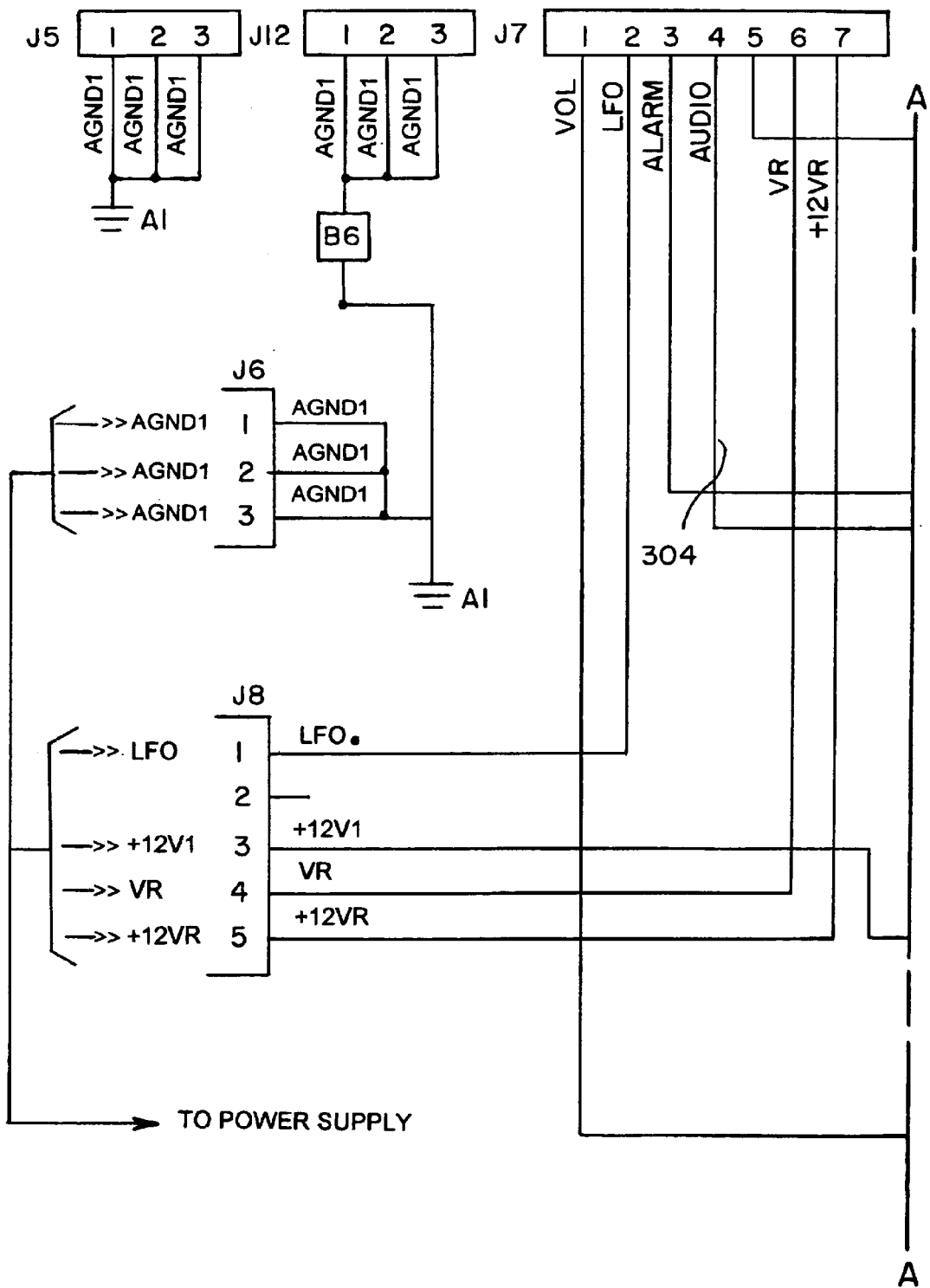

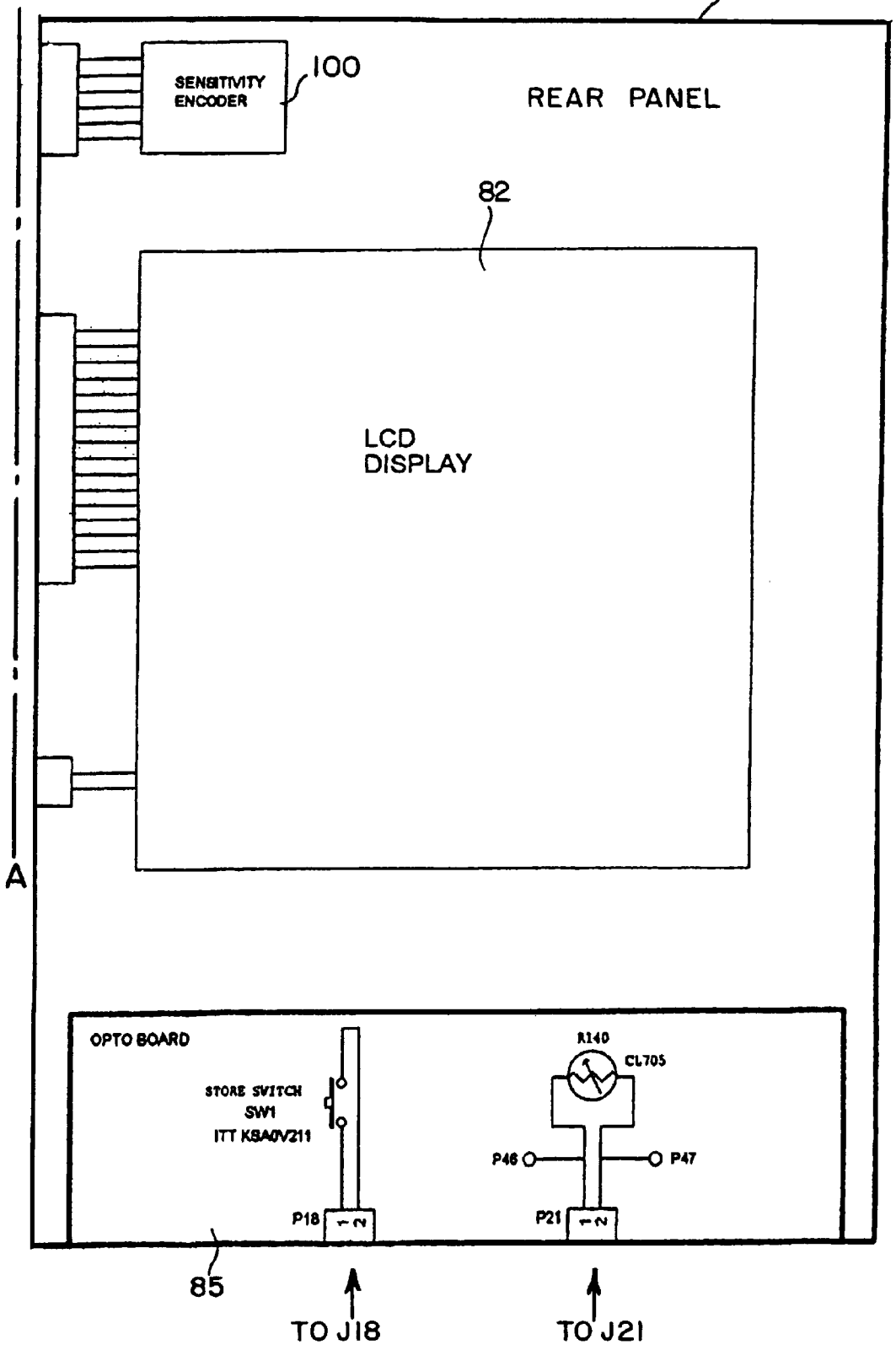

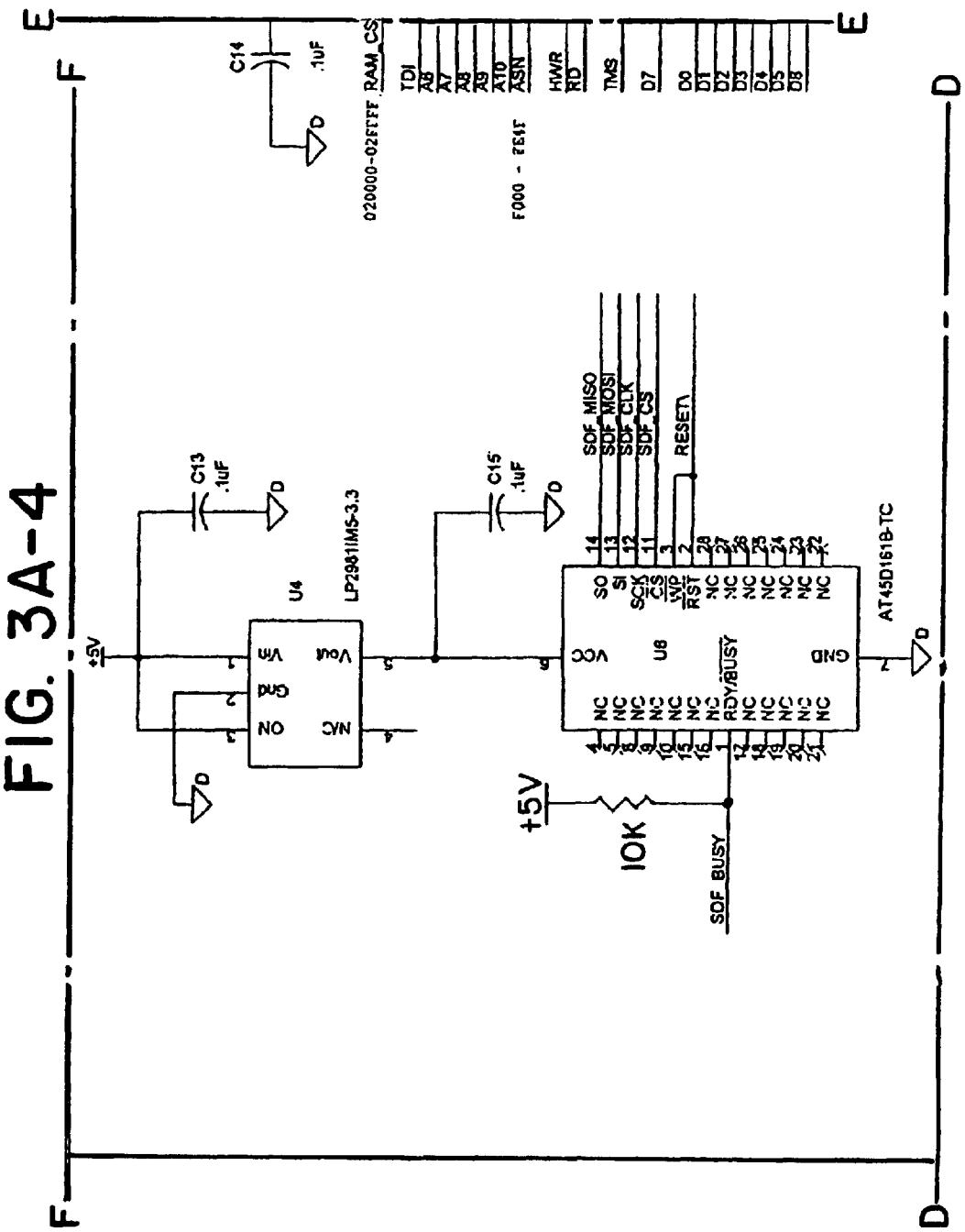

SYSTEM AND METHOD FOR PROCESSING ULTRASONIC SIGNALS

RELATED APPLICATIONS

The present invention is a continuation-in-part which relates to and claims priority of, U.S. patent application Ser. No. 10/292,799, filed on Nov. 12, 2002, now U.S. Pat. No. 6,707,762 entitled System for Heterodyning an Ultrasonic Signal, which is incorporated herein by reference in its entirety.

BACKGROUND OF THE INVENTION

1. Field of the Invention

The invention generally relates to the field of ultrasonic generators and, more particularly, to a system and method for processing heterodyned ultrasonic signals that are generated during valve inspections.

2. Description of the Related Art

It is well known that ultrasonic generators and detectors can be used to locate leaks or defects, e.g., in pipes. Such a system is shown in U.S. Pat. No. 3,978,915 to Harris. In that arrangement, ultrasonic generators are positioned in a chamber through which the pipes pass. At the ends of these pipes, exterior to the chamber, ultrasonic detectors are located. At the point where a leak occurs in the pipe or the pipe wall is thin, the ultrasonic energy will enter the pipe from the chamber and travel to the end of the pipe where the detector is located. The detector will receive an ultrasonic signal at the end of the pipe indicating the existence of the leak or weak spot in the pipe.

By locating an ultrasonic generator in a closed chamber, a standing wave pattern with peaks and nodes is established. If a node occurs at the position of a leak or weak spot, no ultrasonic energy will escape and the defect will not be detected.

Ultrasonic sensors have also been used to detect ultrasonic energy generated by friction within mechanical devices as disclosed in U.S. Pat. No. Re. 33,977 to Goodman, et al., the details of which are hereby incorporated herein, in their entirety, by reference. The greater the amount of friction, the greater the intensity of the generated ultrasonic energy. Applying a lubricant to the device reduces friction and consequently the intensity of the generated ultrasound drops. Measuring ultrasonic energy thus provides a way to determine when lubrication has reached the friction generating surfaces. Additionally, faulty devices, such as bearings, generate a higher level of ultrasonic energy than do good bearings and thus, this condition can also be detected. However, conventional means require two people to perform this procedure—one person to apply the lubricant to the device, and one person to operate the ultrasonic detector.

In certain instances, e.g., when detecting the malfunction of bearings, an ultrasonic detector is mechanically coupled to the casing of the bearings so that the vibrations caused by the malfunction can be mechanically transmitted to it. With such an arrangement, the frequency is not set by an ultrasonic generator, but is created by the mechanical vibration itself. Here, an ultrasonic detector circuit must be capable of sweeping over a band of frequencies to locate the one frequency that is characteristic of the malfunction. This is usually accomplished by a heterodyning circuit which can be tuned to various frequencies, much in the manner of a radio receiver.

Since ultrasonic energy used for these purposes is generally in the range of 40 kHz, it is too high in frequency to be heard by a human being. Thus, means are typically provided for heterodyning, or frequency shifting, the detected signal into the audio range, and various schemes are available for doing this.

Ultrasonic transducers generally produce a low voltage output in response to received ultrasonic energy. Thus, it is necessary to amplify the detected signal using a high-gain preamplifier before it can be accurately processed. However, if low cost heterodyning and display circuitry are to be used, means must be made available to attenuate the amplified signal to prevent saturating these circuits when high input signals are present. This attenuation also adjusts the sensitivity of the device. For a hand-held unit, the degree of attenuation should be selectable by the user. For example, U.S. Pat. No. 4,785,659 to Rose et al. discloses an ultrasonic leak detector with a variable resistor attenuator used to adjust the output level of an LED bar graph display. However, this attenuation method does not provide a way to establish fixed reference points to allow for repeatable measurements.

U.S. Pat. No. 5,089,997 to Pecukonis discloses an ultrasonic energy detector with an attenuation network positioned after an initial pre-amplifier and before the signal processing circuitry, which creates an audible output and an LED bar graph display. The resistors in the Pecukonis attenuation network are designed to provide an exponential relationship between the different levels of attenuation. However, Pecukonis does not heterodyne the detected signals to produce an audible output, but rather teaches the benefits of a more complex set of circuits which compress a broad range of ultrasonic frequencies into a narrower audible range. For many applications, the cost and complexity of this type of circuitry are not necessary.

When using ultrasonic energy to detect leaks, it is useful to have a portable ultrasonic sensor which indicates the presence and intensity of ultrasonic energy both visually and audibly. U.S. Pat. No. Re. 33,977 to Goodman et al. discloses an ultrasonic sensor that displays the intensity of the detected signal on an output meter operable in either linear or logarithmic mode, and also provides for audio output through headphones. U.S. Pat. No. 4,987,769 to Peacock et al. discloses an ultrasonic detector that displays the amplitude of the detected ultrasonic signal on a ten-stage logarithmic LED display. However, the detector disclosed in Peacock does not process the detected signal to produce an audible response, nor does it provide for signal attenuation after the initial pre-amplification stage.

Means have been proposed for increasing the output of the ultrasonic transducer. For example, in U.S. Pat. No. 3,374,663 to Morris it is suggested that an increase in the voltage output can be achieved by serially arranging two transducers. It has been found, however, that with such an arrangement a typical transistor pre-amplifier loads the transducers to such an extent that the gains achieved by stacking them serially are lost. The Morris patent proposes the use of a triple Darlington configuration in order to produce a sufficiently high input impedance to prevent this degradation in the signal produced by the stack of transducers. Unfortunately, the transducers in this arrangement are not placed so that they both readily receive ultrasonic energy. Thus, the Morris arrangement is not entirely satisfactory.

SUMMARY OF THE INVENTION

The present invention is directed to providing improved methods and apparatus for detecting leaks and mechanical faults by ultrasonic means. In accordance with the invention, an input transducer signal is applied to a unity gain buffer amplifier that is used to maintain the impedance level seen by the transducer. The processed signal from the unity gain buffer amplifier is supplied to a voltage control amplifier that also receives a voltage control signal that is generated by a digital-to-analog converter located on an external I/O board. The voltage control signal is used to switch the voltage controlled amplifier such that the dynamic range of the signal is expanded prior to a clip of the signal. The voltage control signal is based on a level that is programmed into the voltage control amplifier by the digital-to-analog converter located on the external I/O board. The voltage controller is thus controlled by the I/O board in response to commands sent to the external I/O board from a micro-controller.

The output from the voltage controlled amplifier is connected to a fixed gain differential amplifier. The output signal from the fixed gain amplifier is supplied to a variable gain amplifier that is switchable between two fixed levels, such as 0 dB and 20 dB. The gain level of the variable gain amplifier is toggled between the two fixed gain levels based on a level that is determined by the amount of gain that is programmed into the voltage control amplifier.

The output of the variable gain amplifier is supplied to a pair of heterodyning circuits, i.e., a dual heterodyning circuit. At each respective heterodyning circuit, the output signal from the variable gain amplifier is multiplied with a local oscillator signal that is internal to each circuit. Here, each local oscillator is nominally set to 38 kHz such that for a 40 kHz input transducer signal, a difference frequency of about 2 kHz (i.e., the audio component) is provided at the output of each heterodyning circuit.

The output signal from the first heterodyning circuit is amplified and divided into two signal branches. The first signal branch is transformer coupled to a headphone output. The second signal branch is connected to an amplifier that is also transformer coupled to a line output and also applied to an external audio amplifier. The output from the second of the heterodyning circuits is amplified and supplied to a metering circuit.

In addition, a further analog signal path is created at the second heterodyning circuit. The signal in this path is converted to a linear dB format analog signal and supplied to a micro-controller. This analog signal is converted in the micro-controller into a digital signal by an analog-to-digital converter, and is further converted in the micro-controller into a WAV file format, as well as other digital signal formats, for subsequent spectral analysis.

The present inventors have determined that a heterodyned signal that drives a meter requires a relatively large dynamic range, but a limited frequency response, while a heterodyned signal that is required for headphones or spectral analysis may have a low dynamic range, but requires high resolution. Further, it has been found that the resolution or frequency response of the input transducer signal is degraded if a single heterodyning circuit is used to drive a number of circuits or meters with competing requirements. In order to overcome these competing requirements, the present invention uses a dual heterodyning circuit in which the two individual heterodyne circuits are separately optimized so that the second results in a signal with a large dynamic range and the first results in a signal with a great resolution, and neither unduly loads the transducer array or obscures subtle frequency components. This permits the capture of particularly low level frequency components for extraction during spectral analysis.

In accordance with the invention, the first heterodyning circuit has a feed back loop filter and a transformer to provide an enhanced spectral (i.e., frequency) response. This circuit is used to drive the headphone, a wave file generator and a line output. This signal, which has a modest dynamic range but a high frequency response and a low signal to noise ratio, allows the spectrum of the signal to be analyzed in real time by an external spectrum analyzer, recorded for later analysis or listened to in real time through the headphones.

The second heterodyning circuit has a smaller frequency response but a larger dynamic range so that it can drive the meter. In accordance with the invention, the second heterodyne circuit is not required to have an optimized spectral response. If the meter were driven with the first heterodyne circuit, the impedance and dynamic range requirements of the meter would adversely affect the response. Thus, two heterodyne circuits are used, with the circuit that drives the meter being simpler, and less costly to manufacture and having a larger dynamic range.

In either mechanical analysis or electrical equipment analysis, a large number of frequencies in the low frequency range become lost. This is especially true in the case of electrical applications. After extended use of the detection equipment, operators often tend to begin to use their ears as a guide to the condition of an area of concern. However, it is extremely difficult for a person to discern with their ears the differences between inputs that are electrical in nature and inputs that are vibrational. Further, in other technologies, such as vibration analysis, infrared technologies, or where rotational equipment is used, the use of the human ear is a highly unreliable way in which to predict faults. For example, a transformer resonating at 60 Hz may cause a component in an equipment cabinet to resonate at the same 60 Hz. When an operator listens to the cabinet containing the component that is vibrating at the 60 Hz, it is impossible to determine whether the resonance is electrical or mechanical.

Typically, on/off valves are checked for their position, e.g., open or closed, or for leakage in the closed position. By way of a contact module, such valves can be tested using the portable ultrasonic device of the present invention. Contact modules are generally used to detect structure borne ultrasound. Transducers are contained in the module, and a rod is attached to the ultrasonic device. The rod acts as a waveguide that conducts ultrasound to excite the transducers to generate a signal that the ultrasonic device can measure.

A high level of confusion occurs when checking valves for leaks or "bypassing" caused by turbulent flows, either upstream or downstream from the valve in question. When measurements are performed at a distance from the valve, confusion can arise because an operator is unable to determine whether the valve is good or bad. This occurs because the operator is unable to distinguish between problems that occur at the remote location and those which occur at the valve itself. In addition, if the user only checks the upstream and downstream sides of a valve, then confusion may arise because they may believe the valve is "bypassing" and thus, change the valve. A valve is bypassing if fluid (gas or liquid) passes through the valve when it is closed.

If the operator falsely concludes that the downstream reading is higher than the upstream reading, which is usually indicative of a leaking valve, the confusion caused can be extensive in terms of the time and cost for replacing a valve that is not defective and is not the source of the potential problem. The actual source of the higher reading for the upstream side of the valve can originate from turbulence generated further down the piping from the valve, such as from turbulence caused by a right angle connection or even from a partial blockage of the pipe. The method of the present invention eliminates such confusion associated with checking valves by adding additional test points with which to ensure verification of the actual source of leaks or turbulence.

In accordance with the method of the invention, this is achieved by establishing a base line measurement for each valve under test. The ultrasonic sound at multiple points upstream and downstream from the valve is measured. In the preferred embodiment, the ultrasonic sound at two upstream points and two downstream points is measured. Prior to performing all measurements, a visual inspection of the valve is performed to confirm that the valve is closed or in the off position.

The measurement of the ultrasonic sound at the first upstream point is then made at a distance located X times the pipe diameter from the valve. The measurement of the ultrasonic sound at the second upstream point is made at a point located directly upstream of the valve, approximately at the pipe fitting. The two downstream measurement points are at a distance of equal relationship to the upstream test point, i.e., the first downstream measurement point is located at a distance located X times the pipe diameter from the valve, and the second downstream measurement point is located directly downstream of the valve, approximately at the pipe fitting. In the preferred embodiment, X is six (6), i.e., the first measurements are located at a point that is 6 times the diameter of the pipe away from the valve.

While touching the contact module to a measurement point to measure the ultrasonic energy at the two upstream points, the sensitivity of the dual heterodyning circuit is adjusted by turning a rotary knob on the rear of the portable device so that a liquid crystal display, also on the rear of the portable ultrasonic device, displays the dB value of the ultrasonic measurements. These initial upstream ultrasound values establish baseline measurements for the valve. The value of the ultrasonic sound at the first and second upstream points should be close to each other. In some circumstances, the second measured ultrasonic value can be slightly lower than the first measured ultrasonic value. In contemplated embodiments, the second measurement is performed without re-adjusting the sensitivity of the dual heterodyne circuit.

The level of the ultrasound at the two downstream points is then measured. The value of the ultrasound at the first downstream test point is compared to the values of the ultrasound at the upstream test points. The value of the ultrasound at the second downstream test point is measured to ensure that no ultrasonic sound is emanating downstream from the valve. If the value of the ultrasonic sound measured at the second downstream point is greater than the value of the ultrasonic sound measured at the first downstream point, then this ultrasonic sound must be "tuned out" or "shut off" to obtain a proper test of the valve. When it is not possible to tune out or shut off a downstream structure borne ultrasound, it is necessary to locate the source of the highest reading to determine its effect on the outcome of the measurements.

In accordance with the embodiments of the invention, additional ultrasound measurements further downstream are performed to assist in locating/confirming the source of the ultrasound. Hence, if the values of the ultrasound at the downstream points are higher than the values of the ultrasound at the upstream points, the valve is leaking. On the other hand, if the values of the ultrasound at the downstream points are close to or lower the values of the ultrasound at the upstream points, then the valve is not leaking, i.e., the valve is good.

By using the dual heterodyning circuit of the present invention to provide the enhanced spectrum, it becomes clear whether a detected resonance is mechanical or electrical. In addition, fault frequencies are also more easily discernible. In other words, the enhanced signal output provides a lower signal-to-noise ratio, so as to increase the ease with which frequency components are analyzed. In addition, the method of the invention eliminates the unnecessary replacements of "good" valves, which can be expensive in certain environments, such as in a nuclear plant or on a ship, where the valves are welded into place.

BRIEF DESCRIPTION OF THE DRAWINGS

The foregoing and other advantages and features of the invention will become more apparent from the detailed description of the exemplary embodiments of the invention given below with reference to the accompanying drawings in which:

FIGS. 2A-1 through 2K-2 form a schematic diagram of the dual heterodyning circuit shown in FIGS. 1A-1 and 1A-2;

DETAILED DESCRIPTION OF AN EXEMPLARY EMBODIMENT

Figure 3A:
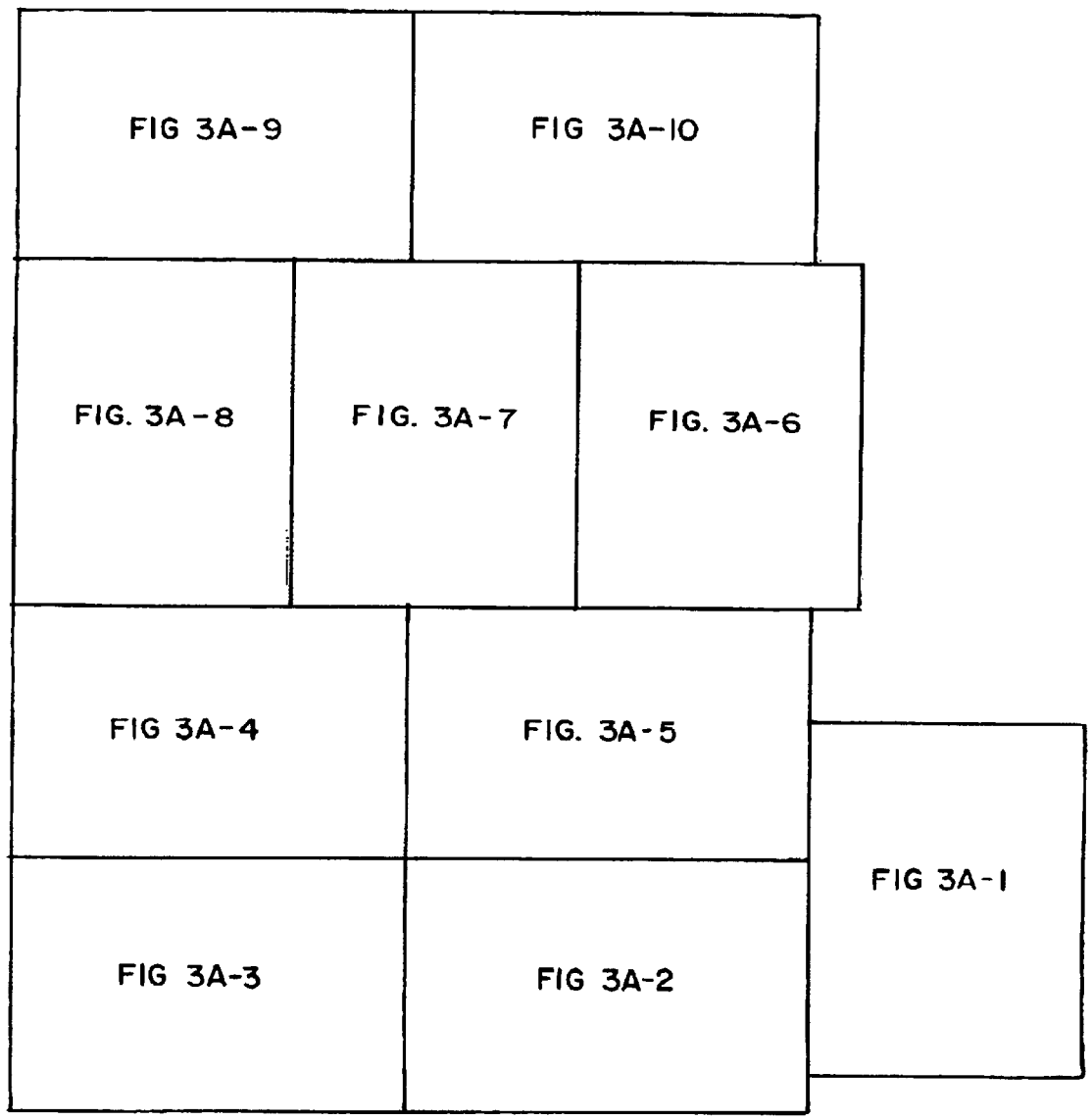
FIG. 3A through FIG. 3B-9 form a block diagram of the I/O board, the micro-controller, and the rear panel in accordance with the invention.
Figures 2, 3A:
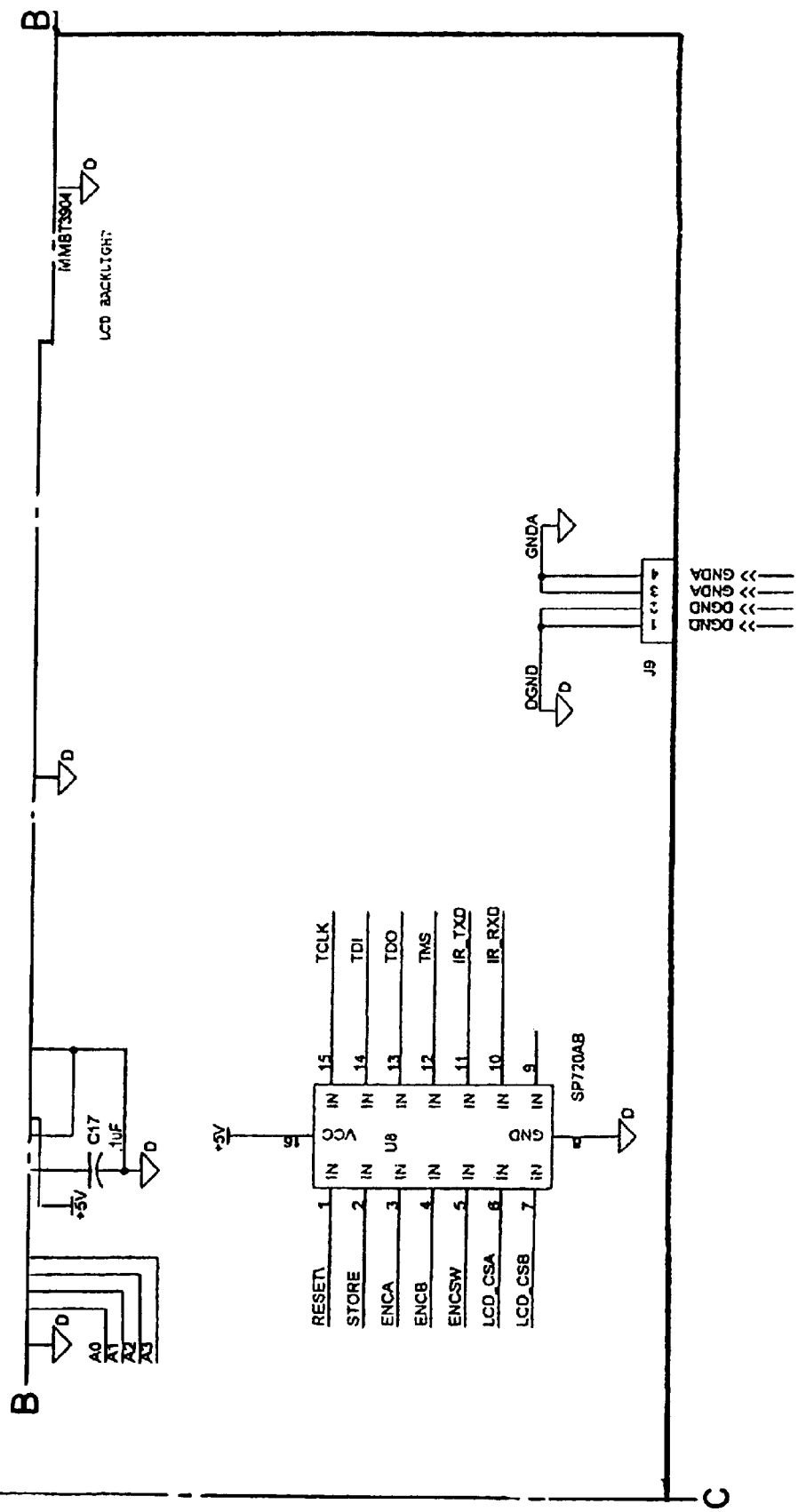
Figures 3, 3A:
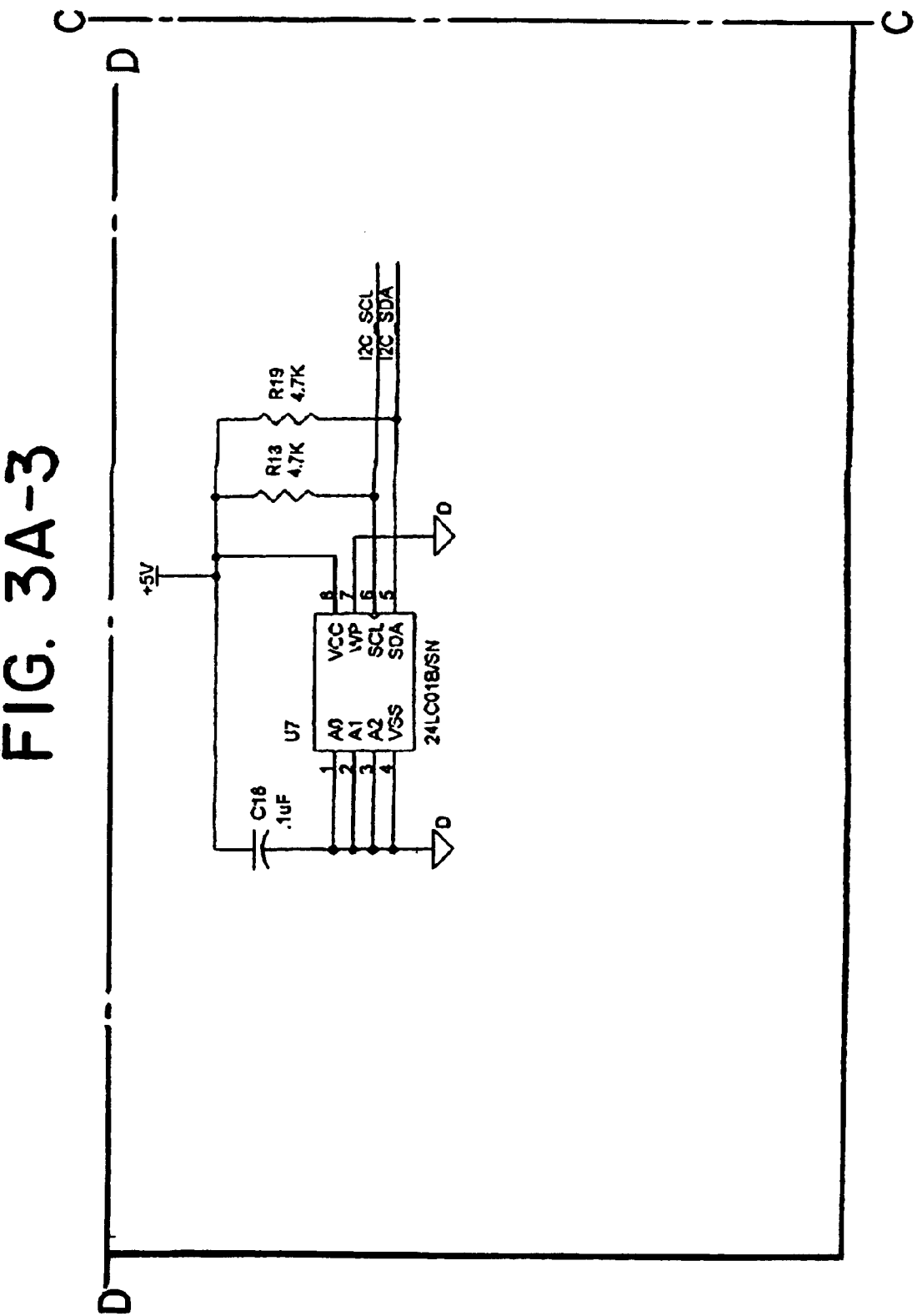
Figures 3, 3A, 4, 5:
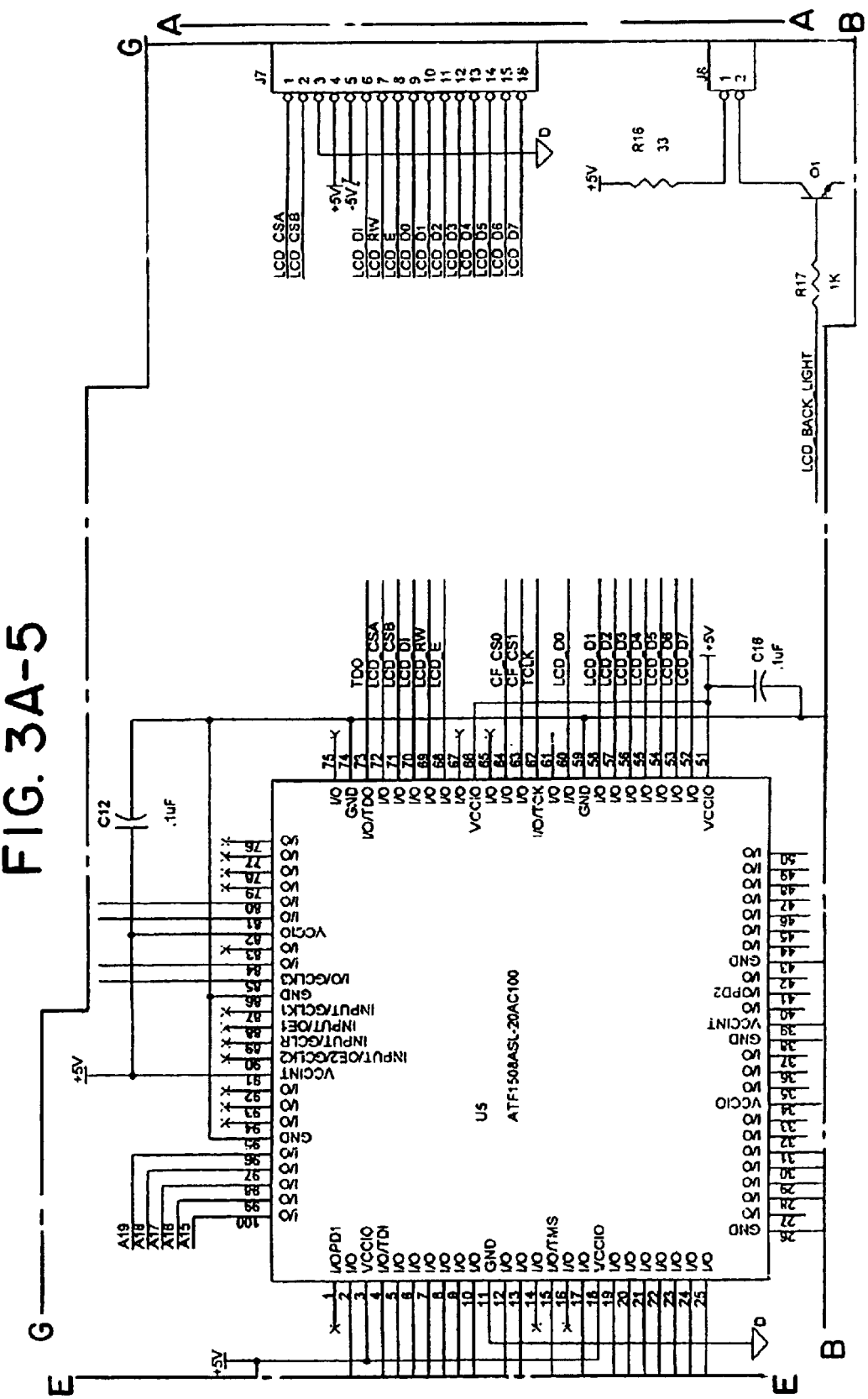
Figures 3, 3A, 4, 5, 6:
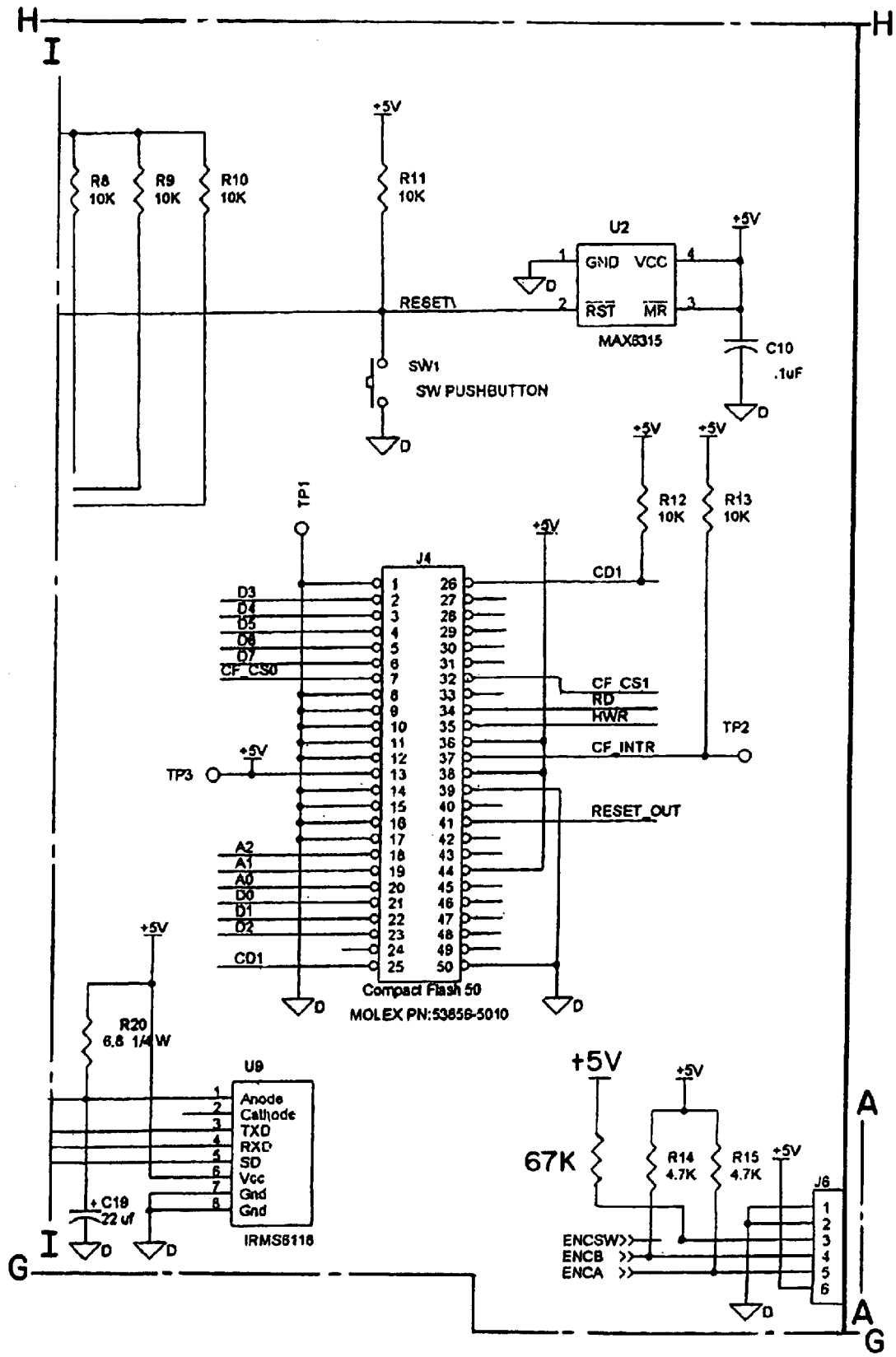
FIG. 6 is a perspective view showing the flash card and rear panel of the ultrasonic instrument of the invention.

FIG. 6 is a perspective view of a portable ultrasonic detector 600. Toward the front of the housing there are ultrasonic transducers 95, as shown in FIG. 8. Microprocessor controlled circuits for heterodyning the ultrasonic signal to shift its frequency to the audio range are contained in the body of the housing. A display 82 is located at the back so the operation and the results can be viewed. At the back, there is also a jack 88 for headphones, so that the user can listen to the audio sound during a test, e.g., as a way of locating a leak. Other jacks and controls are located on the body or will be described subsequently.

Figures 1, 1A:
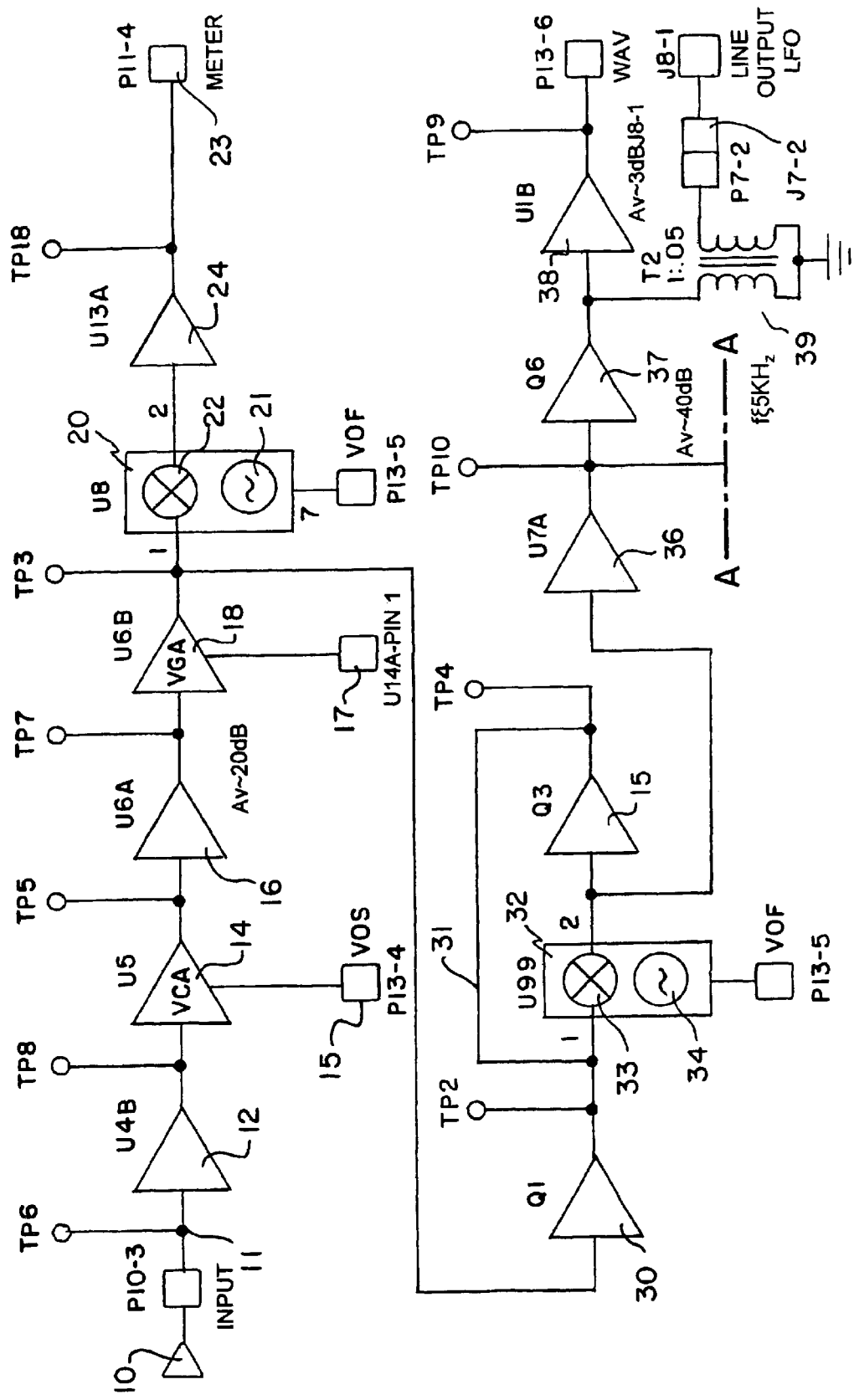
FIGS. 1A-1 and 1A-2 form an exemplary block diagram of the dual heterodyning circuit in accordance with the present invention.
Figures 1, 1A, 2:
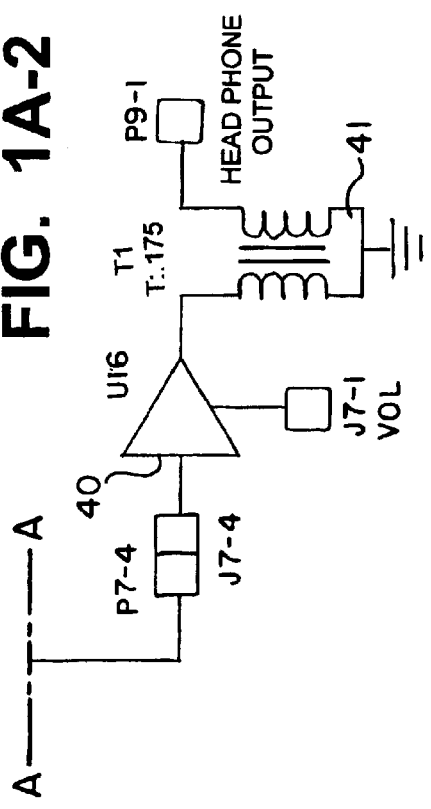
Figure 4:
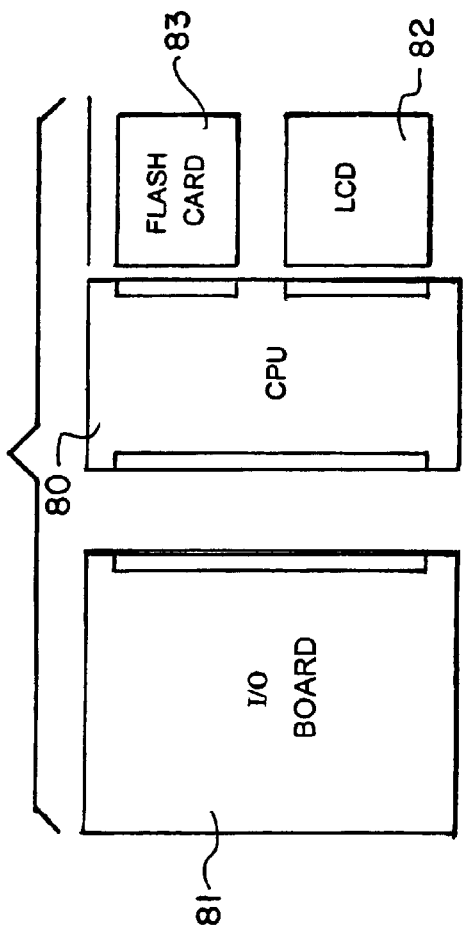
FIG. 4 is a block diagram illustrating a flash card inserted into the micro-controller of FIG. 3(a)

FIGS. 1A-1 and 1A-2 form an exemplary block diagram of the dual heterodyning circuit in accordance with the present invention which is located in the housing of the ultrasonic detector. In FIG. 1A-1, an input signal is applied from an ultrasonic transducer to a buffer amplifier 12(U4B) at input 11(P10). Typically, unity gain buffer 12 is used to maintain at a desired level the impedance level seen by the transducer. The processed signal from buffer 12 is supplied to voltage controlled amplifier (VGA) 14 (U5) that also receives a voltage control signal 15 that is generated by a digital-to-analog converter on an external I/O board shown in FIGS. 3A thru 3B-9. The voltage control is thus controlled by the I/O board in response to commands sent to the external I/O board from a micro-controller (see FIGS. 3A thru 3A-10).

Voltage controlled amplifier 14 is connected to a fixed gain amplifier 16. In preferred embodiments, amplifier 16 has a fixed gain of approximately 20 dB. The output signal from amplifier 16 is supplied to variable gain amplifier 18 (VGA) that is switchable between two fixed levels, such as 0 dB and 20 dB. The gain level of amplifier 18 is toggled between the two fixed gain levels based on a signal level applied to input 17. This signal is determined at the micro-controller on the I/O board based on the amount of gain that is programmed into the voltage controlled amplifier 14.

The output of VGA 18 is supplied to a first heterodyning circuit 20 (U8). In heterodyne circuit 20, the output signal supplied to VGA 18 is multiplied in multiplier 22 by a local oscillator 21 that is internal to heterodyne circuit 20. Sum and difference frequencies are provided at the output of circuit 20. At this point, the high frequency components of the signal are filtered out and a difference signal is buffered in amplifier 24, such that an audio signal is provided. The local oscillator 21 within circuit 20 is nominally set to 38 kHz such that for a 40 kHz input transducer signal, a difference frequency is approximately 2 kHz. Amplifier 24 is used to amplify the output signal and apply it to terminal 23 which leads to a metering circuit (not shown). This signal has a large dynamic range.

The output signal from VGA 18 is also received by amplifier 30, which amplifies this signal prior to supplying it to a second heterodyning circuit 32. In exemplary embodiments, the signal supplied to amplifier 30 is amplified by approximately 10 dB. The second heterodyne circuit 32 receives the output of amplifier 30 and multiplies this signal in multiplier 33 by a local oscillator 34 that is also internal to circuit 32. Sum and difference frequencies are created at the output of heterodyne circuit 43. The high frequency components of the signal are filtered out and the low frequency signal is buffered in amplifier 35, such that an audio signal is provided. The local oscillator within circuit 32 is nominally set to 38 kHz such that for a 40 kHz input transducer signal, a difference frequency audio signal is approximately 2 kHz. The audio signal is then buffered by a unity gain amplifier 36. The output of amplifier 36 is next provided to an amplifier 37. In preferred embodiments, the signal level supplied to amplifier 37 is increased by approximately 40 dB.

In accordance with the invention, the second heterodyning circuit 32 has a feed back loop 31 from the output of amplifier 35 to the input of circuit 32. This feedback loop 31 provides an enhanced spectral (i.e., frequency) response.

The output signal from unity gain amplifier 36 is divided into two signal branches. The first branch leads to the amplifier 37. The second branch leads from unity amplifier 36 to amplifier 40 that is coupled to a headphone output by way of transformer 41. In the first signal branch, amplifier 37 is coupled to transformer 39, which in turn is coupled to a line output. The line output is subsequently applied to an audio amplifier (not shown). In addition, a further analog signal from amplifier 37 is coupled to amplifier 38, where it is attenuated by approximately −3 dB. The attenuated signal is then supplied to the micro-controller (not shown). This analog signal is converted in the micro-controller into a digital signal by an analog-to-digital converter, and is further converted in the micro-controller into a WAV file format, as well as other digital signal formats for storage and playback, and for subsequent spectral analysis.

The wideband, high resolution signal from amplifier 36, which is a result of feedback loop 31, is used to drive the headphone, a wave file generator and a line output. This signal, which has a modest dynamic range but a high frequency response and a low signal to noise ratio, allows the spectrum of the signal to be analyzed in real time by an external spectrum analyzer, recorded for later analysis or listened to in real time through the headphones.

The first heterodyning circuit 20 has a smaller frequency response but a larger dynamic range so that it can drive the meter. In accordance with the invention, the first heterodyne circuit is not required to have an optimized spectral response. If the meter is driven with the same heterodyne circuit as the headphone circuit, the impedance and dynamic range requirements of the meter would adversely affect the headphone response. Thus, two heterodyne circuits 20, 32 are used, with the circuit that drives the meter being simpler, less costly to manufacture and having a greater dynamic range. The circuit that drives the headphones has a smaller and a lower signal-to-noise ratio, which provides a better spectral response.

Figures 1, 2A:
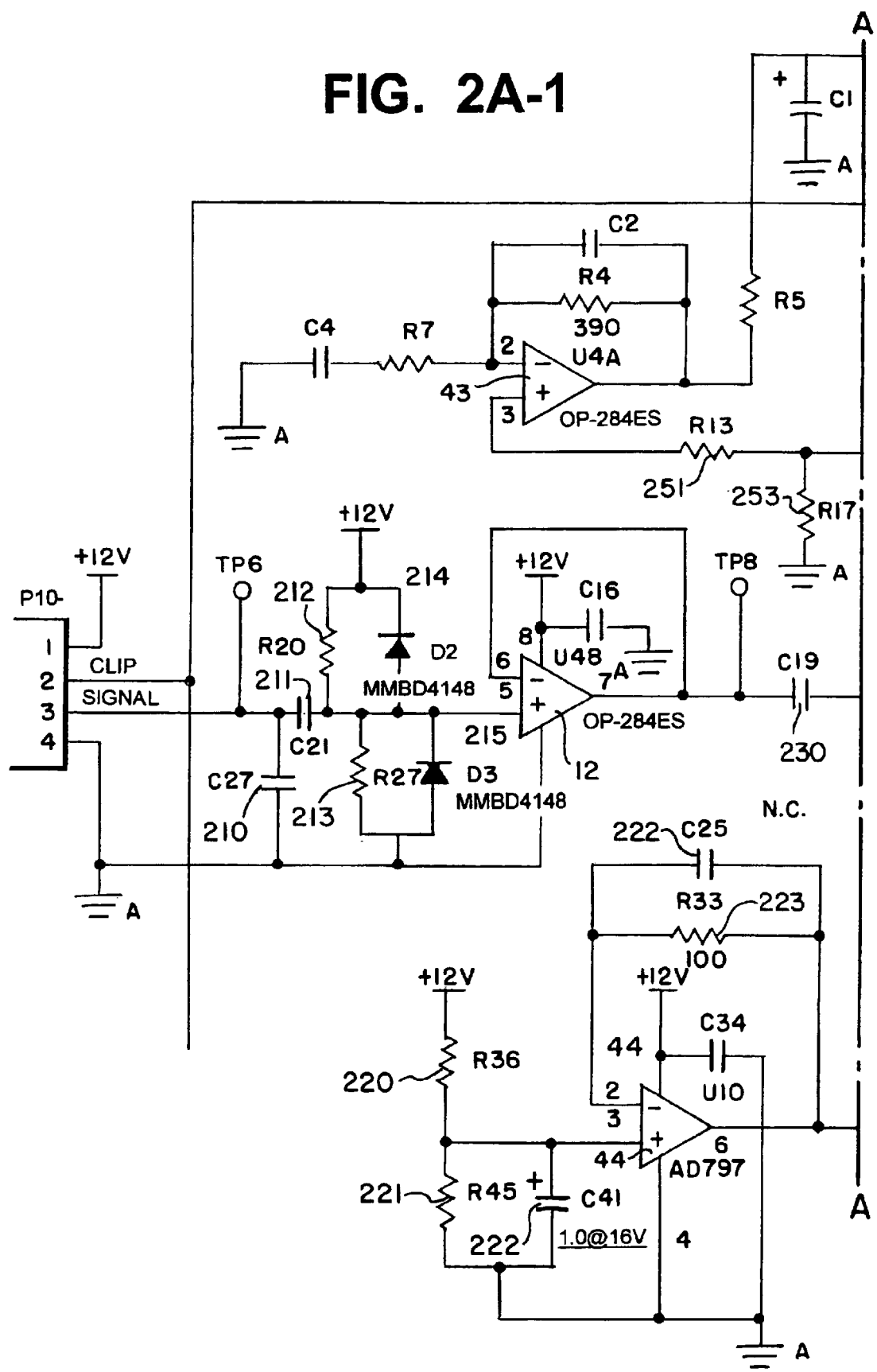
Figures 2, 2A:
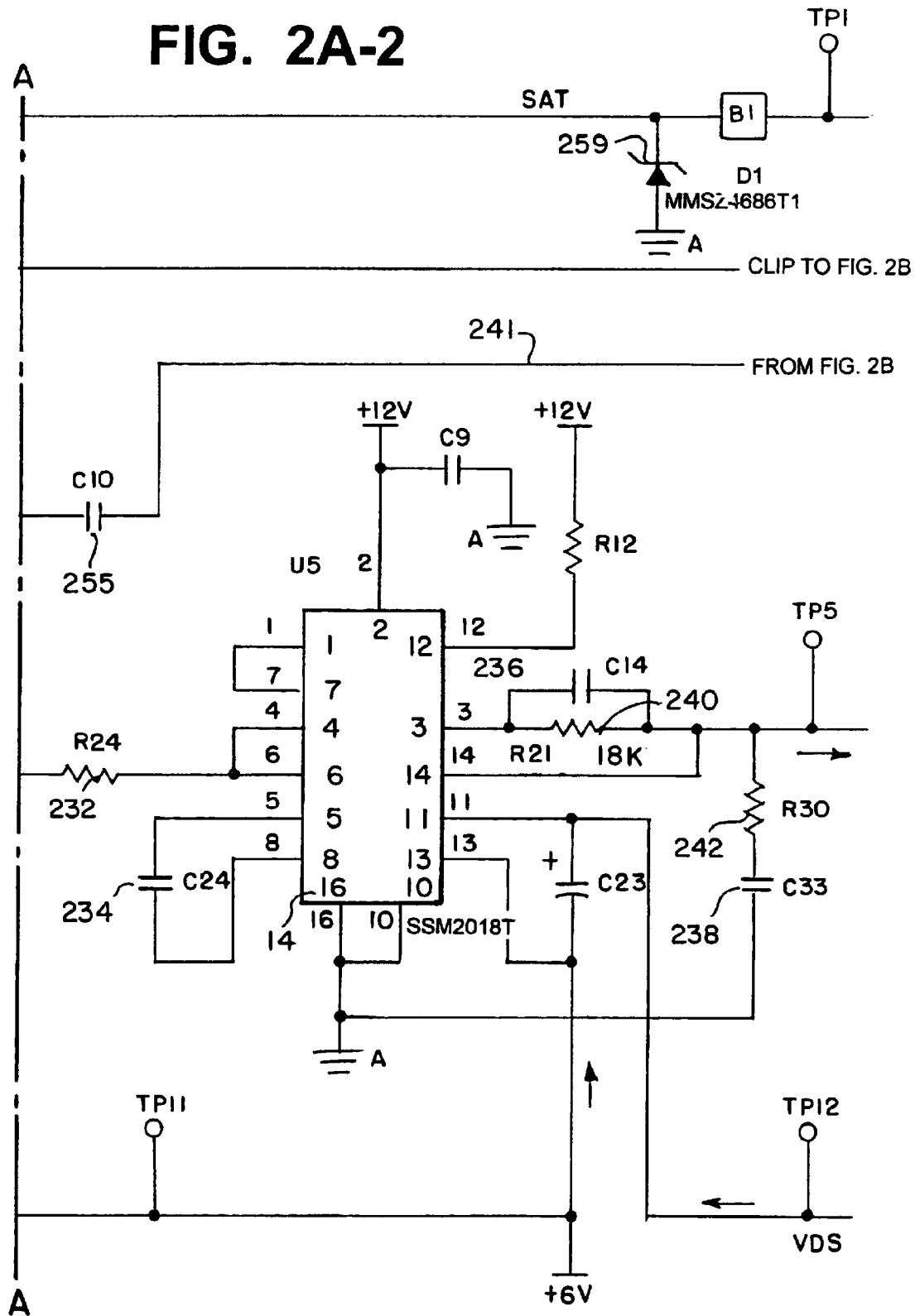

By way of example, FIGS. 2A-1 thru 2K-2 Form an exemplary schematic diagram of the dual heterodyning circuit in accordance with the present invention. Buffer amplifier 12 is shown in FIG. 2A-1. A transducer signal having a frequency of approximately 40 kHz±5 kHz is applied via connector 11 (P10) by way of capacitors 210 (C27) and 211 (C21), resistors 212 (R20) and 213 (R27), diodes 214 (D2) and 215 (D3) to the buffer amplifier 12, which is used to maintain the impedance level seen by an input transducer (not shown) at a predetermined fixed level. Typically, amplifier 12 is a standard Integrated Circuit (IC), such as an OP-284ES.

The voltage divider comprising resistors 220 (R36) and 221 (R45), along with capacitor 222 (C41) are coupled to the positive input of amplifier 44 (U10) that is used to generate a 6 volt low impedance output based on the 12 volt input that is applied to resistor 220. The 6 volt low impedance output is used to provide a reference level for the analog circuitry of the invention. Amplifier 44 has a feed back loop comprised of capacitor 222 (C25) and resistor 223 (R33) to improve its response. This amplifier is typically a standard "off-the-shelf" IC, such as an AD797 manufactured by Analog Devices.

Capacitor 230 (C19) and resistor 232 (R24) are connected in series from the output of amplifier 12 to the input of voltage controlled amplifier (VCA) 14 (U5). Amplifier 14 with capacitors 234 (C24), 236 (C14), 238 (C33), resistors 240 (R21), 242 (R30) provide expanding the dynamic range of the signal prior to clipping of the signal. Preferably, VGA 14 is a standard voltage controlled amplifier, such as a SSM2018T manufactured by Analog Devices. The control voltage on pin 11 of VCA 14 is generated by a digital-to-analog convertor 71 (DAC) that resides on an I/O board (shown in FIG. 3B-3) that is controlled by an external micro-controller (shown in FIGS. 3A-1 thru 3A-10). VOS 302 is the control signal (FIGS. 1A-1). The output of VGA 14 is on pin 3 through capacitor 236 and resistor 240 (TP5).

Figure 2B:
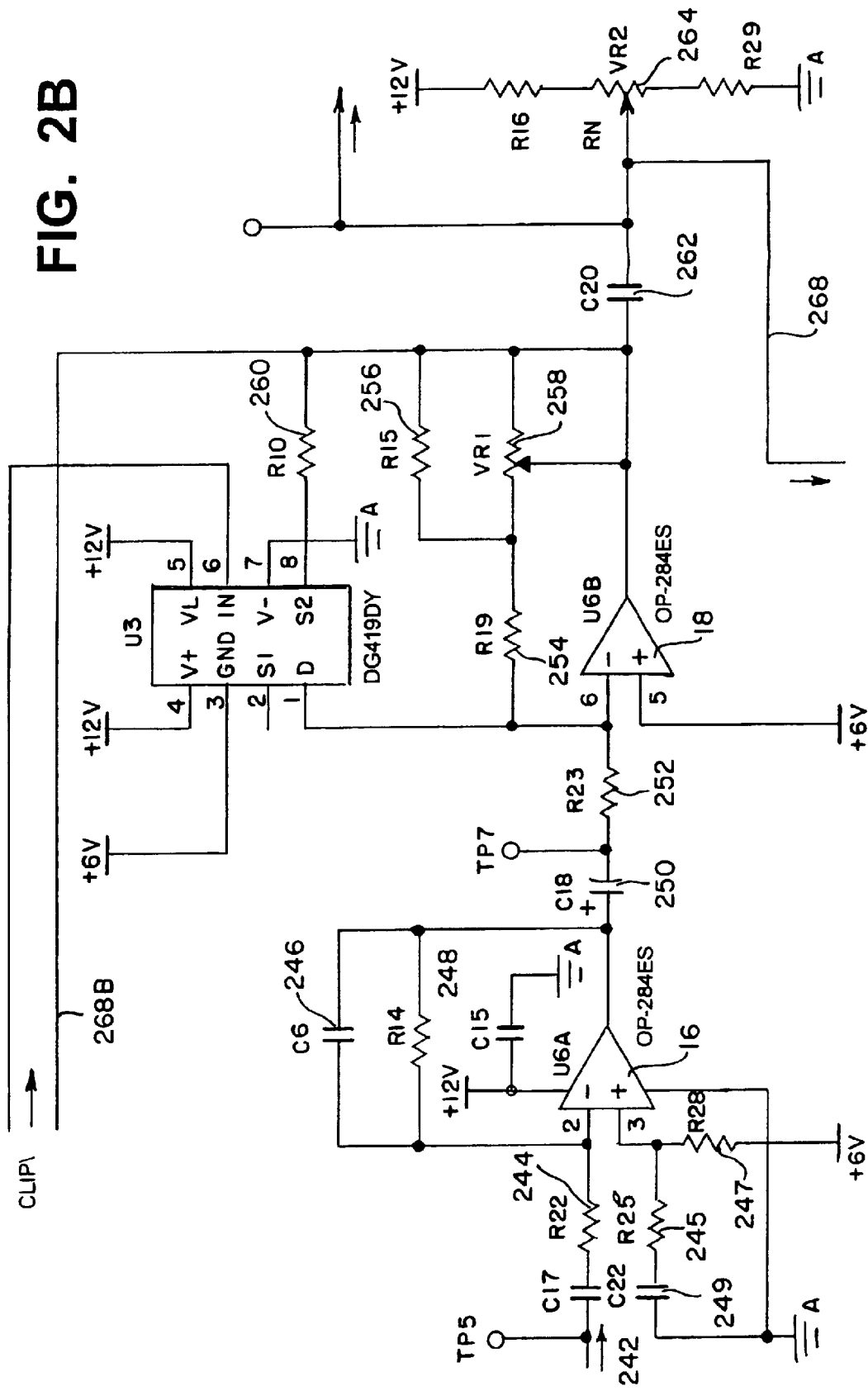

As shown in FIG. 2A-2 and 2B, the output of VCA 14 on TP5 is applied to the input of the differential amplifier 16 through capacitor 242 and resistor 244. A feed back loop of capacitor 246 and resistor 248 is connected around amplifier 16. Capacitor 249 and resistors 245, 247 form the rest of the differential amplifier 16. Amplifier 16 has a predetermined fixed gain level and because of its high common mode rejection ratio noise is reduced. The output signal from amplifier 16 is coupled to the input of variable gain amplifier 18 by way of capacitor C18 and resister R23. In preferred embodiments, amplifier 16 is typically a standard "off-the-shelf" IC, such as an OP-284ES, and has a gain level of approximately 20 dB.

Amplifier 18 is switchable between two gain levels based on the sensitivity level required by VCA 14. In preferred embodiments, amplifier 18 is switched between 0 dB and 20 dB by an analog switch 45 (U3) that is typically a standard "off-the-shelf" IC, such as a DG419DY. Resistor 254 (R19), resistor 256 (R15) and variable resistor 258 (VR1) set the gain, while resistor 260 when shorted across the other resistor by switch U3 sets the second gain level. The output of amplifier 18 is connected through capacitor 262 (C20) to the output at TP3. This level is biased by a voltage from variable resistor 264 (VR2).

Figure 2C:
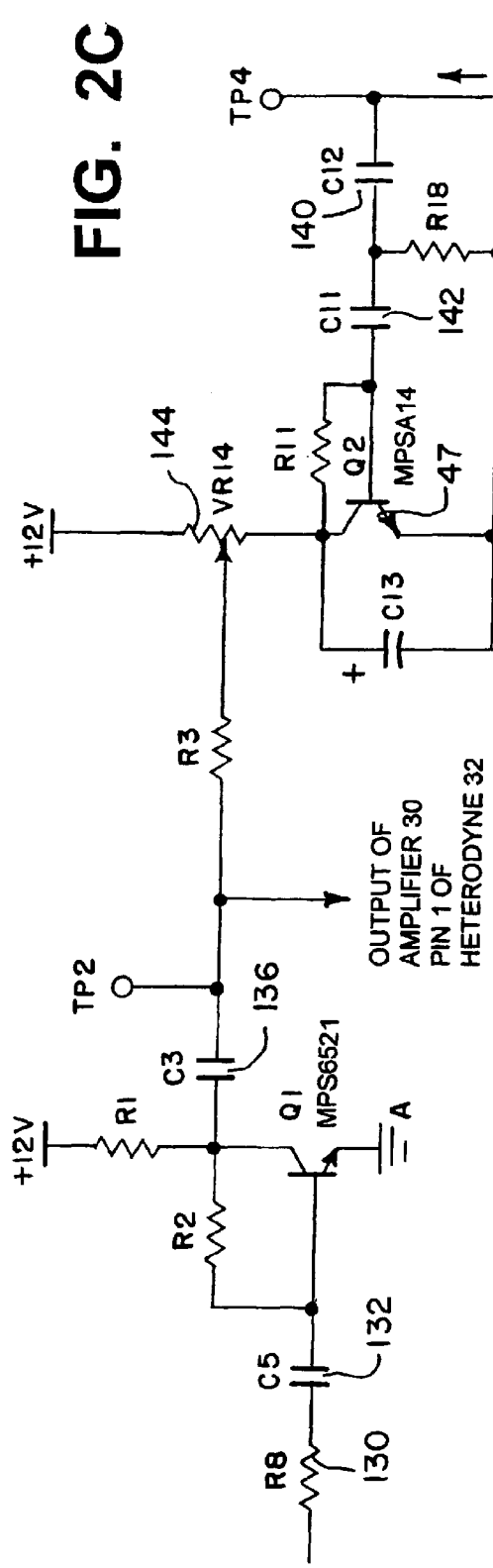
Figure 2D:
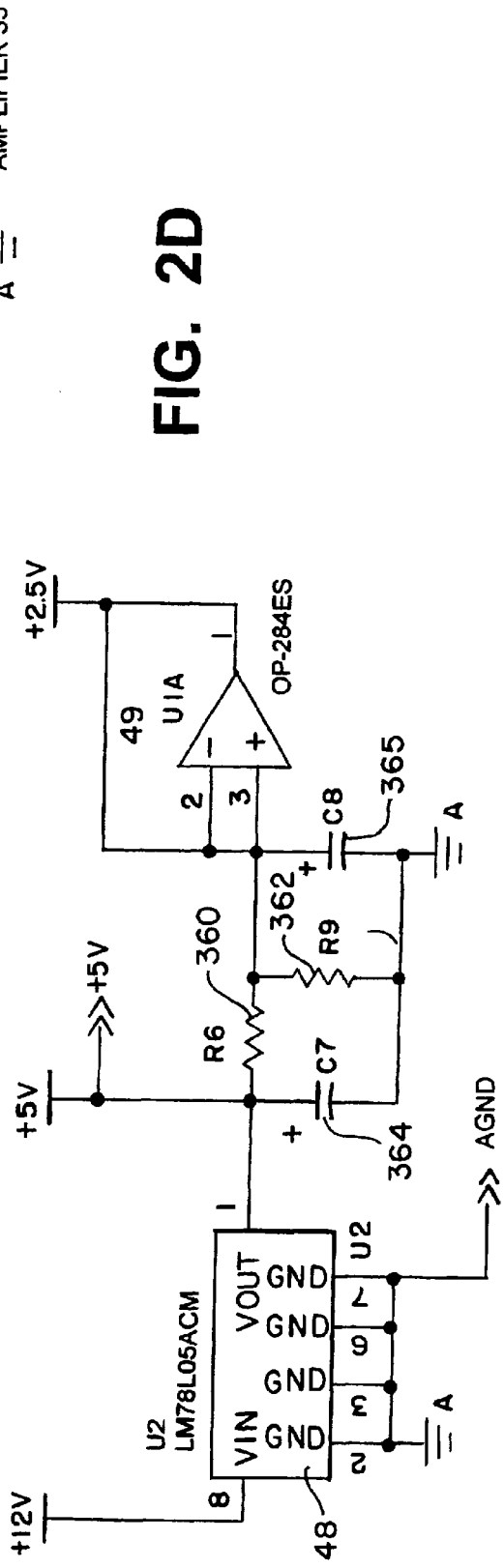
Figure 2E:
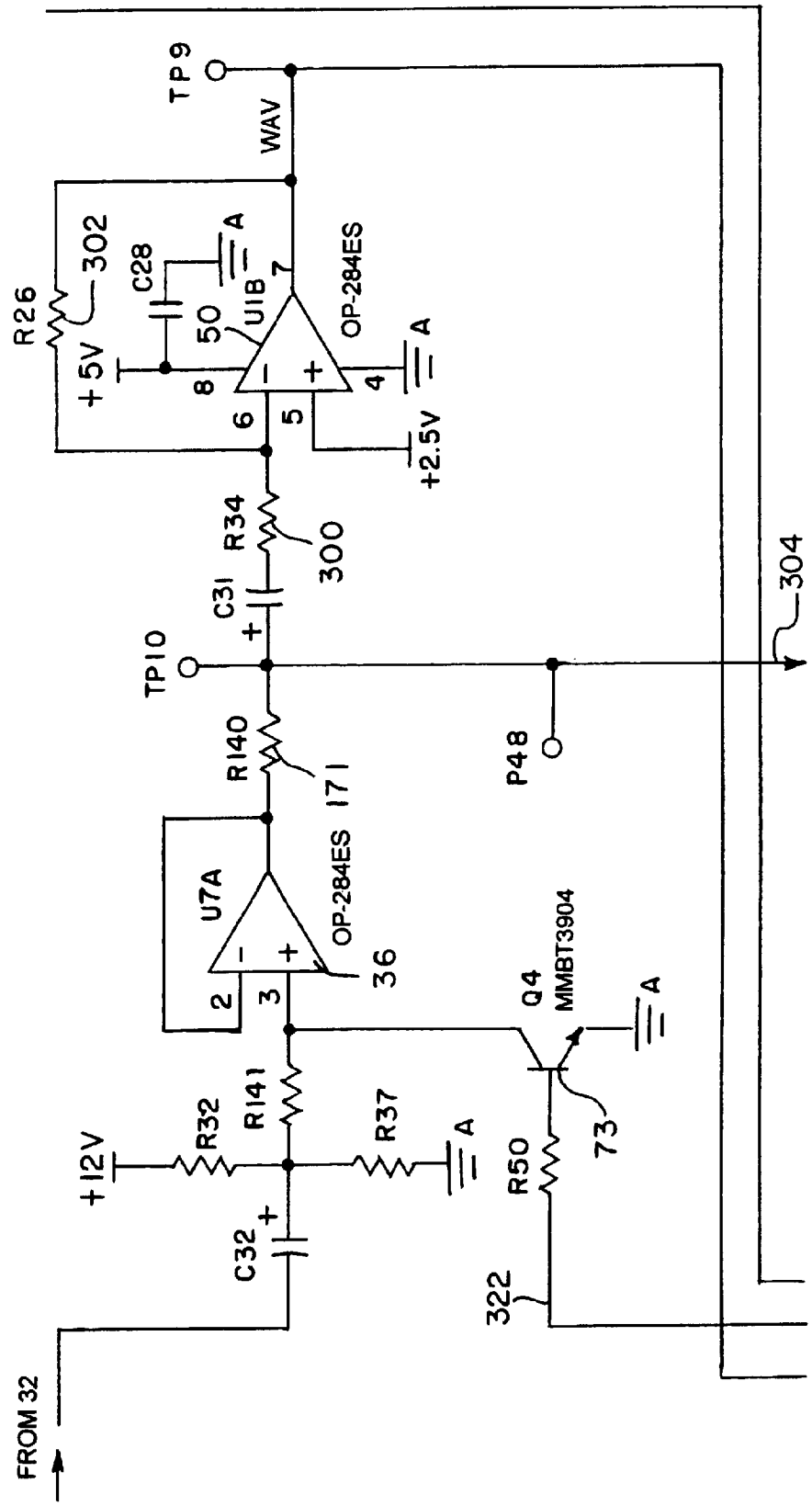

The micro-controller sets the digital bits DAC, CLK, DACSDO, DACLD on connector J3 (FIG. 3A-8). These bits are applied to DAC 71 (FIG. 3B-3), which in turn produces the control voltage 302 (VOS or VOF) on J13. A control voltage 302 VOS is received on P13 (FIG. 2H-2). As shown in FIG. 2G-2, VOS is then supplied to amplifier 52 (U11A) by way of resistors 270 (R57) and 272 (R58) to amplifier 57 by way of resistor 274 (R83). The output of amplifier 52 is provided to one input of differential amplifier 53. A unity gain buffer amplifier 55 has an input voltage from variable resistor 276 (VR7). Its output is applied to the other input of amplifier 53 as a reference voltage. The output of amplifier 53 is amplified in amplifier 54 and provides the signal at TP12. In effect, the amplifiers 52, 53, 54 and 55 scale and level shift the VOS signal. As can be seen from FIG. 2A-2, the TP12 signal is applied to the control output of VCA 14.

The VOS signal level is from approximately 0 to 5 volts. In preferred embodiments, the signal level of VOS is from 0 to 4.095 volts.

In alternative embodiments, variable resistor 280 (VR8) RT1, and RG1 (FIG. 2G-2) are optionally connected for providing nominal temperature compensation of the system.

Amplifier 57, which also receives the VOS signal, buffers that signal and feeds the positive input (pin 3) of amplifier 56 (U14A) through resistor 284 (R82), where amplifier 56 is connected in a comparator arrangement. Here, resistor 286 (R84) is used to provide hysteresis for noise rejection. Coupled to the negative input (pin 2) of amplifier 56 is a variable reference level that is created by variable resister 288 (VR9), which sets a reference level. Typically, amplifiers 52, 53, 54 and 55 are standard "off-the-shelf" ICs, such as a LM6134AIM.

In accordance with the invention, the reference level that is applied to the negative input (pin 2) of amplifier 56 is set during a calibration process to generate a CLIP signal that is output from pin 1 of amplifier 56. This CLIP signal is used to switch the variable gain amplifier 18 from 0 dB to +20 dBs. (See the input switch to switch 45 on FIG. 2B.) Simultaneously, the gain of the transducer pre-amps (not shown) is decreased by 20 dB. Of note, in order to extend the dynamic range of the transducer amplifier (not shown), the overall gain of the system plus the transducer pre-amp must have no net increase in gain. As a result, if the variable gain amplifier in the pre-amp located within the transducer has a 100 dB dynamic range and a pad of 20 dB is inserted, then a clean, un-clipped dynamic range of 120 dB is achieved from the entire system. The signal that controls the switching of amplifier 18 is the CLIP signal that is generated by amplifier 56.

Figure 5:
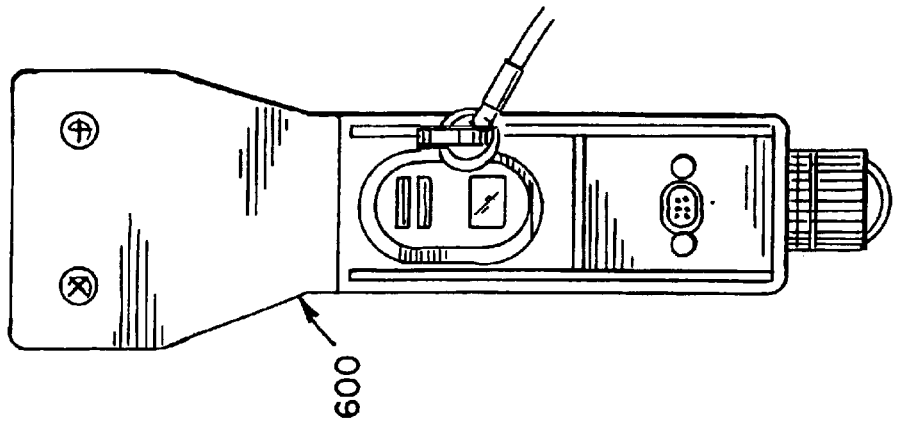
FIG. 5 is a bottom view of the ultrasonic instrument of the present invention.
Figures 3, 3A, 4, 5, 6, 7:
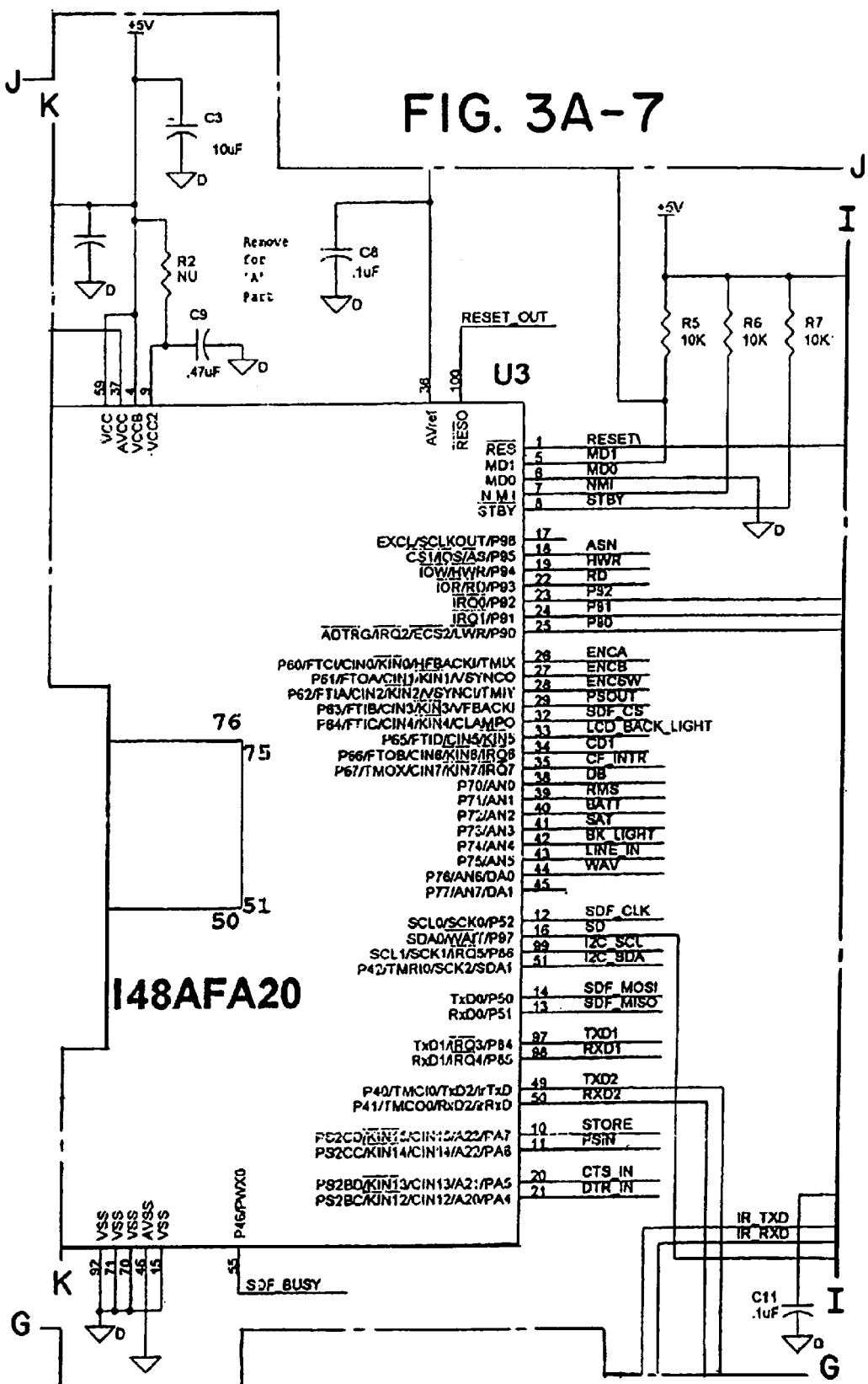
FIG. 7 is a plan view of the rear panel of the ultrasonic instrument of the invention.
Figures 3, 3A, 4, 5, 6, 7, 8:
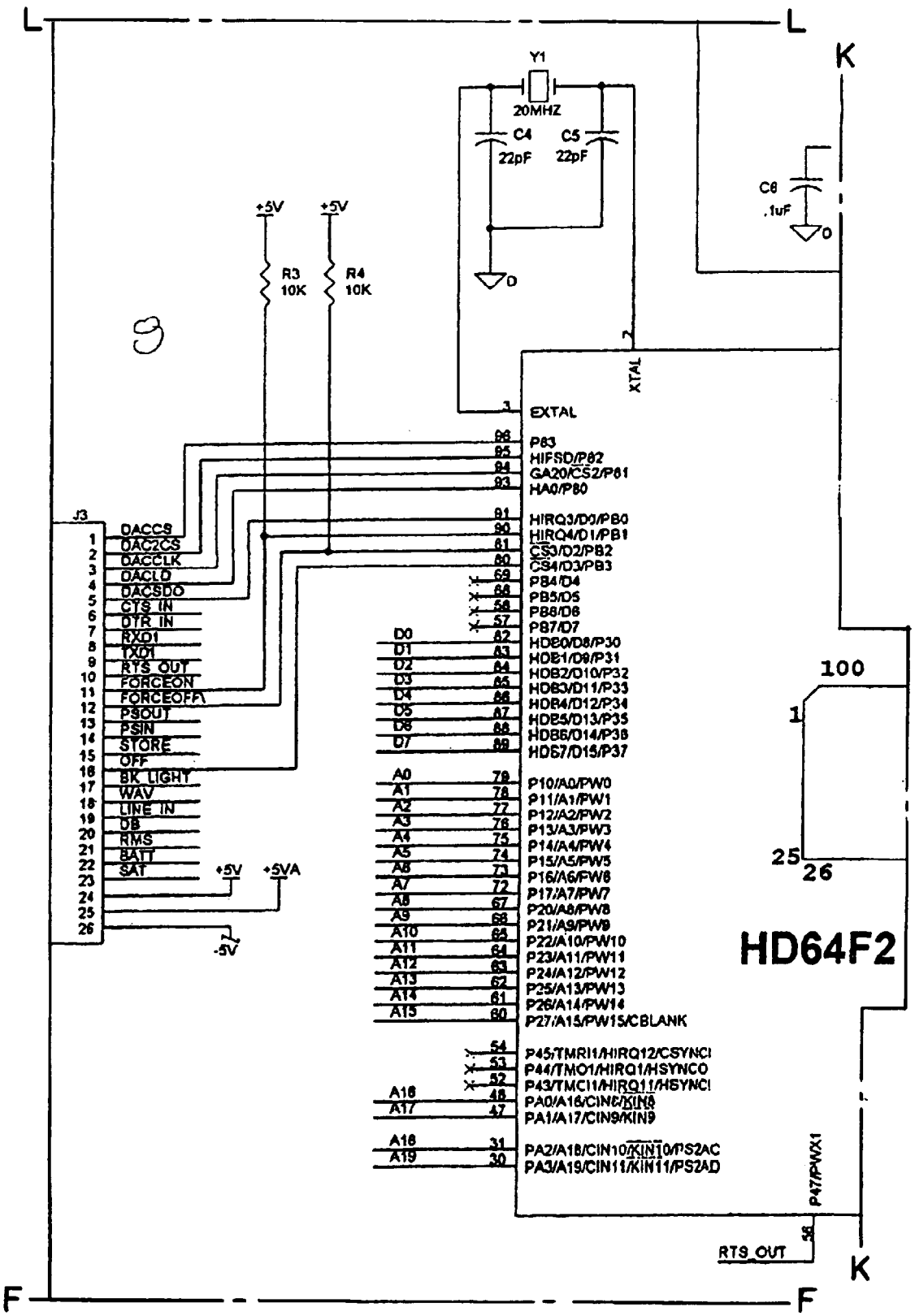
FIG. 8 is a front view of the ultrasonic instrument of the invention.

Amplifier 56 is controlled by a sensitivity setting such that the overall sensitivity of the system is determined by the micro-controller whereby an operator using a controller 72 on a front panel of the instrument 600 can adjust the overall sensitivity (see FIG. 5 and FIG. 7). As a result, if the sensitivity of the system is lowered by a predetermined level, the clip signal output from amplifier 56 is toggled such that gain switching occurs at the transducer pre-amp and at variable gain amplifier 18. In preferred embodiments, the predetermined level is 10 dB downward from the maximum sensitivity of the system.

With reference to FIG. 2A, differential amplifier 43 (U4A) receives the output 268B of variable gain amplifier 18 (FIG. 2B) on its positive input 241 (pin 3). This signal is received through resistors 251 (R13) and 253 (R17), and capacitor 255 (C10). The output of amplifier 43 is connected to zener diode 259 (D1) at TP1. Amplifier 43 functions as a positive rectifier circuit outputting a positive DC voltage proportional to the amplitude of the signal. Zener diode D1 clamps the output of amplifier 43 to a voltage of approximately 5 volts to prevent the micro-controller from being subjected to excessive voltage levels. As a result, a DC voltage is generated which the micro-controller compares to a predetermined value. If the DC voltage is greater than the predetermined value then the micro-controller indicates saturation on the LCD display by displaying an over range condition.

Figures 1, 2F:
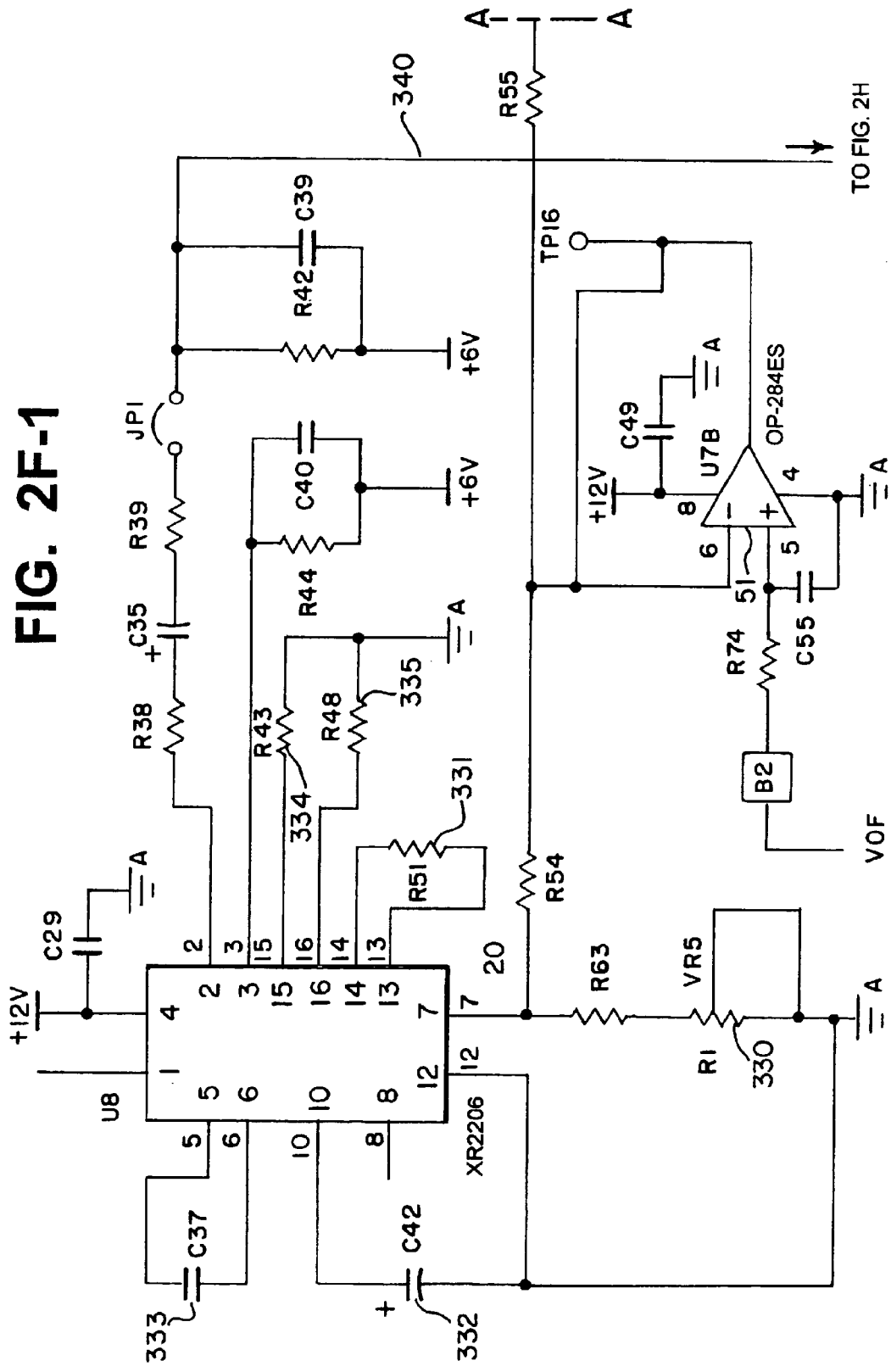
Figures 2, 2F:
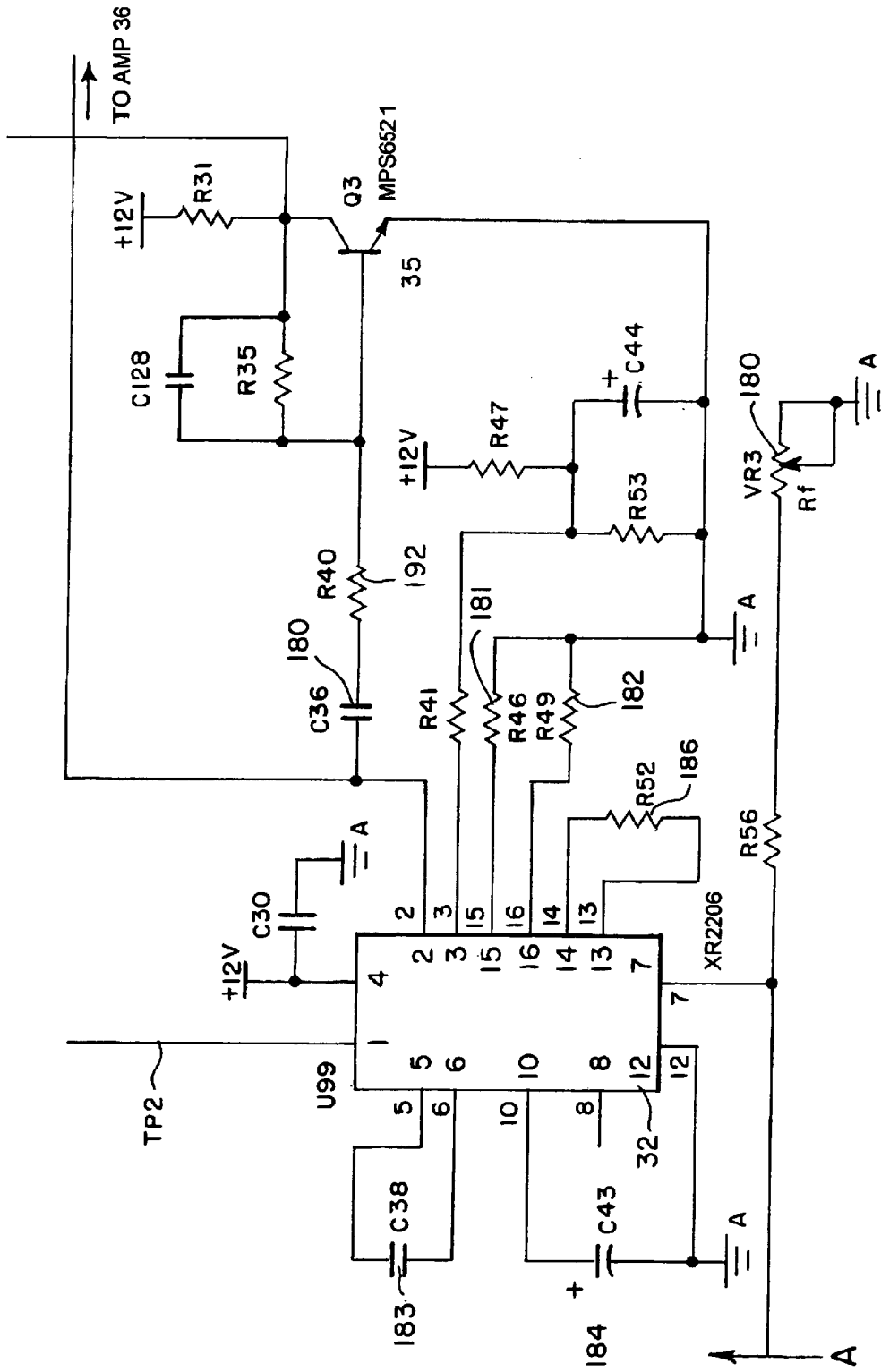
Figures 1, 2G:
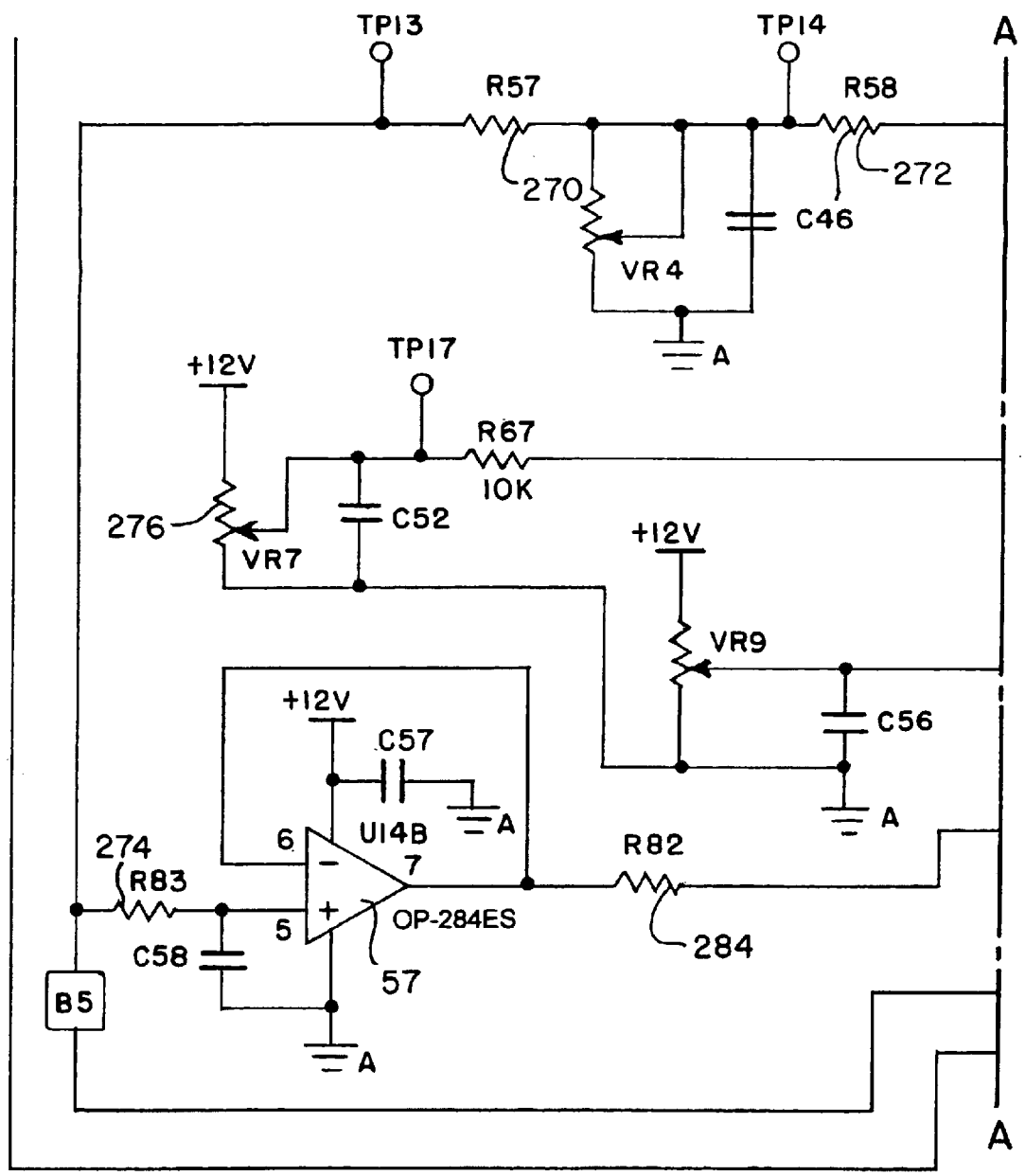
Figures 2, 2G:
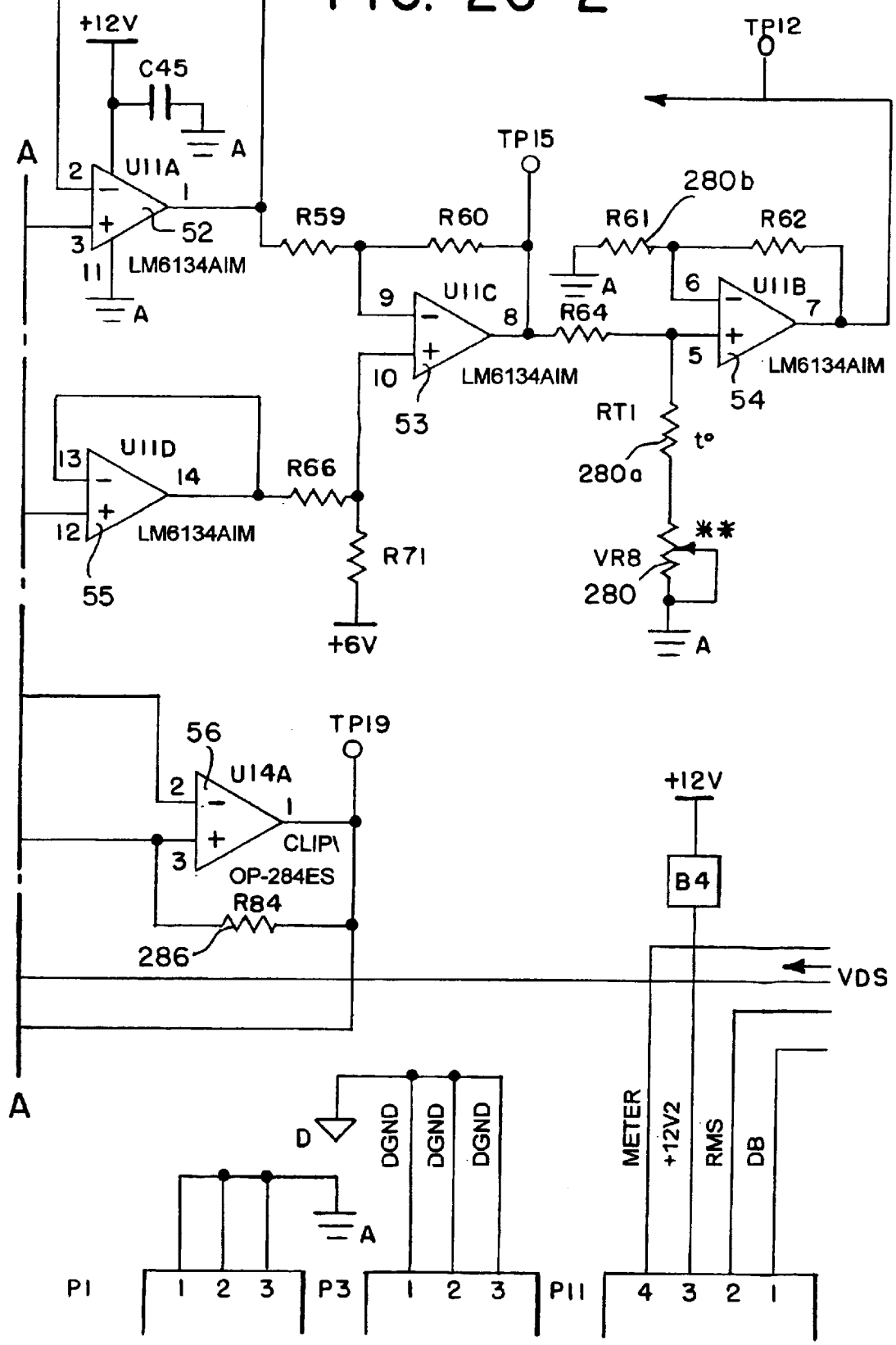
Figures 1, 2H:
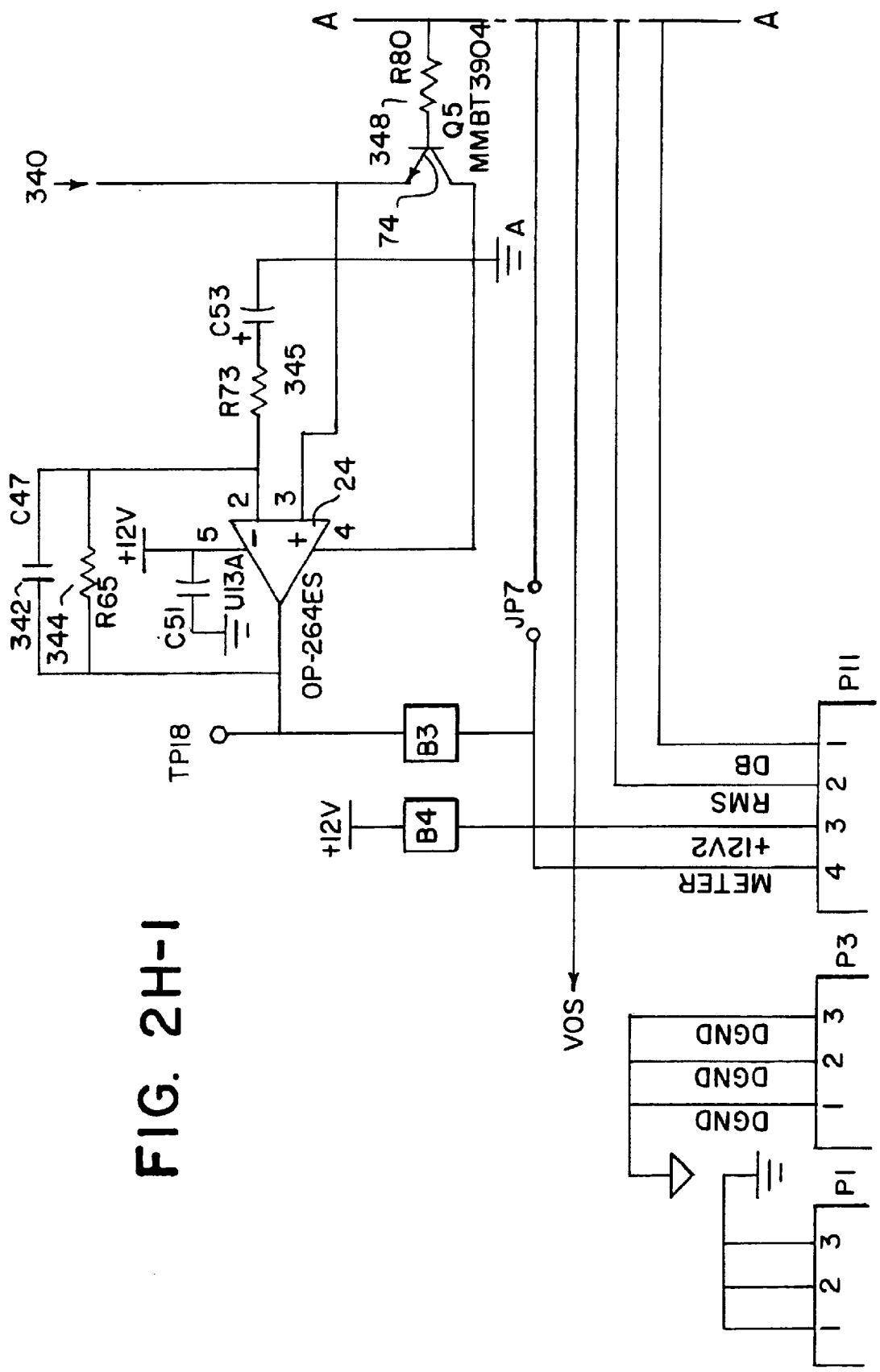
Figures 2, 2H:
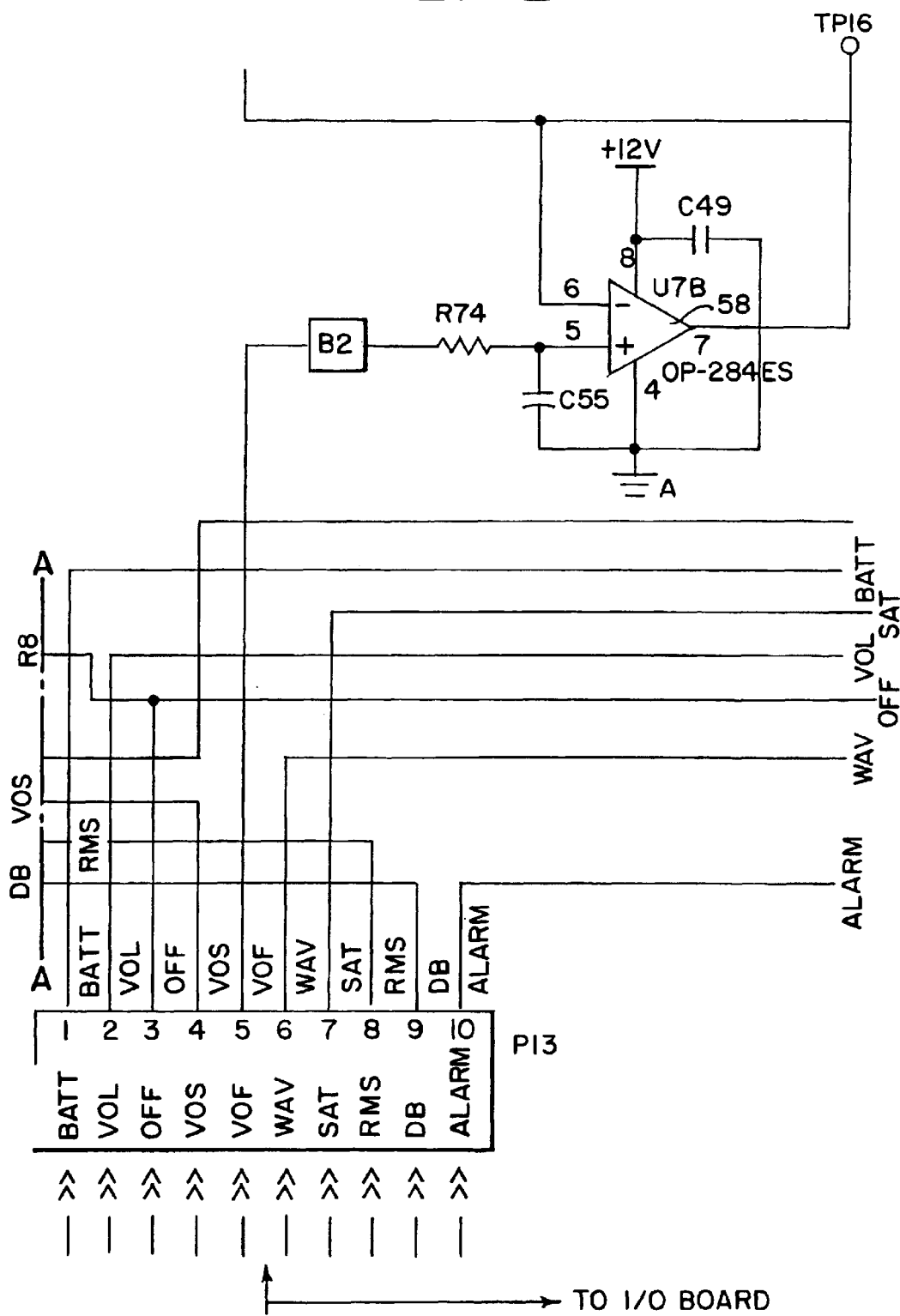

The output of amplifier 18 is also applied to the first of a pair of function generator circuits that form the dual heterodyne circuits 20 (U8), 32 (U99), as shown in FIGS. 2F-1 and 2F-2. The output of amplifier 18 is further connected to resistor 130 (R8) that is connected in series with capacitor 135 (C5), which is subsequently connected to the base of transistor 134 (Q1) (FIG. 2C). The collector of transistor 134 is capacitively connected to the input (pin 1) of the second of the pair of function generator circuits, i.e., heterodyne circuit 32 (U99) (see FIG. 2F-2) by way of capacitor 136 (C3). As shown in FIG. 2C, a feed back loop comprising capacitors 140 (C12), 142 (C11), transistor 47 (Q2) and variable resistor 144 (VR14) provides a feedback signal at pin 1 of function generator (heterodyne) circuit 32 (see FIG. 2F-2). In accordance with the invention, transistor 46 amplifies the output signal from amplifier 18 by a predetermined amount. In the preferred embodiment, the predetermined amount is 10 dB.

Figures 1, 2I:
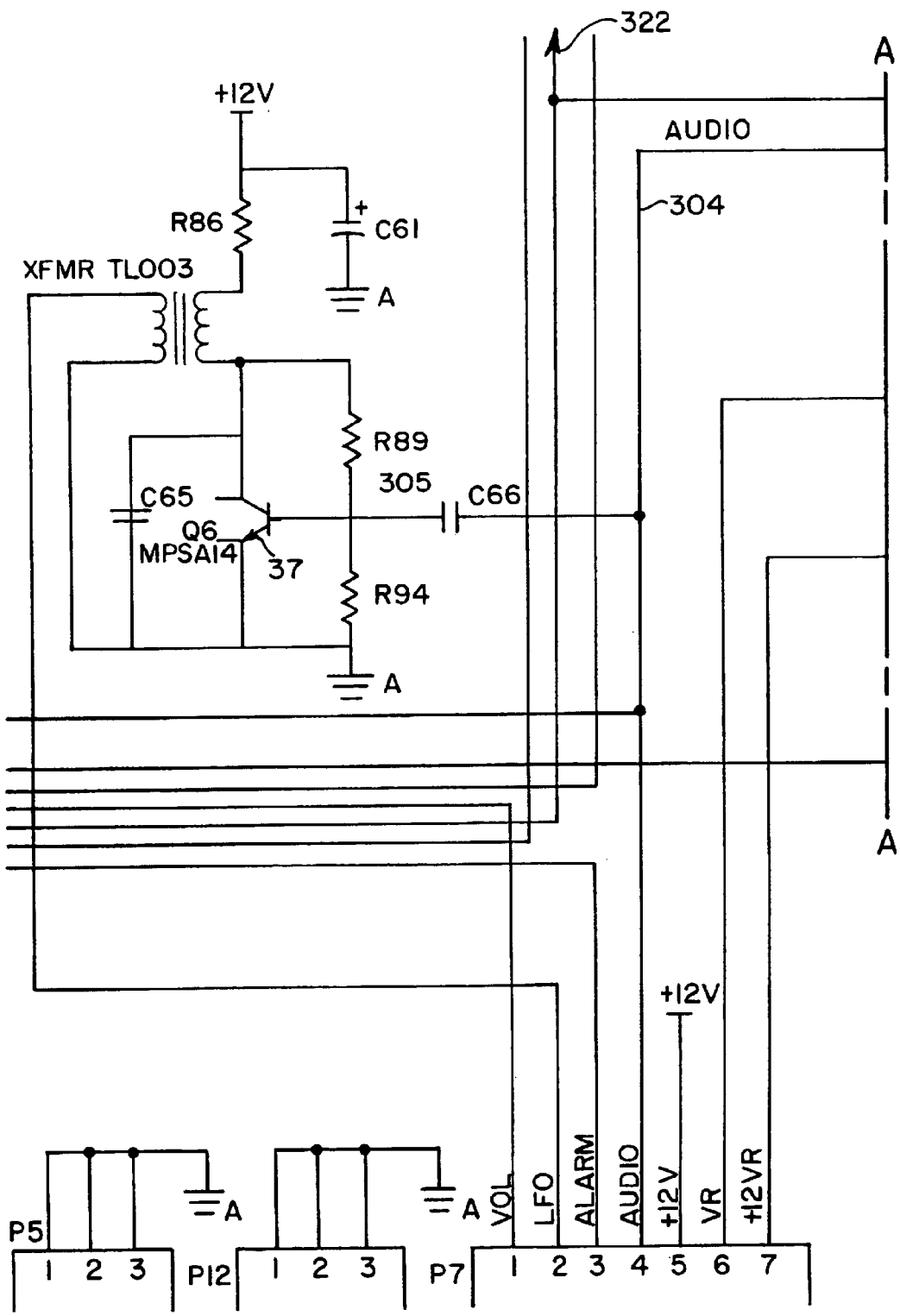
Figures 2, 2I:
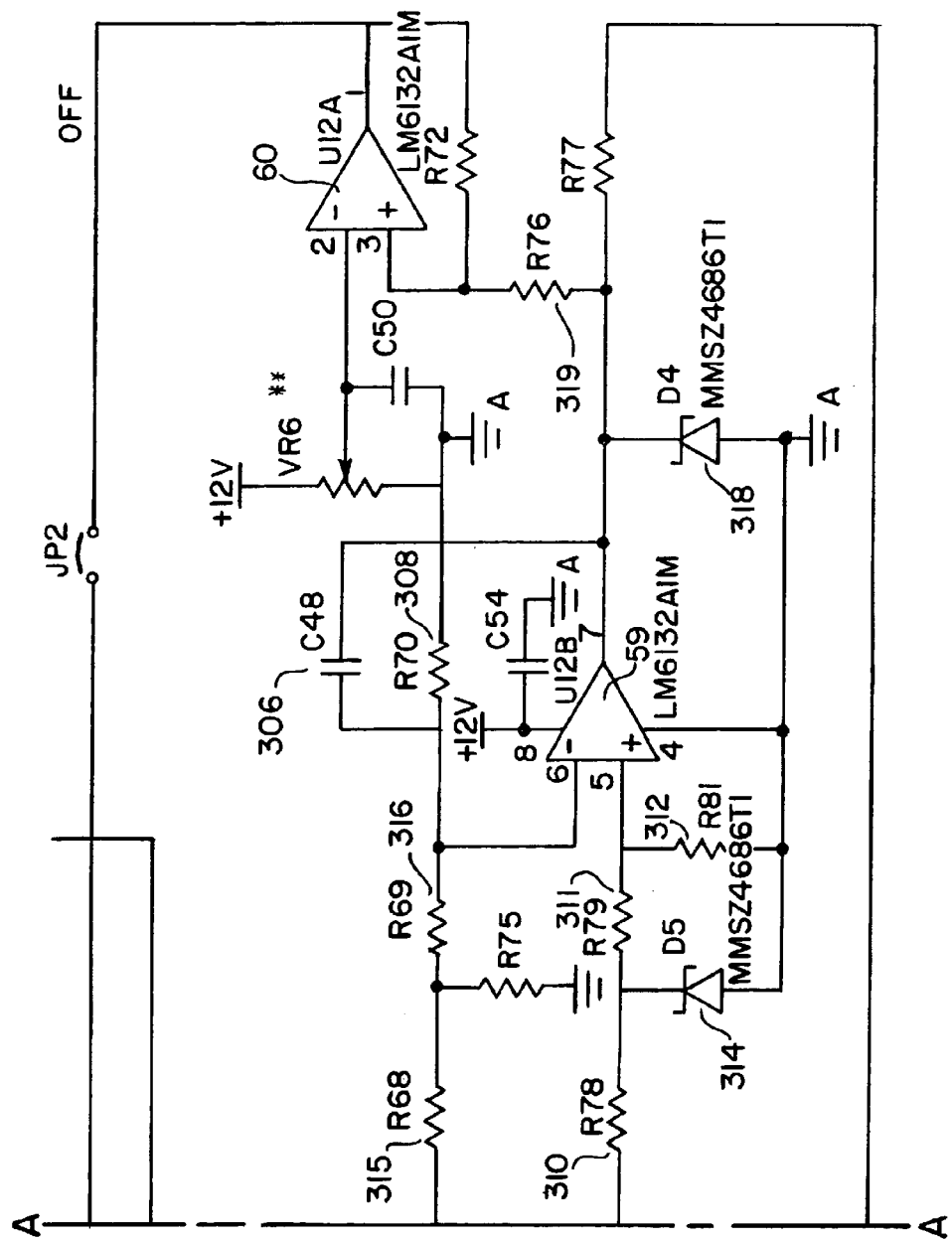
Figures 1, 2J:
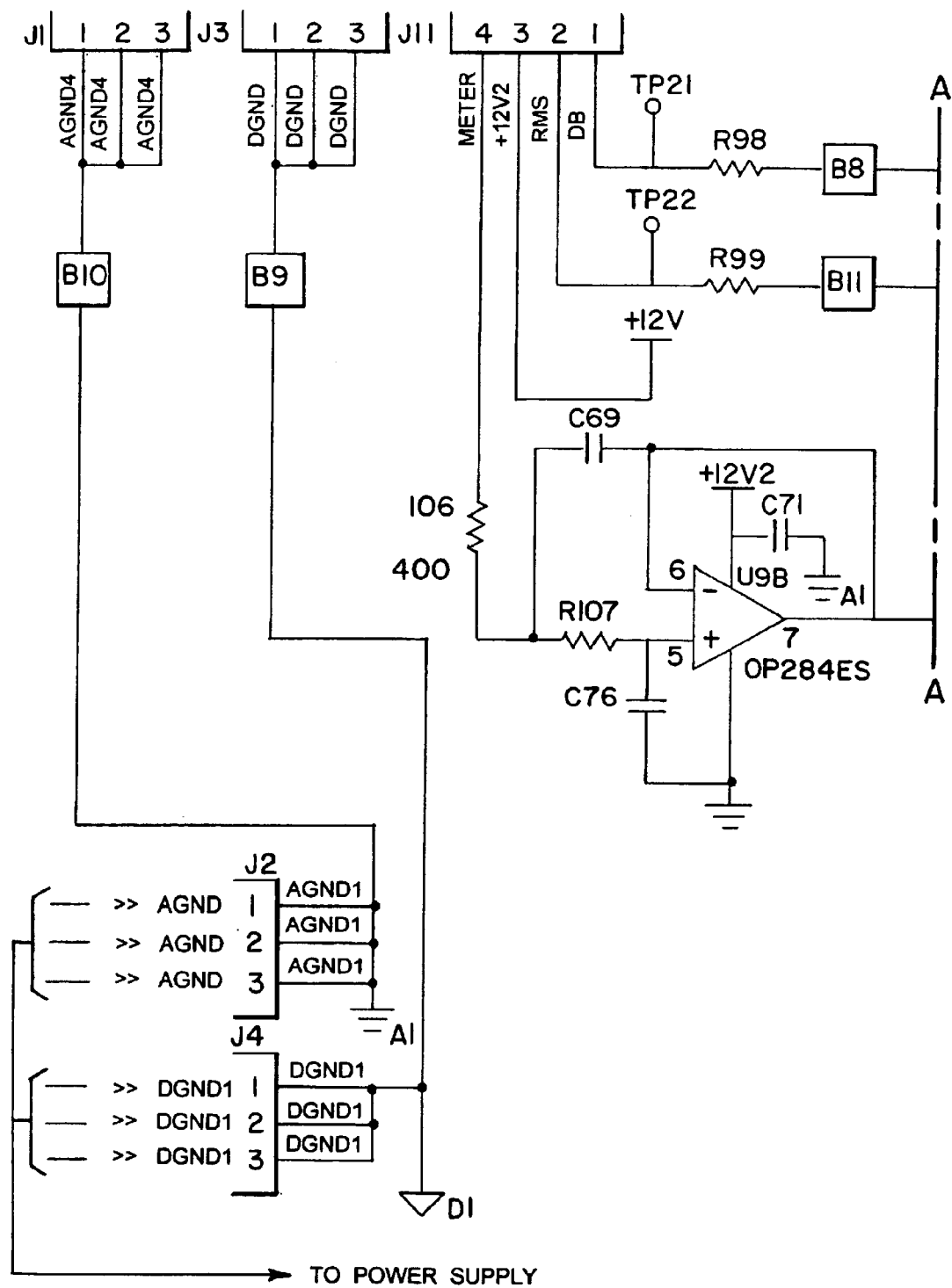
Figures 2, 2J:
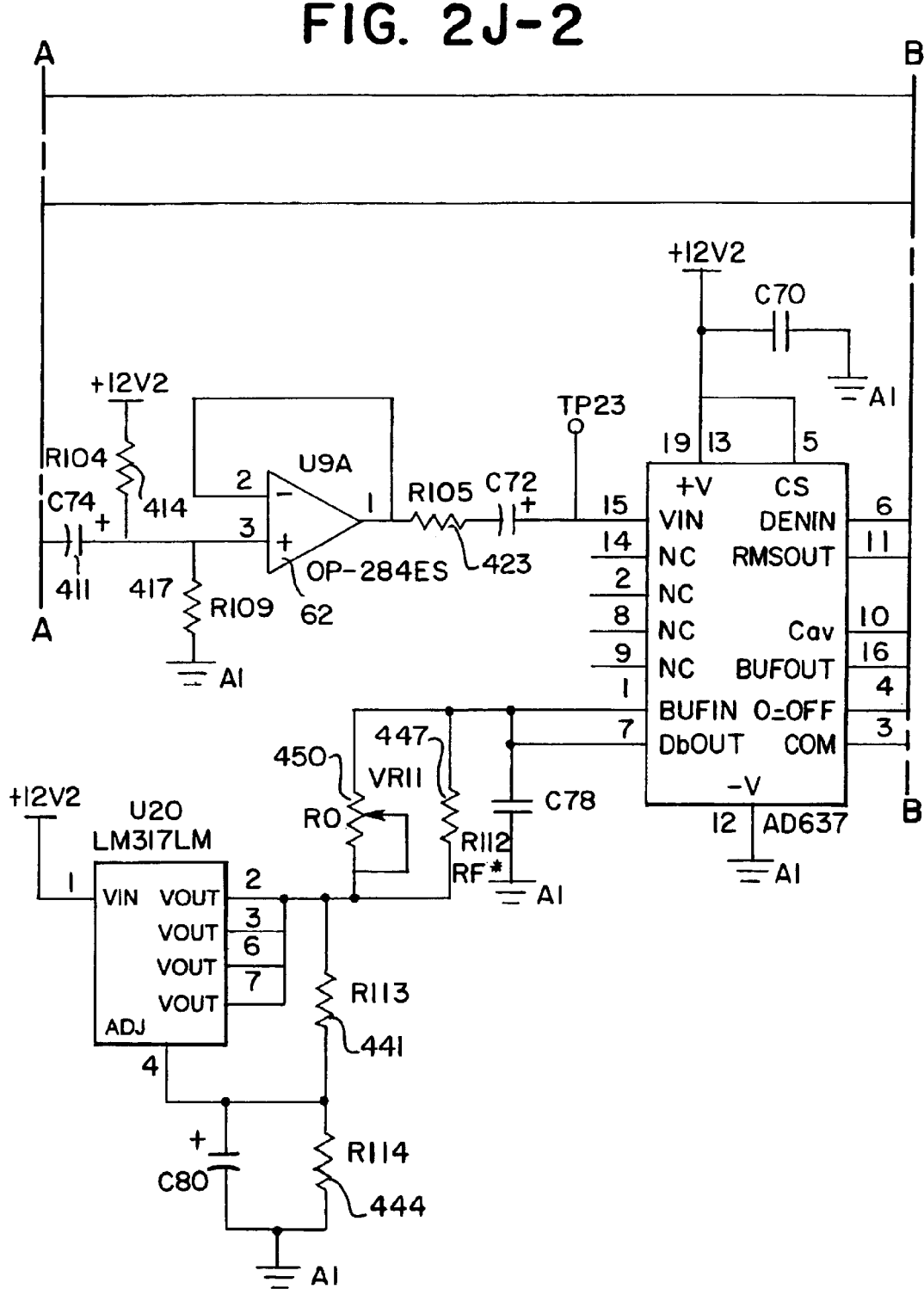
Figures 2, 2J, 3:
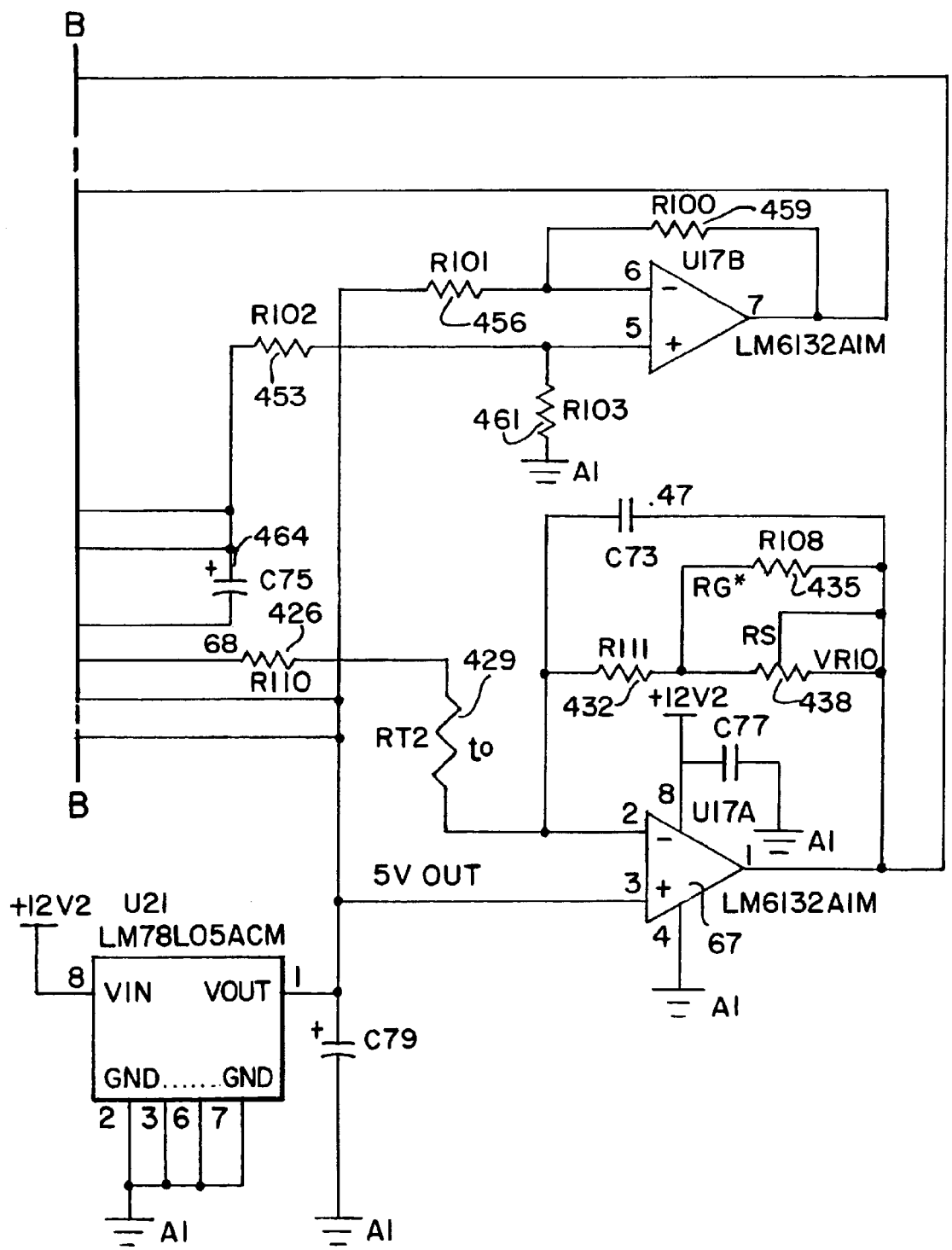
Figures 2, 2K:
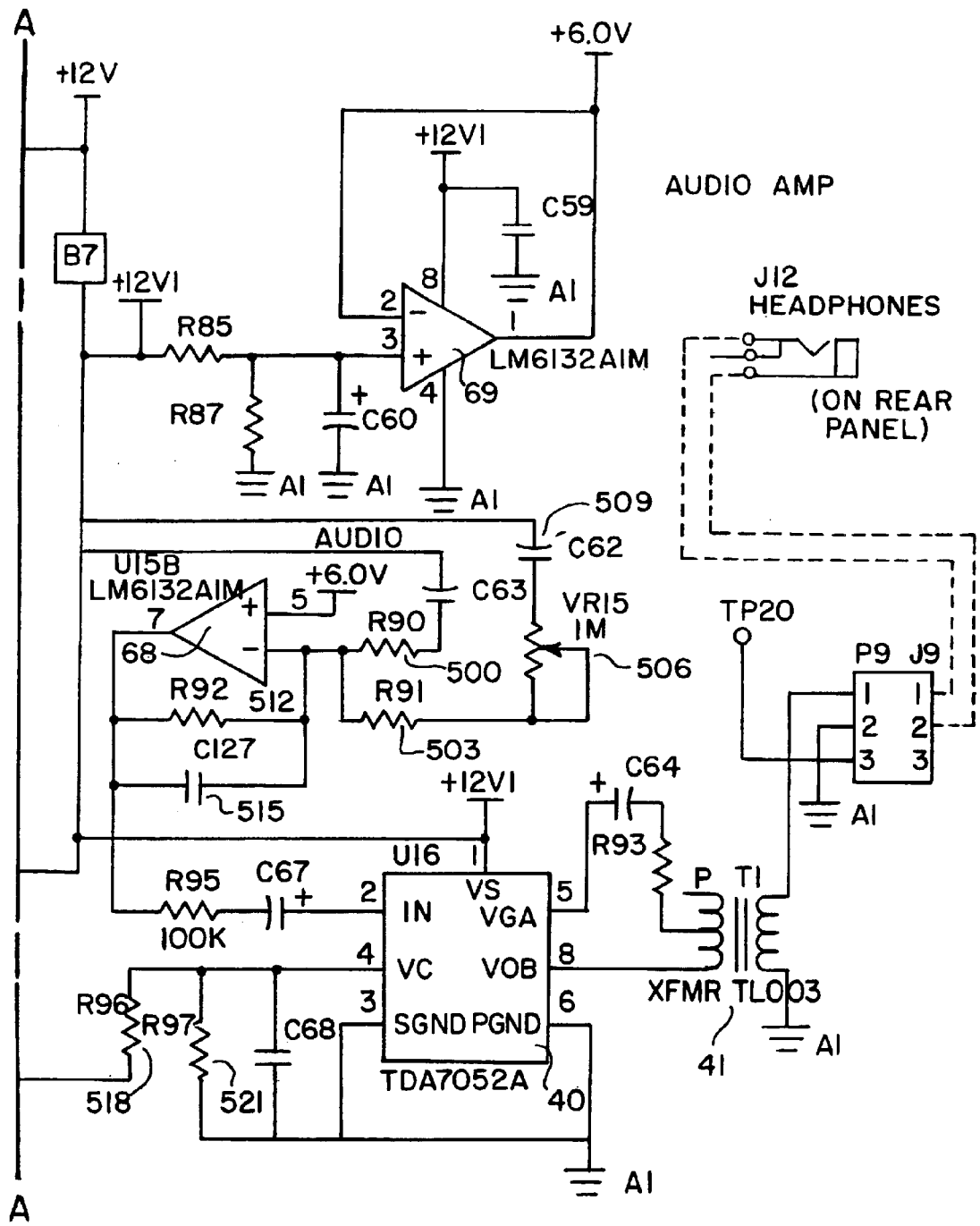

Ultrasonic signals leaking from a container (not shown) are detected by the transducer (not shown), amplified and frequency shifted such that a user is provided with an indication of the existence of a leak by way of the sound heard in a pair of headphones (see FIG. 2K-2). The actual frequency shift of the ultrasonic signal is accomplished in the function generator 32. The generator (FIG. 2F-1) may be a commercially-available integrated circuit, such as the EXAR 2206, which has been wired to produce sine wave outputs at a frequency determined by tuning resistor 180 (VR3) connected to pin 7 of circuit 32, resistors 181 (R46) and 182 (R49) connected from pins 15 and 16 to ground, capacitors 183(C38), 184 (C43), and resistor 186 (R52). One characteristic of circuit 32 is that a particular bias applied to its input (pin 1) will cause it to produce an amplitude-modulated (AM), suppressed-carrier output. The bias to obtain this suppressed-carrier modulation is derived from variable resistor 144 (VR14) (FIG. 2C). If capacitor 183 (C37) and resistor 180 (VR3) are selected to produce a carrier signal that differs from the ultrasonic signal by a frequency in the audio band, the output of heterodyne circuit 32 will be an audio signal related to the input ultrasonic signal and a much higher signal. In particular, the output signal will be equivalent to the sum and difference frequencies of the ultrasonic signal and the carrier signal generated within circuit 32, but the carrier signal itself will not be present in the output. If for example, variable resistor 180 (VR3) is set such that circuit 32 generates a 42 kHz signal and the ultrasonic signal applied through capacitors C3 to circuit 32 is at 40 kHz, the output will be at 2 kHz and at 82 kHz. In preferred embodiments, the oscillator in circuit 32 is adjusted between a range of 20 kHz and 100 kHz.

Although a proper bias on the input to circuit 32 will eliminate or suppress the carrier generated by that circuit, it has been found that this adjustment is critical and some carrier may leak through due to temperature and voltage variations. Also, as the carrier frequency is changed due to changes in the setting of resistor 180 (VR3), there are changes in the circuit operation that may cause the carrier to appear in the output unless there is an adjustment of the bias. In order to provide this adjustment, a servo or feedback network is provided.

In particular, the output of circuit 32 is also capacitively coupled to the base of transistor 35 (Q3) by way of capacitor 190 (C36), and resistor 192 (R40), as shown in FIG. 2F-2. these components provide an input signal for the feedback network formed by transistor 47 that biases pin 1 of circuit 32 (see FIG. 2C). Here, transistor 35 provides amplification of the output signal from pin 2 of circuit 32 by a predetermined amount. In preferred embodiments, the predetermined amount of amplification is 40 dB.

The output from pin 2 of circuit 32 is also fed to voltage amplifier 36 (FIG. 2E), where the signal from pin 2 is buffered. By way of resistor 171 (R140), the output signal from amplifier 36 feeds the base of transistor 37 (Q6) over line 304, by way of capacitor 305 (C66) (FIG. 2I-1). Here, the output signal from amplifier 36 is coupled to transformer 39 to thereby generate a low frequency output ("LFO"). The audio signal on line 304 is also applied to summing amplifier 68 (FIG. 2K-2) which in turn drives amplifier 40. Amplifier 40 drives transformer 41 which is used to power the headphones. In preferred embodiments of the invention, transformer 39 has a turns ratio of approximately 1:0.05, and the output signal is used to drive low impedance loads. The transformer 41 has a turns ratio of 1:0.175.

The output signal from amplifier 36 (FIG. 2E) is also provided to amplifier 50, where it is attenuated by approximately −3 dB, based on resistors 300 (R34) and 302 (R26). Amplifier 50 (U1B) and amplifier 36 are typically standard "off-the-shelf" ICs, such as an OP-284ES. The output from amplifier 50 is supplied to the micro-controller for conversion into a digital signal by an analog-to-digital converter located in the micro-controller (not shown). This digital signal is converted into a digital format, such as a WAV file, for subsequent image processing.

Signals VR and +12VR are applied from a power supply (FIG. 2K-1) to the circuit of FIGS. 2I-1 and 2I-2. These signals are applied to the negative and positive terminals of differential amplifier 59 (U12B). Capacitor 306 (C48) and resistor 308 (R70) are connected to form a feedback loop about amplifier 59. The signal +12VR is applied to the positive input of amplifier 59 through resistors 310, 311 and 312 (R81). A zener diode 314 (D5) is connected between resistors 310 and 311. VR is connected to the negative input of amplifier 59 through resisters 315 (R68) and 316 (R69). The output of amplifier 59 is connected to zener diode 318 (D4), and through resister 319 (R76) to the positive input of amplifier 60 (U12A). A variable resistor 320 (VR6) is connected to amplifier 60 and serves to establish a reference point of amplifier 60.

Signal +12V1 is applied from the power supply (FIG. 2K-1) to the bias amplifier shown in FIG. 2D. This 12V signal is applied to the VIN terminal of voltage regulator 48 (U2). The output (VOUT) of voltage regulator 48 provides a +5 volt TTL signal that is supplied to amplifier 49 (U1A) by way of resistors 360 (R6), 362 (R9), and capacitors 364 (C7) and 365 (C8). Amplifier 49 provides a regulated +2.5V voltage that is used as a reference voltage in accordance with the invention. The +5V voltage is also used to provide a TTL reference level to all other circuit ICs where required.

With further reference to FIG. 2I-2, amplifiers 59 and 60 provide a comparator circuit that generates a low battery monitor. By way of zener diode D5, a regulated reference voltage is generated and applied to the positive input (pin 5) of amplifier 59. Concurrently with application of the regulated reference voltage, a battery voltage is applied to the resistive divider (315, 311) on the negative side (pin 6) of amplifier 59. The reference voltage at zener diode D5 remains relatively constant due to the clamping action of the zener diode D5.

Zener diode D4 in FIG. 2I-2 is connected to the output of amplifier 59, and clamps the output voltage to approximately 5 volts such that the micro-controller is not subjected to excessive voltage levels. If the battery voltage falls below a predetermined level, then the input voltage at the negative input of amplifier 59 will also fall below the reference level. In accordance with the invention, the output of amplifier 59 is zero to indicate a fully charged battery, and approximately 3.5 volts to 4 volts (nominal) to indicate that the battery capacity is low and needs to be recharged. The output of amplifier 59 is inverted in amplifier 60 and produces the OFF signal used in the circuit of FIGS. 2H-1 and 2H-2 as will be explained subsequently. As a result, a means is provided for the micro-controller to indicate on an LCD whether or not the battery is adequately charged. In preferred embodiments, amplifiers U12A and U12B are standard "off-the-shelf" ICs, such as an LM6132.

In the contemplated embodiments of the invention, the LCD is a screen that is large so that the display can easily be seen by the operator. In accordance with the contemplated embodiments, this would include a time series display of the heterodyned ultrasonic signal to permit the viewing of measurement trends in real time.

Returning to FIG. 2E, when the battery level falls below the optimum operating level, the base of transistor 73 (Q4) is pulled high by the output of amplifier 60 (FIG. 2I-I) online 322. This causes the plus input of amplifier 36 to be low. As a result, the output signal from amplifier 50 is also low.

As stated previously in connection with FIG. 1A-1, the first output from amplifier 18 is applied to the first of the pair of function generator circuits, e.g., circuit 20 (see FIG. 2F-1). This generator may also be a commercially available integrated circuit, such as the EXAR 2206, which has also been wired to produce sine wave outputs at a frequency determined by tuning resistor 330 (VR5) connected to pin 7 of the circuit 20, resistor 331 (R51), capacitor 332 (C42), as well as capacitor 333 (C37) connected between pins 5 and 6, and resistors 334 (R43) and 335 (R48) connected to ground from pins 15, 16 of circuit 20.

Function generator circuit 20 multiples the first output signal using an oscillator that is internal to circuit 20. In a manner similar to circuit 32, the sum and difference frequencies of the ultrasonic signal are also generated at the output pin 2 of circuit 20. In preferred embodiments, the local oscillators in circuit 20 and circuit 32 are nominally set to 38 kHz. As with the tuning resistor 180 (VR3) that is connected to circuit 32, if tuning resistor 330 (VR5) is set such that circuit 20 generates a 42 kHz signal and the ultrasonic signal applied is at 40 kHz, the output at pin 2 of circuit 20 will be at 2 kHz and at 82 kHz. Since only the audio band signal is desired, the filter circuit comprising resistors R38, R39, R42 and R44, capacitors C35, C40 and C39 will eliminate the 82 kHz sum signal. In preferred embodiments the oscillator in circuit 20 is adjusted between a range of 20 kHz and 100 kHz.

Figures 3, 3A, 4, 5, 6, 7, 8, 9:
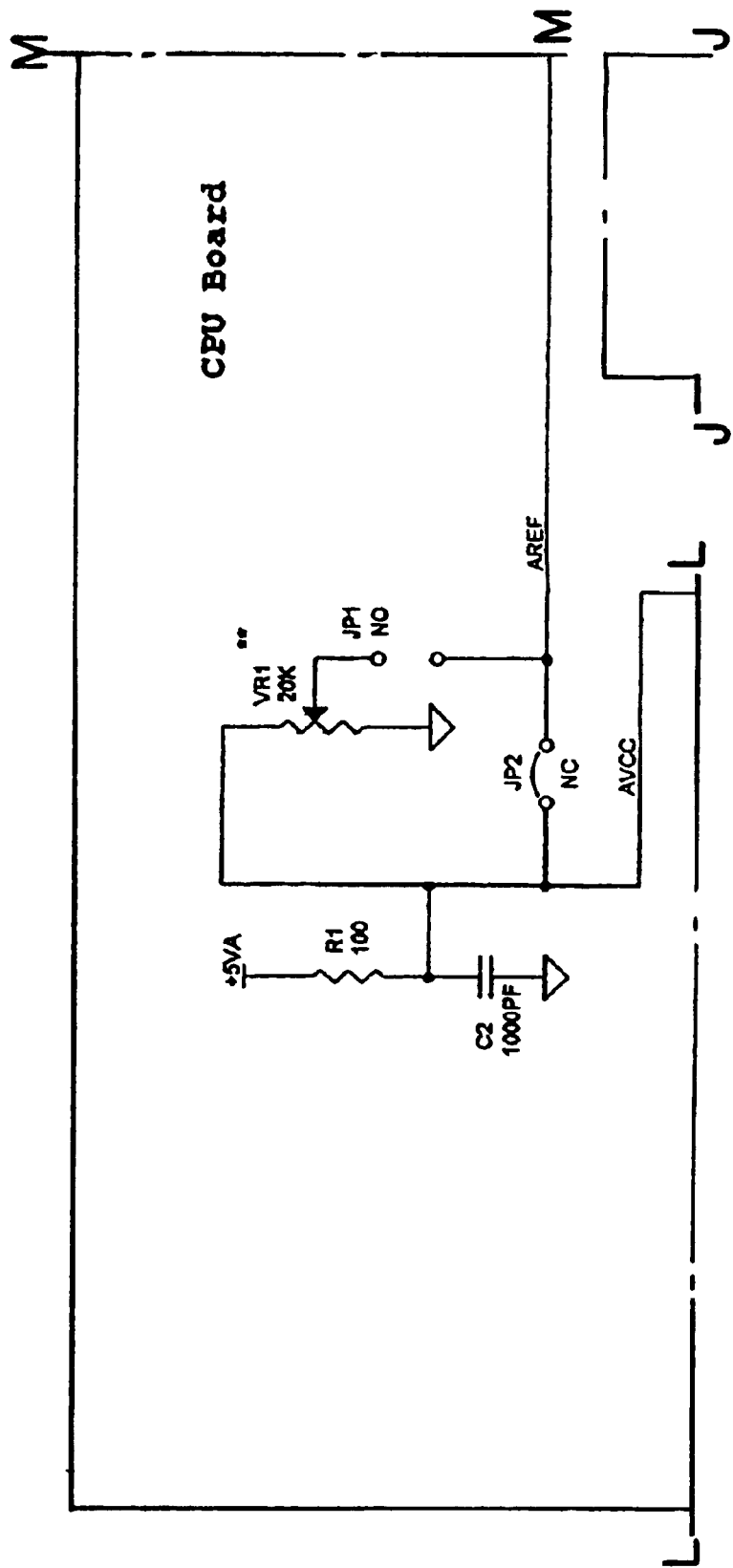
Figures 3, 3A, 4, 5, 6, 7, 8, 9, 10:
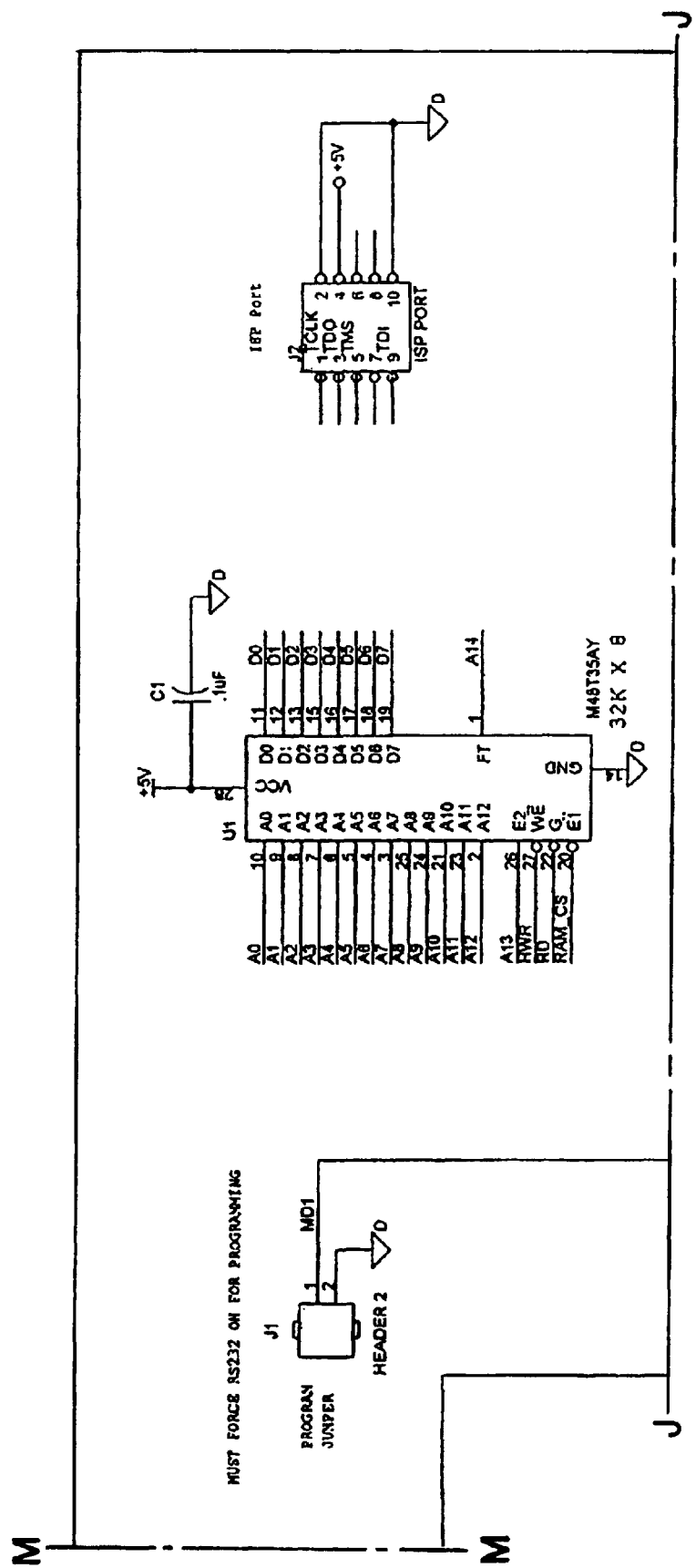
FIG. 10. is an illustration of an exemplary network of piping in which the method of the invention is implemented.
Figure 3B:
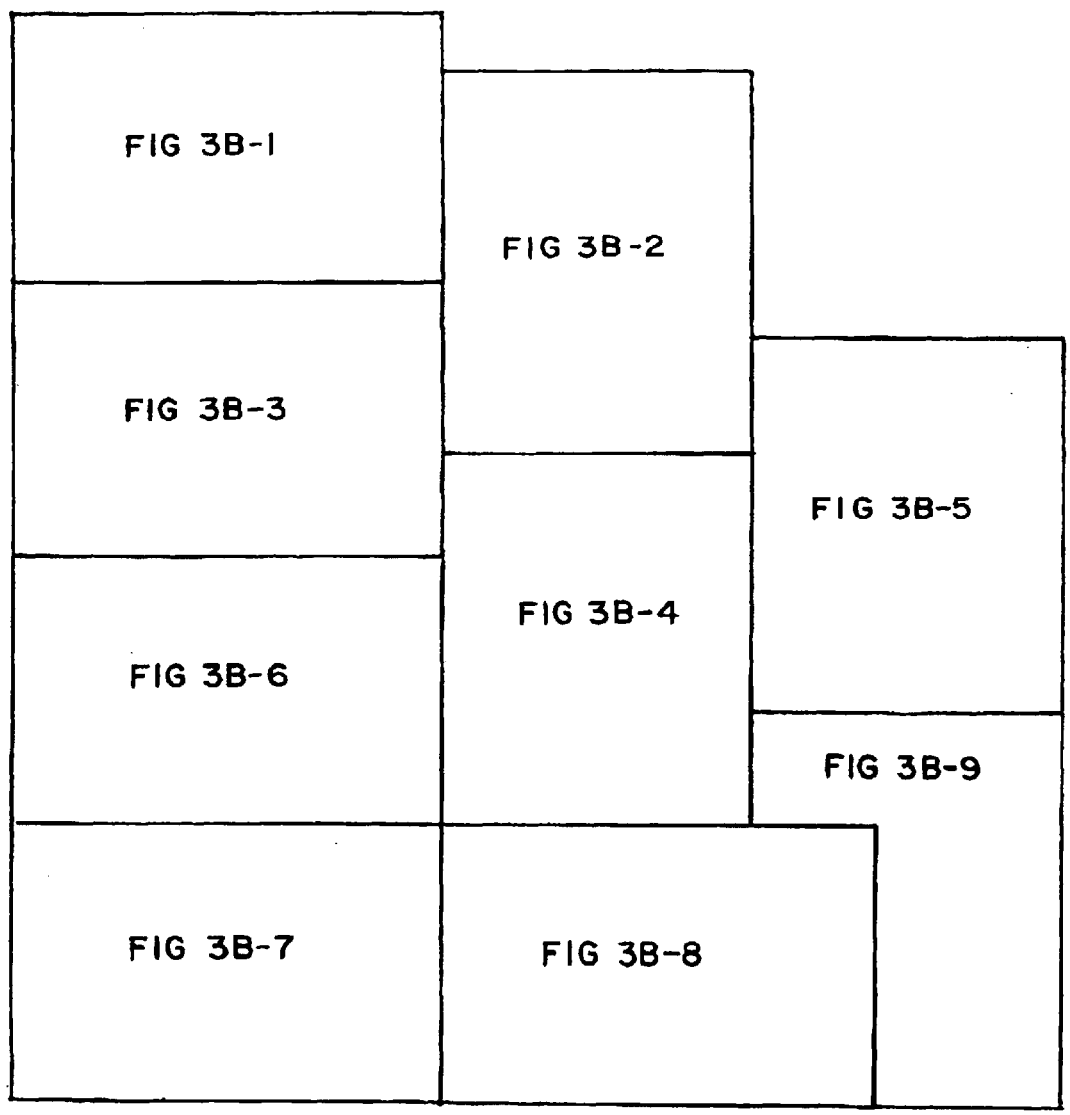
Figures 1, 3B:
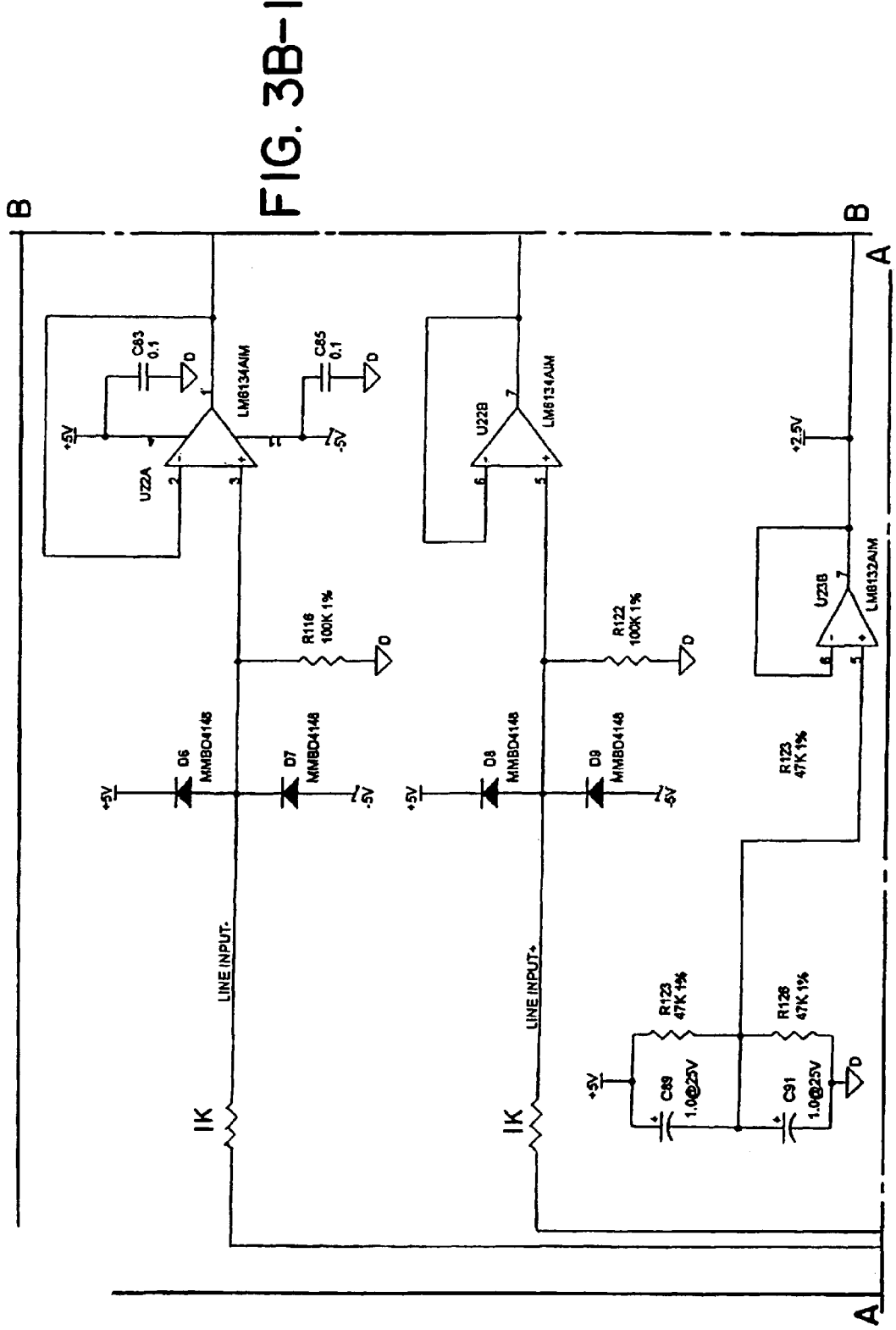
Figures 2, 3B:
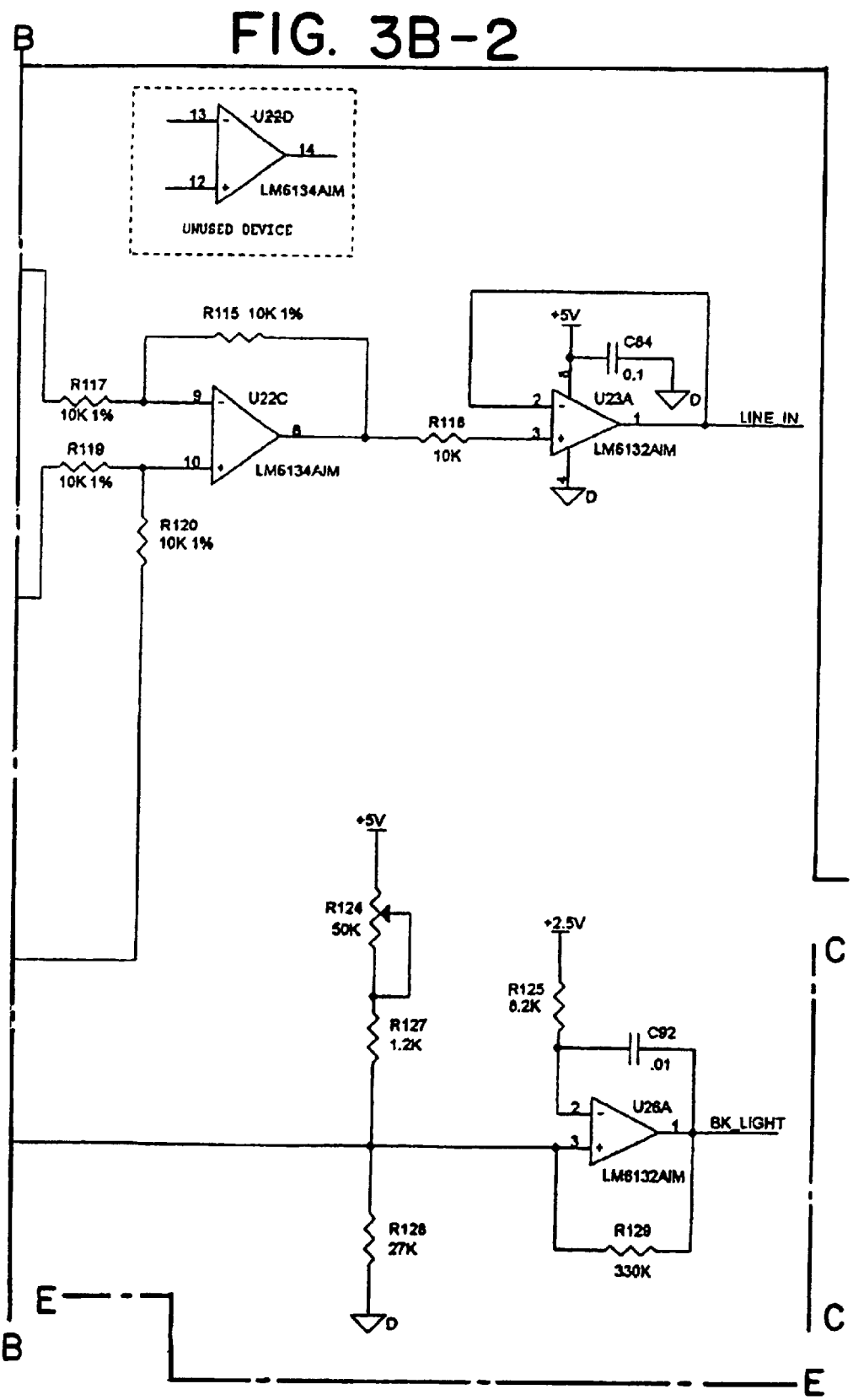
Figures 3, 3B:
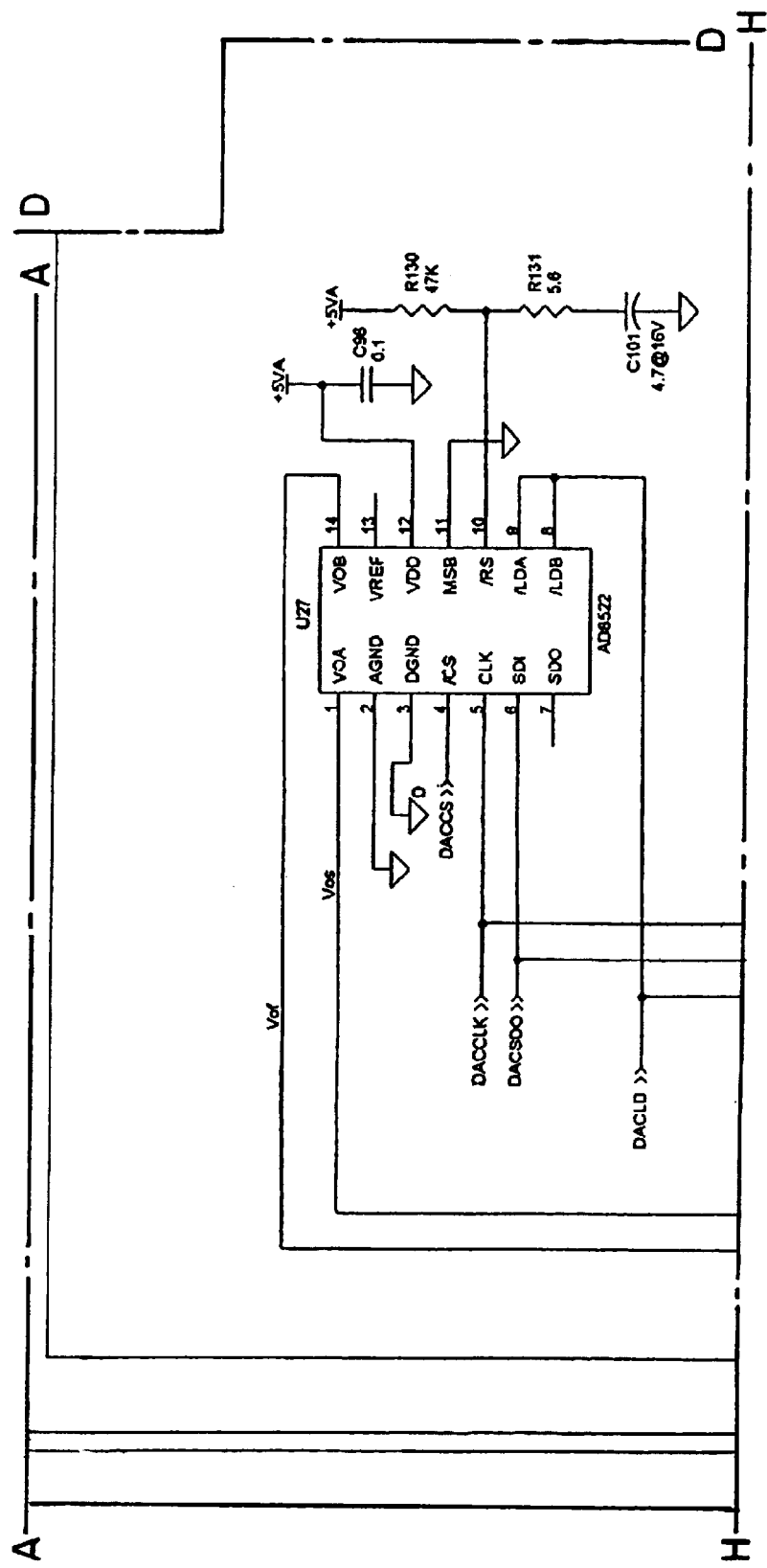
Figures 3, 3B, 4:
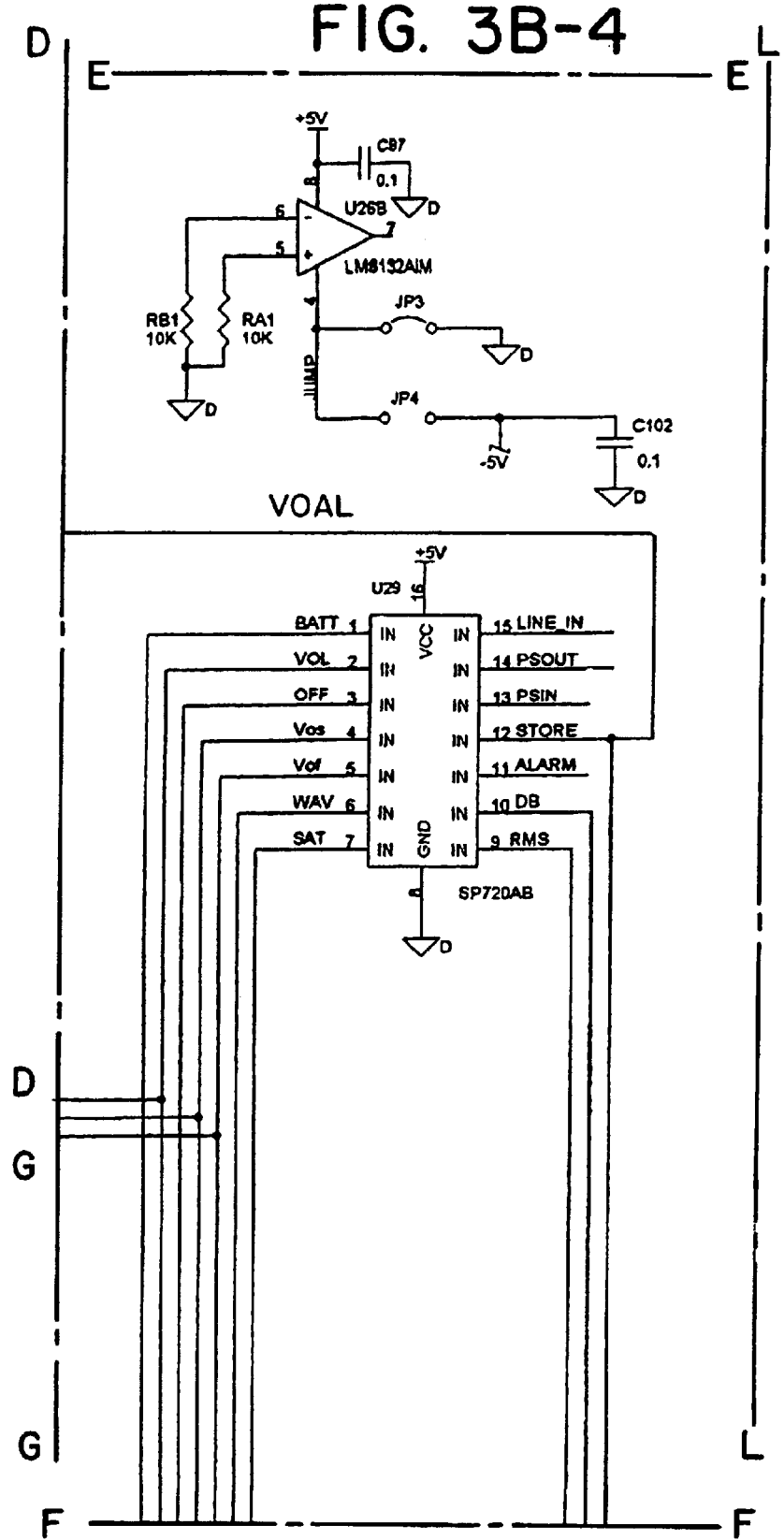
Figures 3, 3B, 4, 5:
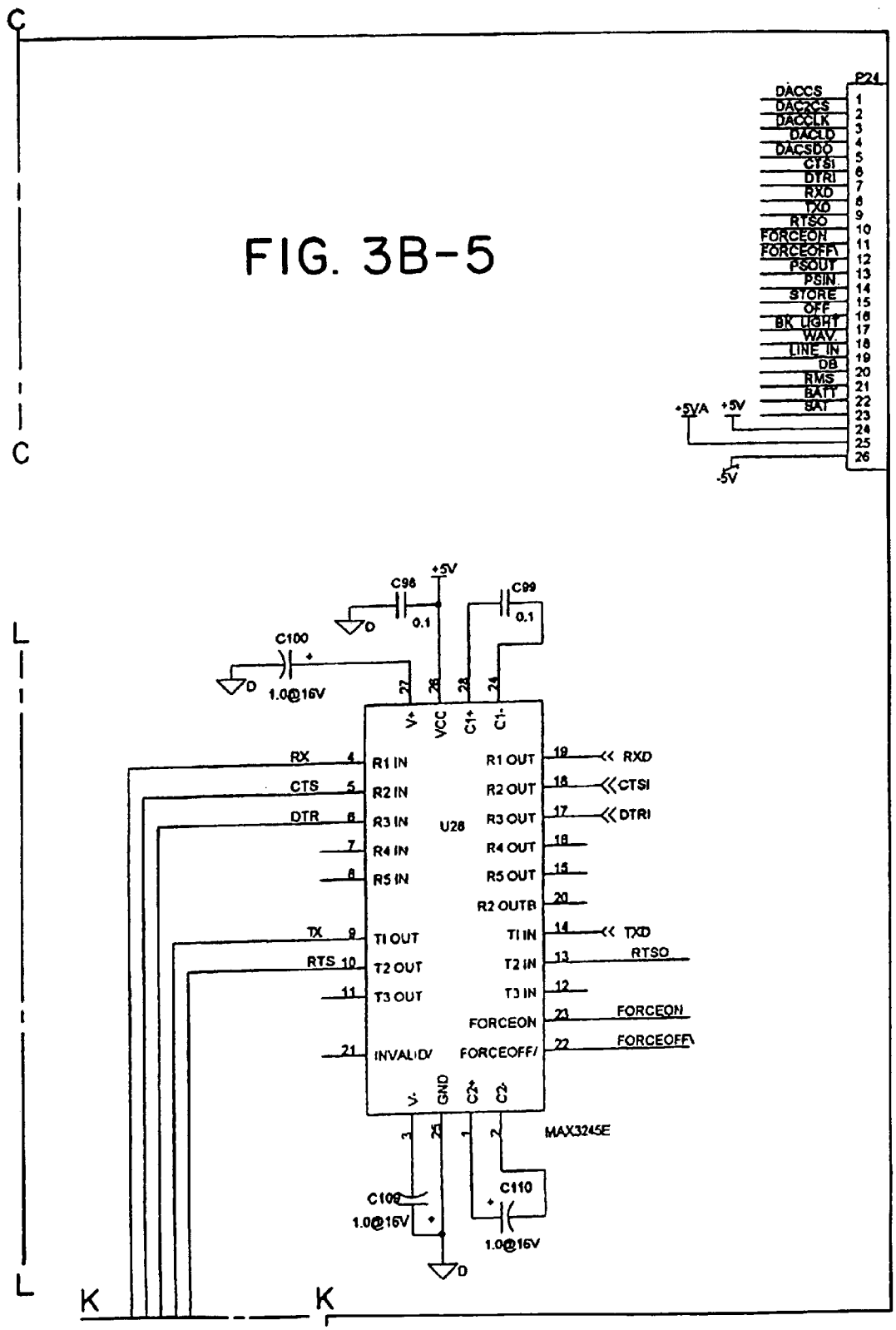
Figures 3, 3B, 4, 5, 6:
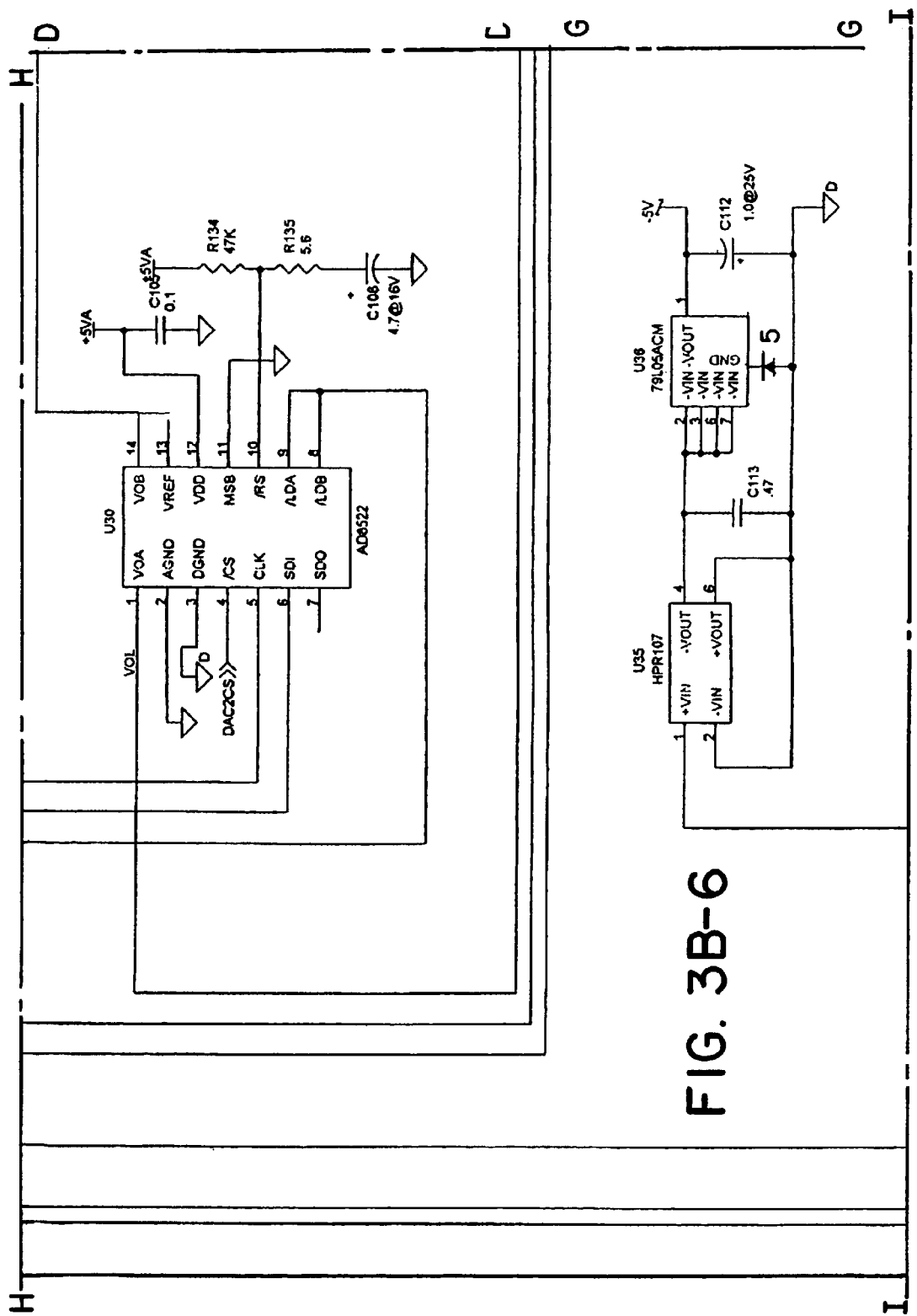
Figures 3, 3B, 4, 5, 6, 7:
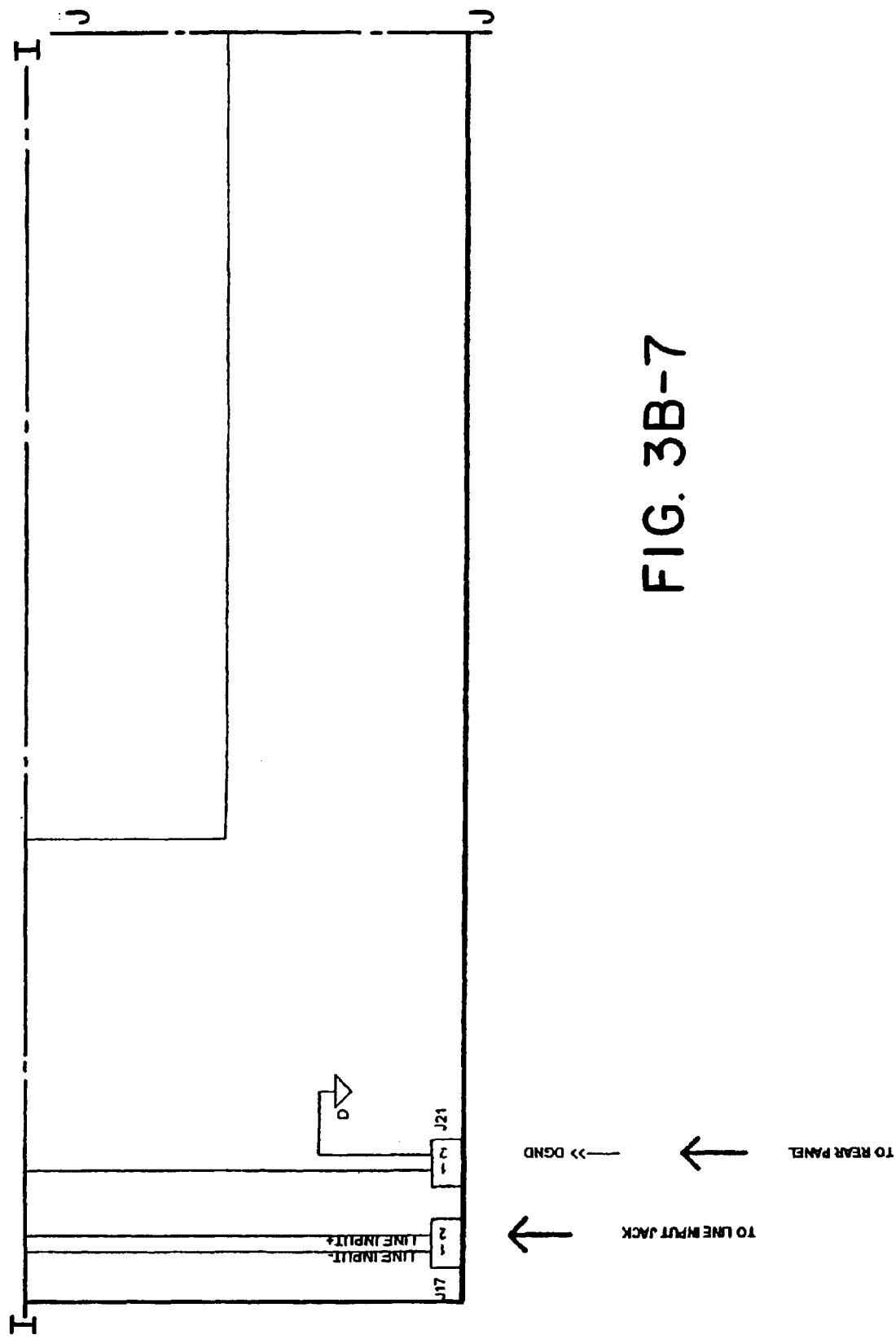
Figures 3, 3B, 4, 5, 6, 7, 8:
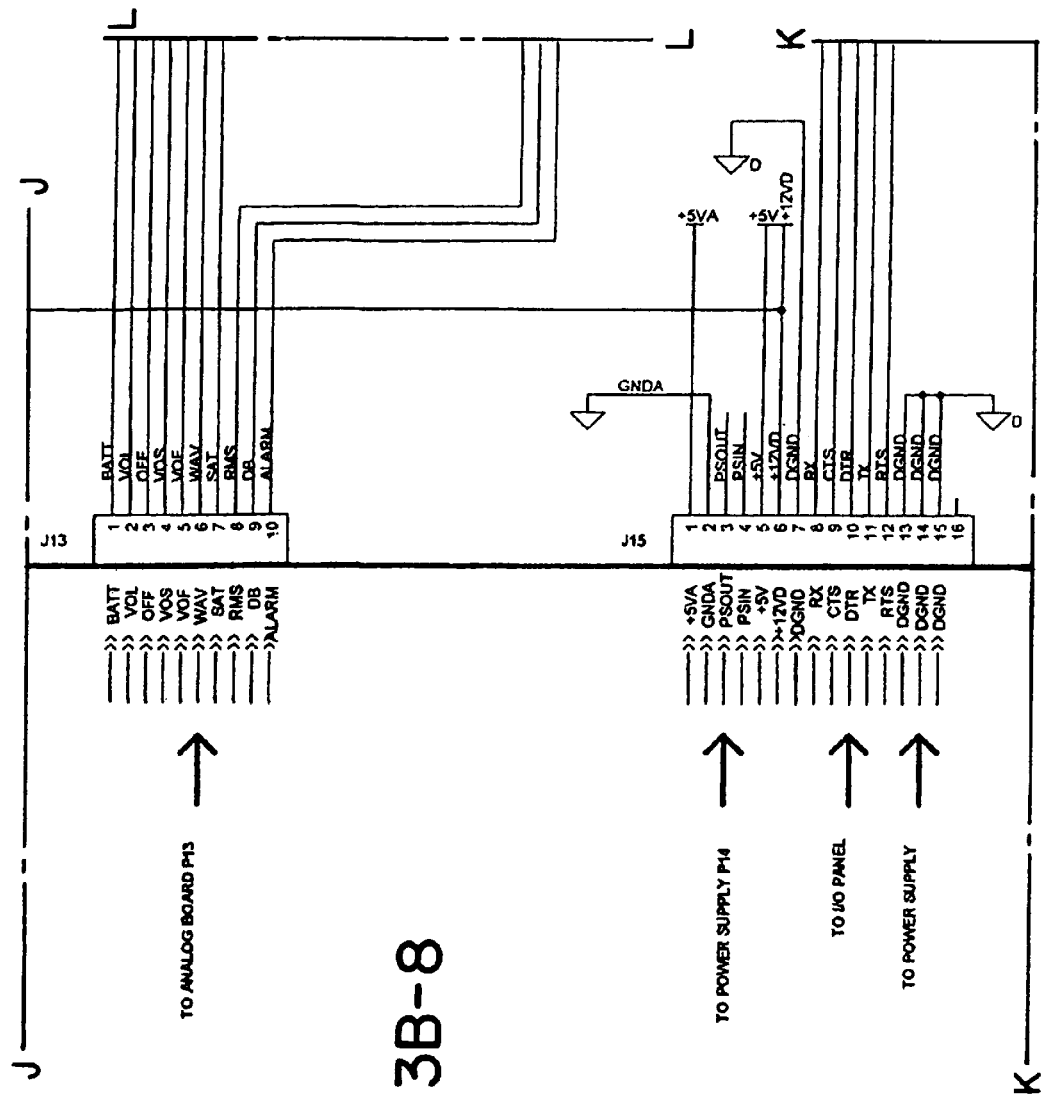
Figures 3, 3B, 4, 5, 6, 7, 8, 9:
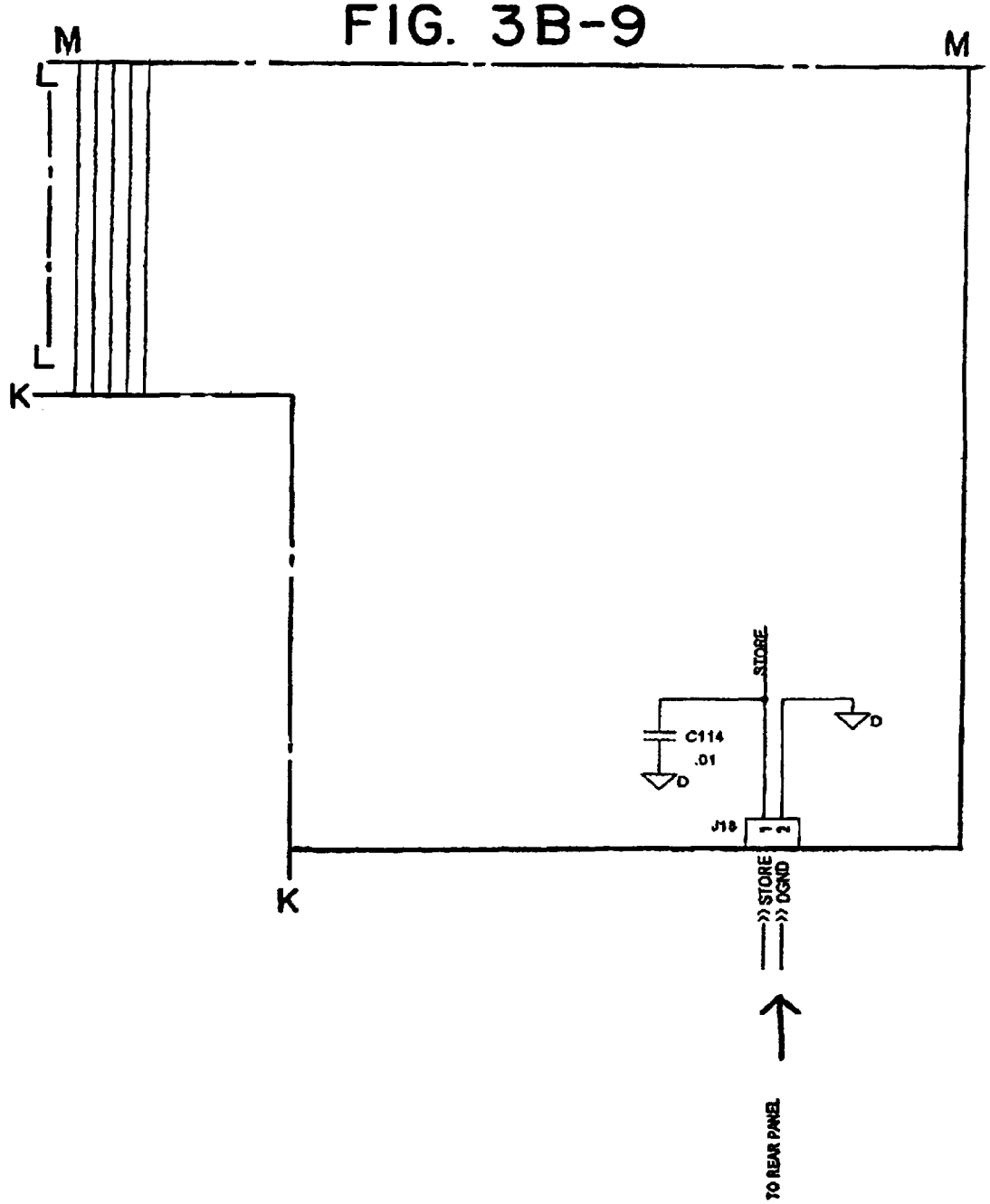
Figure 6:
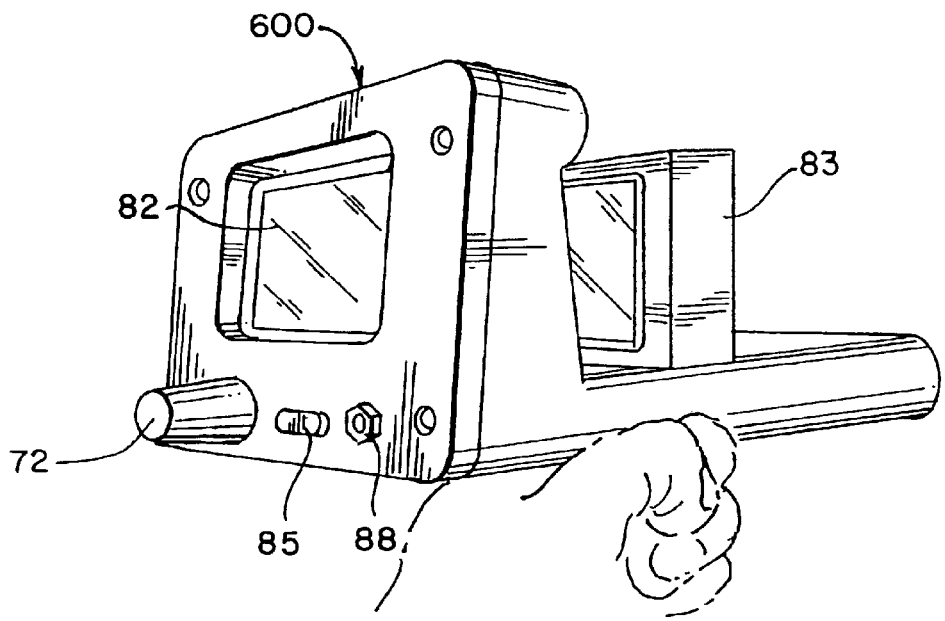
Figure 7:
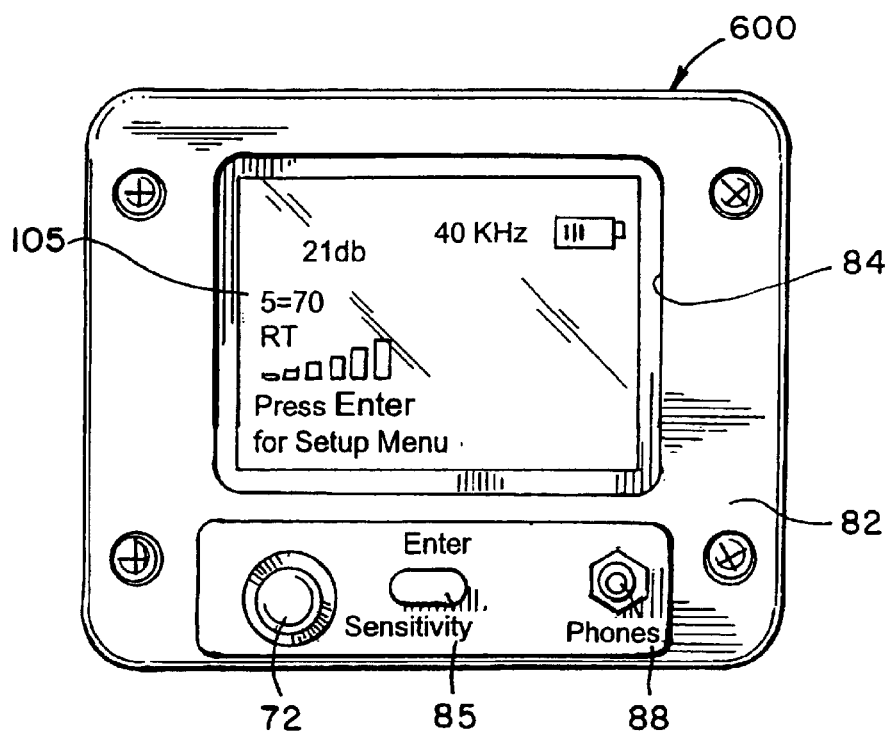
Figure 8:
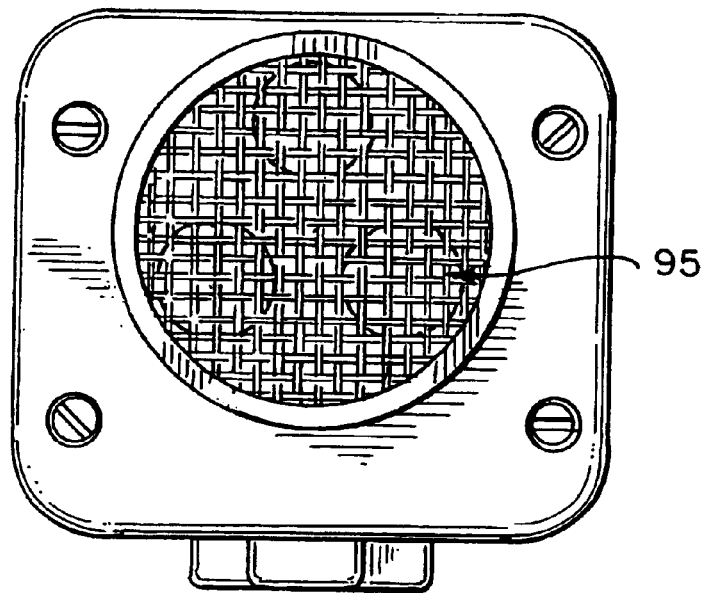

Frequency control of function generator circuits 20 and 32 is achieved by the micro-controller 80 (see FIGS. 3A thru 3B-9). As shown in FIG. 2F-1, an input signal 302 VOF is applied to the positive input (pin 5) of amplifier 51 (U7B). VOF 302 originates from the DAC 71 which is on the I/O board (FIG. 3B-3). The voltage level of VOF is from approximately 0 to 4.095 volts. The oscillation frequency of circuit 20 and circuit 32 is set during a calibration process by way of variable resistors 330 (VR5) and 180 (VR3) (see FIGS. 2F-1 and 2F-2). In accordance with the invention, when the frequency of the system is tuned, voltage VOF is changed, i.e., the voltage applied to pin 5 of amplifier 51 is changed (FIG. 2F-1). As a result, the frequency of the local oscillators of circuit 20 and circuit 32 can be changed in the range from approximately 20 kHz to 100 kHz.

In accordance with the invention, the output from heterodyne circuit 20 (FIG. 2F-1) is provided to amplifier 24 on line 340, as shown in FIG. 2H-1. Connected to amplifier 24 are resistors 345 (R73), 344 (R65), and capacitors 342 (C47), and 346 (C53). The output signal meter (pin 1) of amplifier 24 is provided to an additional circuit for conversion into RMS units and dB units (see FIGS. 2J-1 thru FIG. 2J-3). The collector of transistor 74 (Q5) (FIG. 2H-1) is connected to the positive input of amplifier 24, while the base of transistor 74 is connected through resistor 348 (R80) to OFF signal output from amplifier 60 FIG. 2I-2). As a result, when the battery level falls below the optimum operating level, the base of transistor 74 is pulled high and the output signal from amplifier 24 is terminated. Typically, amplifier 24 is a standard "off-the-shelf" IC, such has an OP-284ES.

The output signal meter (pin 1) of amplifier 24 shown in FIG. 2H-1 is provided to the input of amplifier 61 (U9B) by way of connector J11 (FIG. 2J-1). Connected to the positive input (pin 5) of amplifier 61 are resistors 400 (R106) and 405 (R107). A low pass filtered output signal from amplifier 61 is provided to the positive input (pin 3) of amplifier 62 (U9A) through capacitor 411 (C74) where it is buffered and output from pin 1 of amplifier 62 over resistor 420 (R105) and capacitor 423 (C72) to pin 15 of RMS-to-DC convertor 65 (U19). Typically, amplifiers 61 and 62 are standard ICs, such as an OP-284-ES. RMS-to-DC convertor 65 is typically a standard "off-the-shelf" IC, such as an AD637 manufactured by Analog Devices.

With further reference to FIG. 2J-2 RMS-to-DC convertor 65 computes the root-mean-square, or the mean square of the absolute value of the input signal at pin 15 of converter 65 and provides an equivalent dc output voltage at pin 16, as well as an RMS output at pin 11. The DC output voltage at pin 16 of converter 65 varies linearly to the dB level of the input signal's amplitude at pin 15 of converter 65. Here, the dc output voltage is a buffered output that is provided to amplifier 67 (U17A) by way of resistor 426 (R110) and resistor temperature compensator 429 (RT1).

Resistors 432 (R111), 435 (R108) and variable resistor 438 (VR10) are coupled to amplifier 67. Together, these resistors control the gain of amplifier 67 to thereby scale the dB level of the output signal that is seen on connector J11. Here, R108 is not installed so VR10 completely controls the scaling of the dB output signal from amplifier 67. This output signal is forwarded by way of pin 1 (TP21) on connector J11 to the I/O board shown in FIGS. 3B thru 3B-9 and the micro-controller shown in FIG. 3A thru FIG. 3A-10.

As further shown in FIG. 2J-2 voltage regulator 64 (U20) is connected to BUFIN (pin 1) of the RMS-to-DC convertor 65. The voltage regulator 64 receives +12V2 that is supplied on connector J11 from the power supply (FIG. 2K-1) and converts this 12 volt input voltage to a regulated output voltage that is output on pin 2 of regulator 64. Resistors 441 (R113), 444 (R113), and 447 (R112) set the level of a regulated output voltage from regulator 64, where variable resistor 450 (VR11) provides a means to adjust the output current and set the 0 dB reference level for converter 65 of this regulator. Typically, the voltage regulator 64 is a standard "off-the-shelf" IC, such as a LM317 manufactured by National Semiconductor Corporation.

Coupled to output offset (pin 4) and analog common (pin 3) of the RMS-to-DC convertor 65 is a voltage regulator 66 (U21) that also receives the +12V2 voltage from the power supply. The voltage regulator 66 provides a +5 volt output that is also supplied to the positive input (pin 3) of amplifier 67. Voltage regulator 66 is typically a standard "off-the-shelf" IC, such as a LM78L05CM.

RMS output (pin 11) of the RMS-to-DC convertor 65 is provided to the positive input (pin 5) of amplifier 63 through resistor 453 (R102). Averaging capacitor 464 (C75) is connected across pins 11 and 10 of convertor 65 and is used to determine the averaging error that occurs during the calculation of the true RMS of the input signal supplied to pin 15 of the convertor 65. The magnitude of the error is dependent on the value of capacitor 464. As shown in FIG. 2J-3, the RMS output from pin 7 of amplifier 63 is forwarded by way of pin 2 of connector J11 to the I/O board shown in FIG. 3(b) and the micro-controller shown in FIG. 3(a). Typically, amplifiers 63 and 67 are standard "off-the-shelf" ICs, such as a LM6132AIM.

The dB output signal at J11 pin 1 (FIG. 2J-1) has a 50 dB dynamic range, a 0–5V DC scale for direct input to the micro-controller, and an accurate linear dB format. These provide an elimination of the need for expensive DSP processors or math co-processors, a limitation or reduction of the memory requirements for data and code, and because of the accurate analog preprocessing, an elimination of the need for elaborate signal analysis or data conversion algorithms. In addition, a reduction of signal processing time is also provided, as well as reduced processor clock speeds which in turn lowers power consumption. It should be noted that this invention performs real time analog signal processing on the heterodyned signal only.

Turning now to FIG. 2K-2, therein shown is an audio amplifier that is used to provide an audio output signal that is supplied to a pair of headphones connected to the jack 88 (J12) on the rear panel of the housing (FIG. 7).

As stated previously, the audio signal on line 304 is applied to one input of the inputs of the summing amplifier 68. An input alarm signal is supplied to the second input of the summing amplifier through capacitor 509 (C62), resistors 500 (R90), 503 (R91), and variable resistor 506 (VR15). Voltage follower amplifier 69 (U15A) utilizes the +12V voltage from the power supply to create a 6 volt reference level (pin 1) that is supplied to the positive input (pin 5) of summing amplifier 68.

The output signal from the summing amplifier 68 is applied to audio amplifier 40 (U16) which is transformer coupled by transformer 41 (T1) to the jack 88 on the rear panel of the housing (FIG. 7). Control of the audio volume is achieved by a signal VOL that is provided on connector J7 through resistors 518 (R96), 521 (R97) to pin 4 of amplifier 40. In preferred embodiments, amplifier 40 is a standard "off-the-shelf" IC, such as a TDA7052A manufactured by Philips Semiconductors.

Figure 9A:
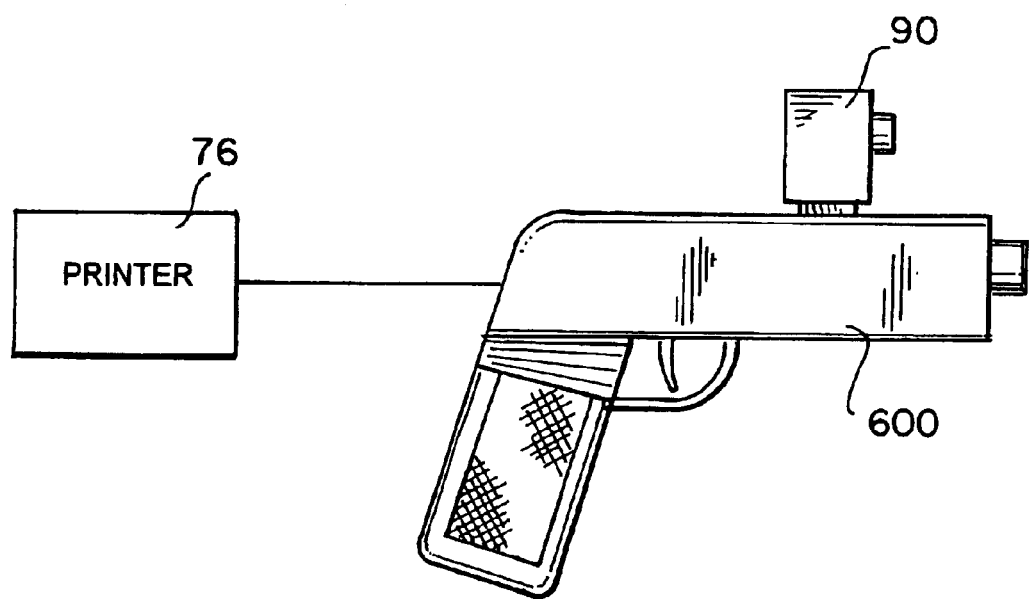
FIGS. 9(a) and 9(b) are block diagrams of an additional aspect of the invention.
Figure 9B:
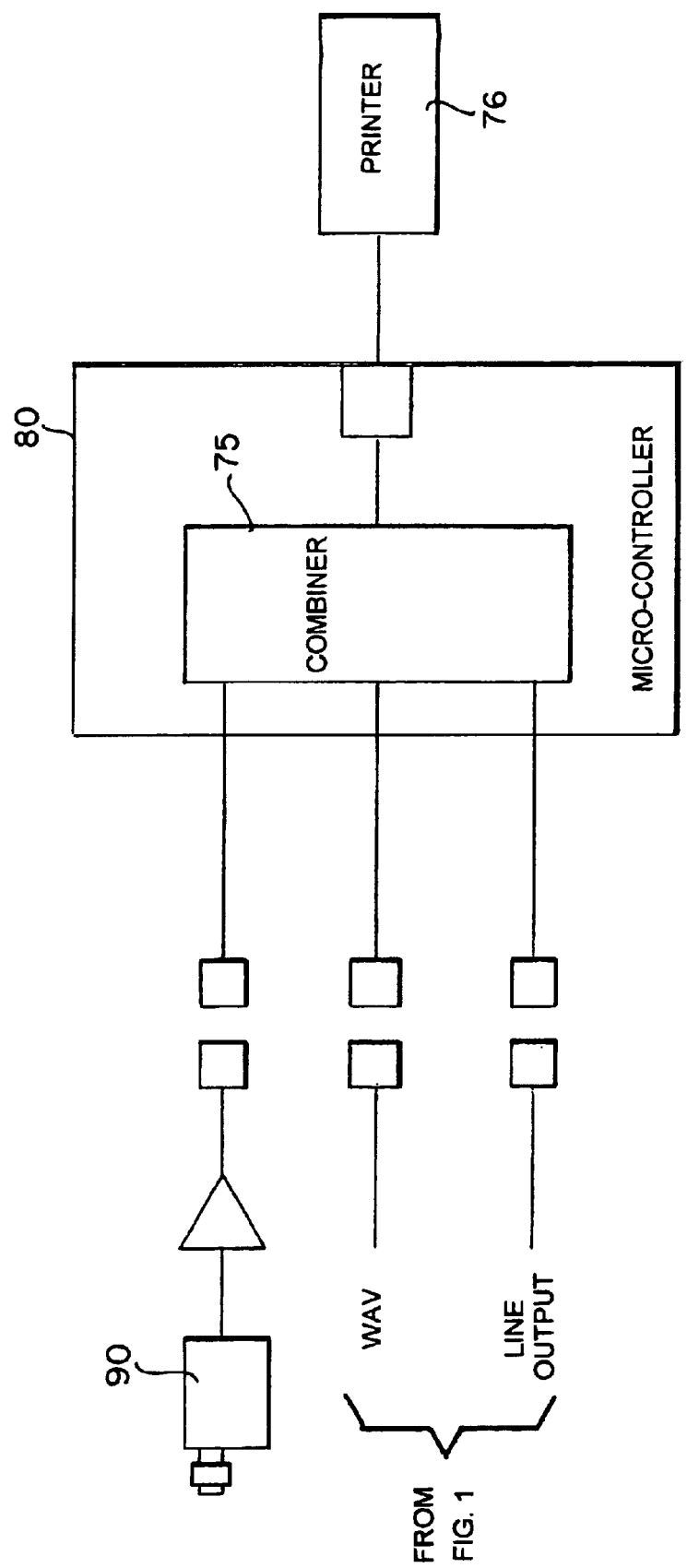
Figure 10:
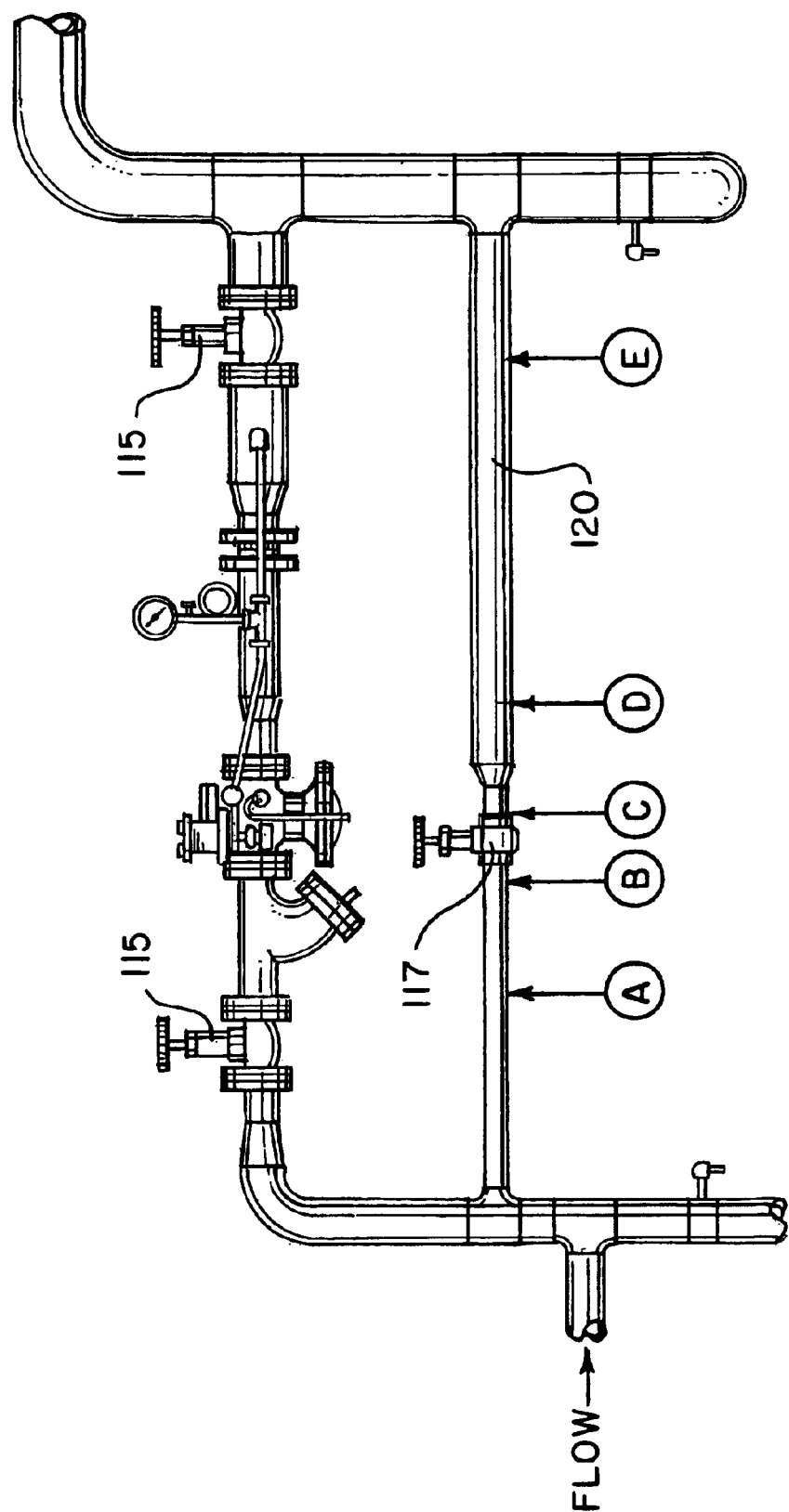

FIGS. 9(a) and 9(b) are block diagrams of an additional aspect of the invention. In FIG. 9(b), a digital camera 90 is used to make a picture of the device being ultrasonically measured. The camera 90 is typically mounted on the detector housing (FIG. 9(a)). The picture signal and the signal from the dual heterodyne circuit may be combined in a circuit 75, but the camera may be activated independently of the system. The combiner 75 may be connected to a printer 76 and transmits print information directly to the printer from a user in a manner that is known. In preferred embodiments, the camera is a digital camera that stores image files. Thus, pictures of the device under test may be printed, as well as text results.

In certain embodiments, the camera utilizes a laser beam to pinpoint the location of the image. The recorded image is then "coupled" or "linked" to the stored information for that location, e.g., ultrasonic data, WAV file, and atmospheric conditions. The recorded image and the stored information for the image location is then uploaded to a suitable portable storage device in the instrument, such as a flash card 83 (FIG. 4 and FIG. 6), smart media or memory stick. The recorded image and the stored information is then downloaded to a data base computer and incorporated into a data base program that generates a report for determining the condition of the device being measured.

With specific reference to FIG. 9(b), when an ultrasonic measurement of a device is performed, a picture can be captured and stored in memory using the camera 77. The picture can then be forwarded to micro-controller 80 where it is combined with the WAV and line output from the second heterodyne circuit 32 (see FIG. 2F-1) in combiner 75 for output to the printer 76. In preferred embodiments, the printout comprises a spectral display of the line output and a graphical display of the WAV file information from the second heterodyne circuit 32 (see FIG. 2F-1), as well as a picture of the device under test.

With reference to FIG. 3A-1, sensitivity encoder 100 is used to increase or decrease the sensitivity level of the dual heterodyne circuit in accordance with the present invention. As shown in FIGS. 6 and 7, the sensitivity is adjusted by turning a rotational knob 72 that is located at the back of the housing. In preferred embodiments, the sensitivity encoder 100 is a rotational optical encoder.

Rotation of the sensitivity encoder 100 by way of knob 72 changes a signal on P24 (FIG. 3B-5 which causes D/A converter 71 to the change the output level of the control voltage VOS 302 on connector J13 (FIG. 3B-8) that controls the gain of VCA 14 (see FIG. 2A-2). Consequently, changes in the gain of VGA 14 produce proportional changes in the sensitivity level of the dual heterodyne circuit.

With reference to FIG. 7, LCD 82 provides a display of data that is used to distinguish between trends or deviations in readings. As a result, a user is provided with the means to bypass valve analysis and pinpoint an ultrasonic source, such as an internal leak in a tank or vessel, or an underground leak in gas piping or electrical transmission lines.

Sensitivity level indicator 105, shown on the LCD 82, provides the user with the ability to view the sensitivity level setting of the dual heterodyne circuit. As a result, the user can consistently set the sensitivity level of the circuit to permit repeated comparative frequency spectrum measurements, where repeatability is critical. As shown in FIG. 7, LCD 82 displays the sensitivity level setting as a range of integer numbers. In the preferred embodiment, this range is from 0 to 70, where S is an abbreviation for sensitivity.

In accordance with the invention, the integer numbers represent the adjustment range of VGA 14 (FIG. 2A-2), where each integer value corresponds to one decibel in the change of the gain of VGA 14. In accordance with the preferred embodiment, a sensitivity level setting of 70 corresponds to maximum sensitivity while a sensitivity level setting of 0 corresponds to a minimum sensitivity setting (70 dB below maximum sensitivity). In accordance with the invention, the sensitivity setting is also a field in the memory of the portable ultrasonic detector so that when the user presses the store button 85, the sensitivity level setting value is stored. In certain embodiments of the invention, the user can also annotate data files that are stored, and by way of voice recognition incorporate them into a final report.

In accordance with the invention, "Spin and Click™" controls are used to provide an end user interface that is simple and intuitive. With reference to FIG. 7, knob 72 acts as a cursor control. As knob 72 is clicked, the cursor moves in a set pattern around the display screen 82. If a "function field" is blinking, knob 72 is then spun to change the values within the function field. Once a function is selected, knob 72 is then clicked to set the selected value.

In accordance with the preferred embodiment of the invention, multiple applications can be displayed. In the preferred embodiment, 6 applications can be displayed, i.e., GENERIC, LEAKS, STEAM TRAPS, VALVES, BEARINGS AND ELECTRICAL. Each application has two screens, i.e., MAIN and STORAGE. In addition, the screens VALVES AND BEARINGS have an ABCD SCREEN. The "Click" on knob 72 moves the "cursor" to "FIXED" positions on each screen. In certain embodiments, the number of controls are minimized. In the preferred embodiment, two controls are used to permit the user to "navigate" through the various display screens, and change multiple operational settings.

Figure 11A:
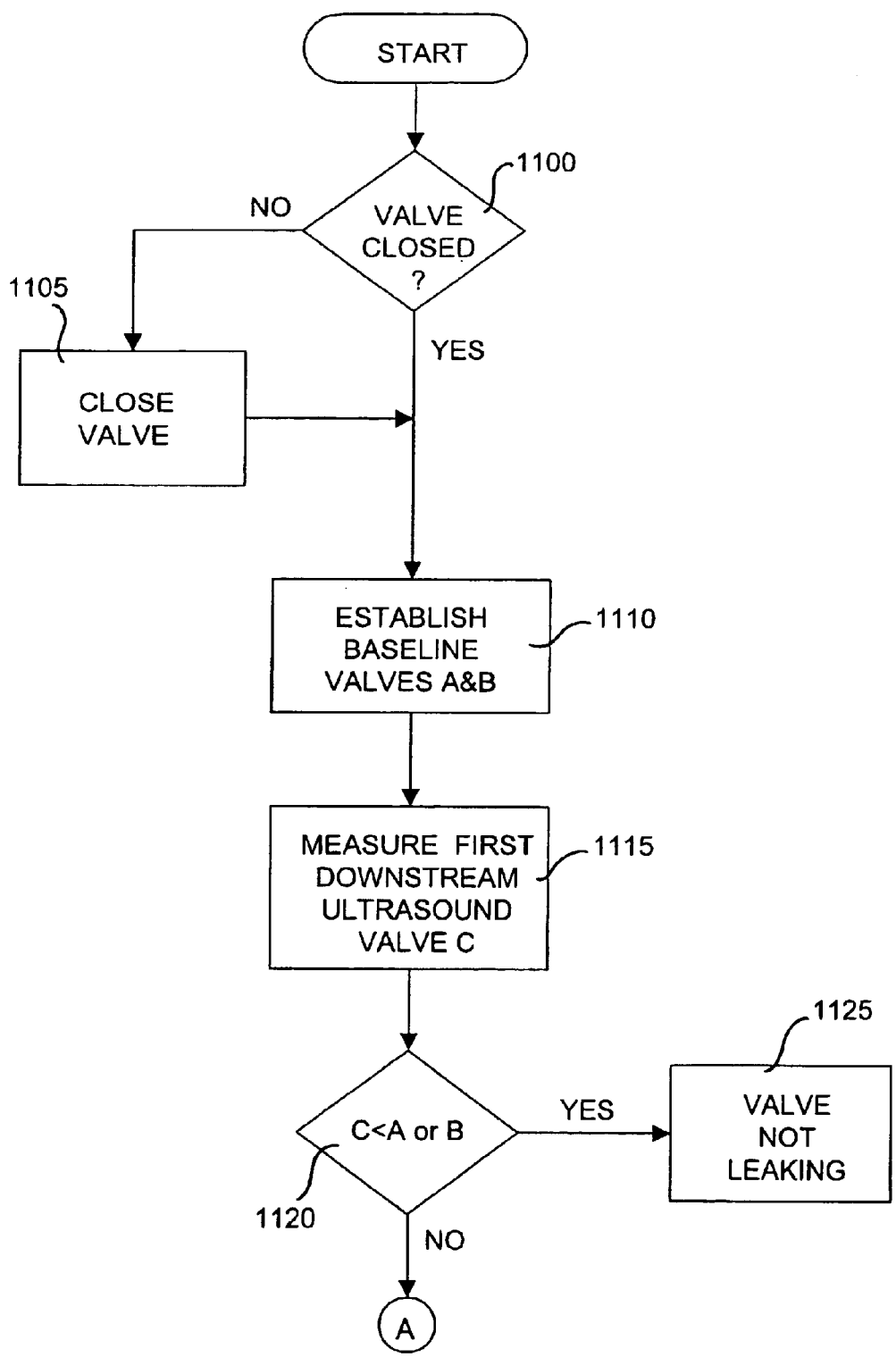
FIGS. 11(a), 11(b) and 11(c) are a flow chart illustrating the steps of the method of the invention.
Figure 11B:
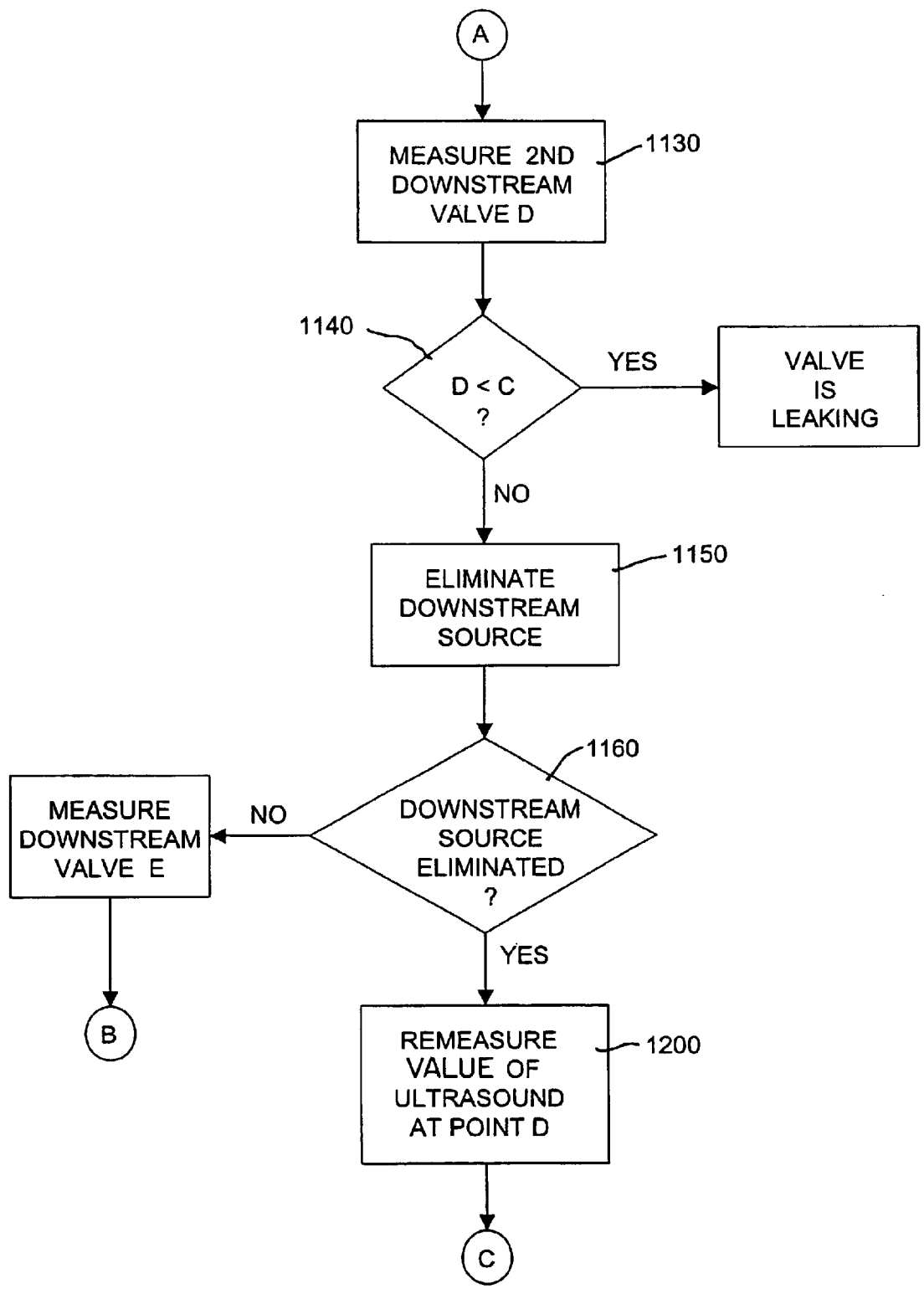
Figure 11C:
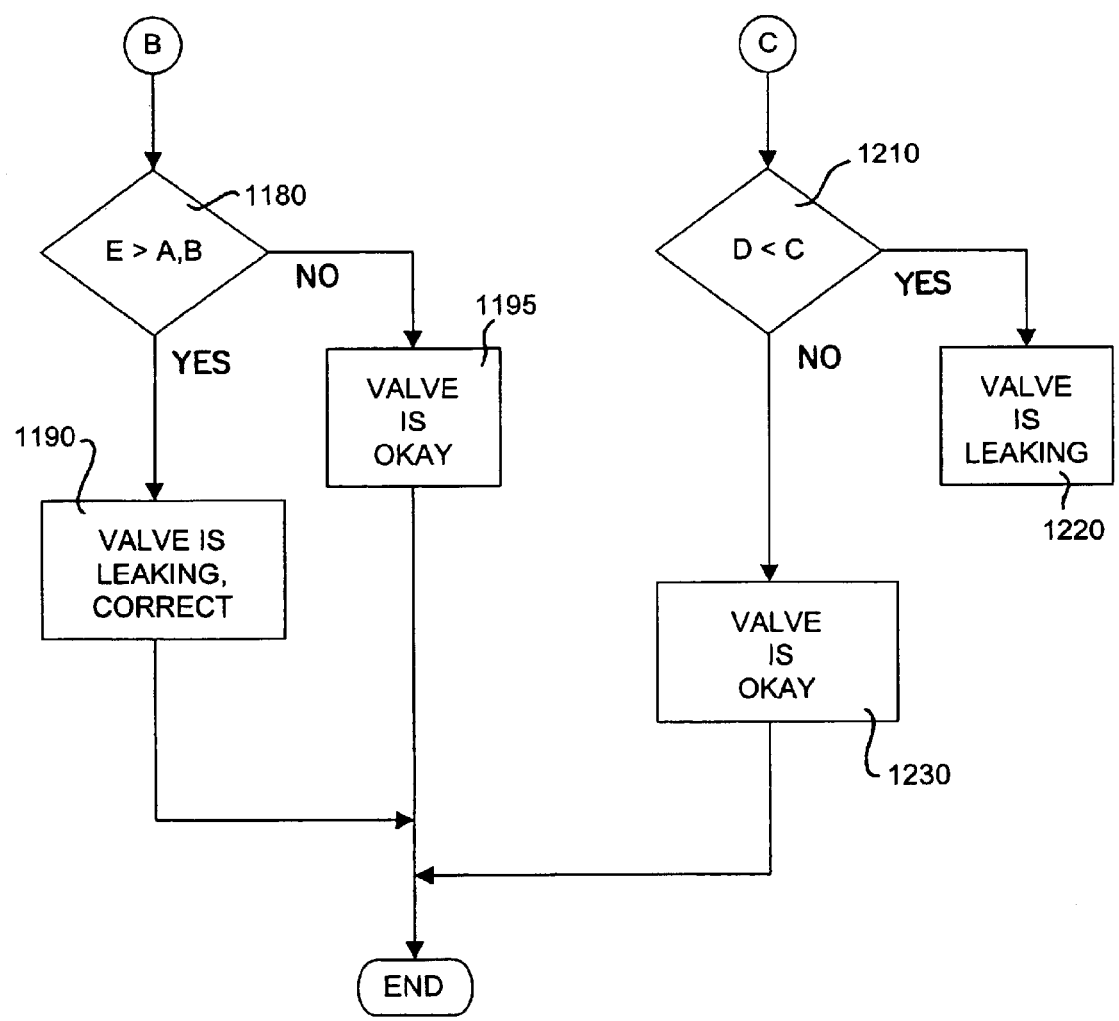

FIG. 10 is an illustration of an exemplary network of piping including valves that can be tested with the portable ultrasonic detector of the present invention. FIGS. 11(a) and 11(b) represent a flow chart illustrating the steps of the method of the invention. In accordance with the invention, the method is implemented by performing a visual inspection of valve 117 (see FIG. 10) to confirm that it is closed or in the off position, as indicated in step 1100. If the valve 117 is not closed (step 1105), then the operator closes the valve, and proceeds to the next step where a base line measurement for the valve 117 is established, as indicated in step 1110.

In accordance with the method of the invention, the ultrasound is measured at multiple points upstream and downstream from the valve. In the preferred embodiment, two upstream points A, B and two downstream points C, D are measured. With reference to FIG. 10, the first upstream measurement point A is at a distance located X times the pipe diameter from the valve. The second upstream measurement point B is located directly upstream from the valve, approximately at the pipe fitting. In accordance with the method of the invention, the two downstream measurement points C, D are at a distance of equal relationship to the upstream test points, i.e., the first downstream measurement point C is located directly downstream from the valve, approximately at the pipe fitting, and the second downstream measurement point D is at a distance located X times the pipe diameter from the valve. In the preferred embodiment, X is six (6). In other words, the first measurements points (A upstream or D downstream) are located at a point that is 6 times the diameter of the pipe 120 away from the valve.

While touching a contact module to a measurement point to measure the ultrasonic energy at the two upstream points, the sensitivity of the dual heterodyning circuit is adjusted by turning the rotary knob 72 on the rear of the portable device so that the LCD 82 displays the dB value of the ultrasonic measurements. The value of the ultrasound at these initial upstream points establishes the baseline measurements for the valve 117. The ultrasonic measurement at the first and second upstream points should be close to each other. In some circumstances, the value of the ultrasound at the second upstream measurement point can be slightly lower than the value of the ultrasound at the first upstream measurement point. In contemplated embodiments, the second measurement is performed without re-adjusting the sensitivity of the dual heterodyne circuit.

The first of two downstream test points C, D is then measured to obtain the level of the ultrasound at this downstream test point C, as indicated in step 1115. The value of the ultrasound at the first downstream test point C is compared to the values of the ultrasound at the upstream test points A, B, as indicated in step 1120.

The ultrasound at the second downstream test point D is measured to ensure that no ultrasonic sound is emanating downstream from the valve 117, as indicated in step 1130. The value of the ultrasound at the first downstream test point C is compared to the values of the ultrasound at the second downstream test point D, as indicated in step 1140. If the value at test point D is less than the value at C, the valve is leaking.

If the value of the ultrasonic sound measured at the second downstream point D is greater than the value of the ultrasonic sound measured at the first downstream point C, then an attempt should be made to "tune out" or "shut off" this ultrasonic sound to obtain a proper test of the valve, as indicated in step 1150. The ultrasonic sound may be "tuned out" or shut off by simply locating source of the sound, and taking measure to eliminate it, such as closing valve 115 in FIG. 10. When it is determined in step 1160 that it is not possible to tune out or shut off a downstream structure borne ultrasound, it is necessary to locate the source of the highest reading to determine its effect on the outcome of the measurements. To accomplish this, an additional measurement of the ultrasound at a measurement point E is performed to assist in locating/confirming the source of the ultrasound, as indicated in step 1170. Hence, if it is determined in step 1180 that the value of the ultrasound at the downstream point E is higher than the values of the upstream points A, B, then the valve 117 is leaking, and measures are taken to correct the leak, such as by replacing the valve, as indicated in step 1190. If in step 1180 it is found that the value of the ultrasound at point E is lower than the value of the ultrasound at the upstream points, the valve is operating properly and does not need to be replaced (step 1195).

If it is determined in step 1160 that it is possible to eliminate tune out or shut off a downstream structure borne ultrasound, the value of the ultrasonic sound at the downstream point D is re-measured, as indicated in step 1200. A comparison of the values of the ultrasonic sound at the downstream points D and C is made, as indicated in step 1210. If the value of the ultrasound at downstream point D is less than the value of the ultrasound at downstream point C, the valve is leaking and must be changed, as indicated in step 1220. On the other hand, if the value of the ultrasound at downstream point D is greater than the value of the ultrasound at downstream point C, the valve is not leaking and does not need to be changed, as indicated in step 1230.

If the values of the ultrasound at the downstream points C, D are close to or lower than the values of the ultrasound at the upstream points A, B, then the valve 117 is not leaking, i.e., the valve is good, as indicated in step 1125 (see FIG. 11(a)).

In accordance with the invention, if the valve is working properly, then downstream baseline decibel values are recorded and stored in memory for subsequent comparisons to determine whether the valve is developing a leak. This is accomplished by re-measuring the ultrasonic energy at the downstream locations and comparing the energy to the original downstream baseline decibel values. If the ultrasonic energy at the re-measured downstream locations is greater than the value of the downstream baseline values, then the valve is developing a leak, and measures can be taken to correct the problem, such as replacing the valve.

In an alternative embodiment of the invention, where it is not possible to use multiple upstream and downstream test point, measurements are performed immediately upstream from the valve. A measurement is then performed at a test point directly on the body of the valve. In this manner, upstream values are obtained and compared with the subsequent downstream valves to determine whether the valve is leaking or not.

In accordance with the contemplated embodiments of the invention, the ultrasonic sound at the valve measurement points is recorded and downloaded to a computer using spectrum analysis software. In the preferred embodiment, the ultrasonic sound is digitized and stored on the flash card 83 (see FIG. 4 and FIG. 6), and subsequently analyzed with the spectrum analysis software. In accordance with this preferred embodiment, the spectrum analysis software is Spectralizerr™. In alternative embodiments, the ultrasonic sound at the valve test points is recorded directly to a vibration analyzer to observe the amplitude of the ultrasonic signal at each measurement point.

The dual heterodyning circuit of the present invention provides an enhanced output spectrum. As a result, it is easier to determine whether the resonance is mechanical or electrical. In addition, fault frequencies are also more easily detected. The enhanced signal output provides a lower signal-to-noise ratio, so as to increase the ease with which frequency components are analyzed. The method of the invention permits a user of the portable ultrasonic device to quickly and easily determine whether a valve is leaking or not In addition, the method of the invention eliminates the unnecessary replacements of "good" valves, which can be expensive in certain environments, such as in a nuclear plant or on a ship, where the valves are welded into place, by permitting a user to quickly and easily determine whether a valve is faulty.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A method for processing ultrasonic signals to locate faulty components in a system having upstream and downstream locations using a portable ultrasonic measuring device, comprising the steps of:

performing a visual inspection of a device in the system to ensure that the component is closed;

measuring ultrasonic energy levels at multiple upstream locations at fixed distances from the device to establish baseline ultrasonic energy values for the component while the system is operational;

measuring ultrasonic energy at locations downstream from the device;

comparing a first measured downstream ultrasonic value to the baseline ultrasonic energy values;

measuring a second downstream ultrasonic energy if the first measured downstream ultrasonic energy value is greater than the baseline ultrasonic energy values;

comparing the second measured downstream ultrasonic energy to the first measured downstream ultrasonic energy; and removing a downstream source of ultrasonic energy if the second measured downstream ultrasonic energy is greater than the first measured downstream ultrasonic energy to determine whether the device is faulty.

2. The method of claim 1, wherein said component is an on/off valve.

3. The method of claim 1, further comprising the step of closing the downstream source of ultrasonic energy; and returning to said establishing step.

4. The method of claim 3, wherein the ultrasonic energy level at two upstream locations is measured.

5. The method of claim 4, wherein a first upstream location is a predetermined distance from the component and a second upstream location is directly at the component.

6. The method of claim 5, wherein the predetermined distance is an integer value multiplied by a diameter of a pipe in the system.

7. The method of claim 6, wherein the integer is 6.

8. The method of claim 1, wherein said establishing step is performed while adjusting a sensitivity level of the portable ultrasonic measuring device;

wherein the sensitivity level of the portable ultrasonic device is adjusted such that a dB value of the ultrasonic energy is displayed on a display of the portable ultrasonic device.

9. The method of claim 8, wherein the sensitivity is adjusted by turning a knob located on a rear panel of the portable ultrasonic measuring device, said knob also permitting navigation between various display screens on a display of the apparatus.

10. The method of claim 1, wherein said step of measuring ultrasonic energy at downstream locations comprises the steps of:

measuring the ultrasonic energy level at a first downstream location that is a predetermined distance from the component; and measuring the ultrasonic energy level at a second downstream location directly at the component.

11. The method of claim 10, wherein the predetermined distance is an integer value multiplied by a diameter of a pipe in the system.

12. The method of claim 11, wherein the integer is 6.

13. The method of claim 1, further comprising the steps of:

measuring ultrasonic energy at an additional downstream point to locate an ultrasonic sound source.

14. The method of claim 1, further comprising the step of:

recording downstream baseline decibel values; and storing the downstream baseline values in memory for comparisons with future downstream baseline values to determine whether the component is leaking.

15. The method of claim 14, further comprising the step of:

re-measuring the downstream baseline decibel values;

retrieving the stored baseline decibel values from the memory; and comparing the retrieved baseline decibel values to the re-measuring the downstream baseline decibel values; and replacing the component if the re-measured downstream baseline decibel values are greater than the retrieved baseline decibel values.

* * * * *